United States Patent [19]

Odink et al.

[11] Patent Number: 5,702,920
[45] Date of Patent: Dec. 30, 1997

[54] DNAS ENCODING HUMAN MACROPHAGE MIGRATION INHIBITION FACTOR RELATED PEPTIDES

[75] Inventors: Karel Gerrit Odink, Rheinfelden; Roger Clerc, Basel; Nico Cerletti, Bottmingen; Josef Brüggen, Riehen, all of Switzerland; Lajos Tarcsay, Grenzach-Wyhlen; Clemens Sorg, Münster, both of Germany; Walter Wiesendanger, Münchenstein, Switzerland

[73] Assignee: Novartis Corporation, Summit, N.J.

[21] Appl. No.: 508,142

[22] Filed: Jul. 27, 1995

Related U.S. Application Data

[62] Division of Ser. No. 230,664, Apr. 21, 1994, abandoned, which is a division of Ser. No. 617,485, Nov. 21, 1990, Pat. No. 5,350,687, which is a continuation of Ser. No. 104,744, Oct. 2, 1987, abandoned.

[30] Foreign Application Priority Data

Nov. 27, 1986 [GB] United Kingdom ............ 8628358
Oct. 3, 1996 [GB] United Kingdom ............ 8623850

[51] Int. Cl.$^6$ .................... C07K 14/52; C12N 15/19
[52] U.S. Cl. ............ 435/69.5; 435/91.4; 435/252.33; 435/320.1; 435/325; 536/23.5; 536/25.3; 530/351; 530/412; 530/413
[58] Field of Search .................... 530/412, 351, 530/413, 416, 417; 435/69.5, 91.4, 240.2, 252.33, 254.21, 320.1, 325; 536/23.5, 25.3

[56] References Cited

U.S. PATENT DOCUMENTS

| 4,322,274 | 3/1982 | Wilson et al. ............ 435/6 |
| 4,667,017 | 5/1987 | Ishida ............ 530/402 |
| 4,833,074 | 5/1989 | Fagerhol et al. ............ 43/7 |
| 5,411,882 | 5/1995 | Odink et al. ............ 435/252.33 |

FOREIGN PATENT DOCUMENTS

| 162812 | 5/1985 | European Pat. Off. . |
| 230876 | 9/1983 | Germany . |

OTHER PUBLICATIONS van Heyningen et al, "Tissue Localization and Chromosomal Assignment of a Serum Protein that Tracks the Cystic Fibrosis Gene", *Nature* 315:513–515 (Jun. 1985).
Burmeister et al, Lymphokine Res. 3(4):236 (Summer 1984).
Sorg, "Modulation of Macrophage Functions by Lymphokines" *Immunobiol.* 161: 352–360 (1982).
Huynh et al, pp. 49–78 in *DNA Cloning*, (IRL Press 1985).
Burgess, et al., "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue", *Journal of Cell Biology*, 111: 2129–2138 (199).

Burmeister, G., Abstract, "Use of a Monoclonal Antibody for the Detection of Human Macrophage Migration Inhibitory Factors (MIFs) in Isolated Cells and Tissues", *Lymphokine Research*, 3(4): 236 (1984).
Campbell, A.M., "Monoclonal Antibody Technology, The Production and Characterization of Rodent and Human Hybridomas", *Laboratory Techniques in Biochemistry and Molecular Biology*, Ch. 3,4,6–10, Elsevier, NY (1986).
Dorin et al., "A Clue to the Basic Defect in Cystic Fibrosis from Cloning the CF Antigen Gene", *Nature*, 326:614–617 (1987).
Fahlbusch et al., "Inhibition of Macrophage Migration by a Factor from Ascites Fluids of Ovarian Cancer Patients; II. Production and Characterization of an Anti–MIF Antibody", *Biomed. Biochim. Acta*, 45/(3): 371–384 (1986).
Fahlbusch et al., "Inhibition of Macrophage Migration by a Factor from Ascites Fluids of Ovarian Cancer Patients; III. Generation of Monoclonal Antibody Specific for Human MIF", *Biomed. Biochim. Acta*, 46(5): 397–406 (1987).
Hayward et al., "Monoclonal Antibodies to Cystic Fibrosis Antigen", *J. Immunol. Methods*, 91:117–122 (1986).
Kawaguchi et al., "A Monoclonal Antibody Against Migration Inhibitory Factor with MIF from the Human Lymphoblast Cell Line Mo", *J. Leukocyte Biol.*, 39:223–232 (1986).
Lagasse et al., Abstract, "Isolation and Expression of Two Human Genes Encoding Myelocyte–monocyte Specific Proteins Associated with the Macrophase Migration Inhibition Factor (MIF)", *Experientia*, 43:666 (1987).
Lazar et al., "Transforming Growth Factor α: Mutation of Aspartic Acid 47 and Leucine 48 Results in Different Biological Activities", *Molecular and Cellular Biology*, 8 (3) 1247–1252 (1988).
Neumann et al., "Detection of Macrophage Migration Inhibitory Factor by Monoclonal Antibody in Sezary Syndrome", *J. Invest. Derm.*, 88(6): 670–674 (1987).
Odink et al., "Two–calcium–binding proteins in infiltrate macrophages of rheumatoid arthritis", *Nature*, 330:80–82 (1987).
Odink et al., Abstract, "Cloning and Expression of Two Complementary DNAs Encoding Proteins that are Associated with Specific States of Mycloid Cell Differentiation", *Experientia*, 43:667 (1987).
Sorg et al., Abstract, "Chemical and Functional characterization of lymphokines", *Immunochemistry*, 102: 427 abstract #44130w (1985).

(List continued on next page.)

*Primary Examiner*—John Ulm
*Assistant Examiner*—Prema Mertz
*Attorney, Agent, or Firm*—Henry P. Nowak; James S. Elmer

[57] ABSTRACT

The invention concerns polypeptides related to human macrophage migration inhibition factor, in particular the polypeptides called MRP-8 and MRP-14, processes for their preparation, mRNAs, DNAs and hybrid vectors coding for those polypeptides, hosts transformed with such a hybrid vector, monoclonal and polyclonal antibodies to those polypeptides, and diagnostic methods for inflammatory conditions and cystic fibrosis.

13 Claims, 8 Drawing Sheets

OTHER PUBLICATIONS

Tao et al., "Studies of Aglycosylated Chimeric Mouse–Human IgG: Role of Carbohydrate in the Structure and Effector Functions Mediated by the Human IgG Constant Region", *J. Immunology*, 143(8): 2595–2601 (1989).

Weiser et al., "Generation of Human Hybridomas Producing Migration Inhibitory Fctor (MIF) and of Murine Hybridomas Secreting Monoclonal Antibodies to Human MIF", *Cellular Immunology*, 90:167–178 (1985).

DNAS ENCODING HUMAN MACROPHAGE MIGRATION INHIBITION FACTOR RELATED PEPTIDES

This is a divisional of Ser. No. 08/230,664, filed Apr. 21, 1994, now abandoned, which is a divisional of Ser. No. 07/617,485, filed Nov. 21, 1990, now U.S. Pat. No. 5,350,687; which is a continuation of Ser. No. 07/104,744, filed Oct. 2, 1987, now abandoned.

The invention concerns polypeptides related to human macrophage migration inhibition factor, processes for their preparation, mRNAs, DNAs and hybrid vectors coding for said polypeptides, hosts transformed with such a hybrid vector, monoclonal and polyclonal antibodies to said polypeptides and diagnostic methods for inflammatory conditions and cystic fibrosis.

BACKGROUND OF THE INVENTION

Human macrophage migration inhibition factor (MIF) belongs to the group of so-called lymphokines which comprises biologically active, soluble polypeptides that are secreted by lymphocytes and monocytes or macrophages when these are stimulated by antigens, mitogens or the like. Other examples of lymphokines are immune interferon (γ-interferon), interleukin 1 and 2 and macrophage-activating factor (MAF). These lymphokines control the differentiation, activation and proliferation of various cell types of the immune system.

According to the known state of the art, human MIF consists of a group of polypeptides that inhibit the migration ability of macrophages. Human MIF is secreted not only by activated lymphocytes, T- and B-cells, but also by non-lymphoid cells, for example by growing fibroblasts and certain tumour cells. MIF can be clearly differentiated from γ-interferon, macrophage-activating factor (MAF) and other lymphokines.

Human MIF plays a decisive role in the early phase of an inflammation reaction ("delayed type hypersensitivity reaction"). It induces the differentiation of monocytes and quiescent tissue macrophages to mature inflammatory macrophages. Human MIF and related proteins are therefore important markers for inflammatory conditions and may be useful in the therapy of immune regulation diseases and chronic inflammatory diseases.

The isolation and purification of a MIF protein of 8 kD molecular weight from human mononuclear cells stimulated with concanavalin A is described in European Patent Application EP 162 812. This protein is characterized by a N-terminal amino acid sequence (61 amino acids) and its macrophage migration inhibitory activity, further by its immunoreactivity towards selected monoclonal antibodies. Other MIF proteins of 14 kD, 28 kD and 45 kD are described, but poorly characterized. The MIF protein of 14 kD was found to have the same N-terminal amino acid sequence (amino acids 2 to 19) as the 8 kD MIF protein.

According to EP 162 812, human MIF and its proteins are obtained from cell culture supernatants or filtrates of stimulated human cells. This method limits the availability of human MIF due to inherent problems in culturing suitable human cells, the limited availability of fresh human MIF-producing cells, and cumbersome isolation of a single protein.

The fast progress in recombinant DNA technology in recent years provides the general methods for the preparation of polypeptides in large amounts independent of the primary natural sources of such compounds. Identification of a mRNA or a DNA coding for the desired polypeptide is crucial for the success of this approach. If (partial) amino acid sequence information is available, a chemically synthetized nucleic acid probe may lead to the isolation of coding mRNA or DNA from a mixture of mRNA derived from cells producing the desired polypeptides or from a DNA library, respectively. Although many examples for the isolation of a mRNA or DNA coding for a desired polypeptide have so far become known and the general procedure has been described in principle, each new specific problem requires adaption of the technique to the particular case.

Once a complementary or genomic DNA coding for the desired polypeptide is at hand, preparation of suitable expression vectors, transformation of hosts with these vectors, fermentation of transformed hosts and isolation of the expressed polypeptide follows standard procedures. Here again, these procedures must be adapted to the particular problem in order to get stable incorporation of the DNA and sufficiently high expression of the desired polypeptide in a chosen host organism, and acceptable yields of pure, biologically active isolated protein.

Furthermore recombinant DNA technology allows one to produce polypeptide variants by mutating or otherwise altering the coding DNA incorporated in a host organism, thereby enlarging the potential applications of an active principle found in a single polypeptide structure in nature.

A recent publication on cystic fibrosis antigen (CF antigen) isolated from chronic myeloid leukemia cells (J. R. Dorin et al., Nature 1987, 326, 614) suggests that this CF antigen is identical or at least very much related to the MIF-related protein MRP-8 of this invention. However, the present invention provides evidence that MRP-8 is not indicative for cystic fibrosis. At the same time a method of reliable diagnosis of cystic fibrosis is described by this invention based on the immunological determination of another MIF-related protein, MRP-14.

OBJECT OF THE INVENTION

It is an object of the present invention to provide polypeptides related to human macrophage migration inhibition factor (MIF) in high purity and sufficient quantity, and processes for their preparation. The problem of industrial polypeptide synthesis can be solved by the methods of recombinant DNA technology. A further object of the present invention is therefore to provide DNAs hybridizing with mRNA and DNA from natural sources coding for MIF-related peptides, DNAs and hybrid vectors coding for MIF-related polypeptides, and hosts transformed with such a vector. Other objects are methods of production of said hybrid vectors, transformed hosts, RNA and DNA molecules, also pharmaceutical preparations containing effective amounts of MIF-related polypeptides and methods of their preparation, and the use of said polypeptides.

It is a further object of the present invention to provide monoclonal and polyclonal antibodies directed to MIF-related polypeptides, hybridoma cell lines producing such monoclonal antibodies, methods of production of said antibodies and hybridoma cell lines and the use of said antibodies. A particular object is a method of reliable diagnosis of inflammatory conditions and cystic fibrosis. These objects have been achieved by the present invention.

DESCRIPTION OF THE INVENTION

The invention concerns human macrophage migration inhibition factor related peptides (MRP) of apparent molecular weight around 8 kD or around 14 kD, and mutants, fragments and derivatives thereof.

In particular the invention concerns MRP-8 of the formula

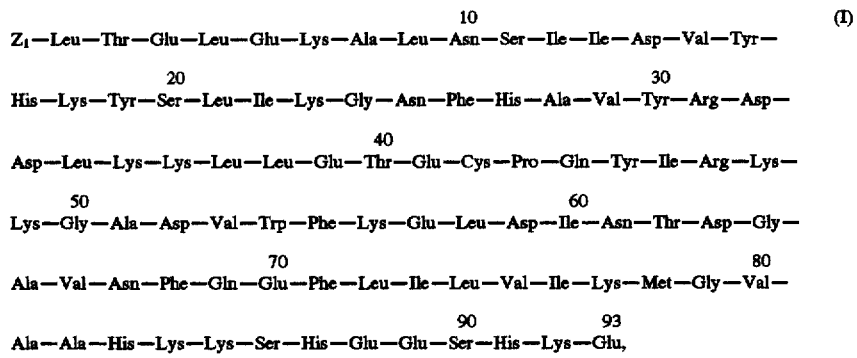

wherein $Z_1$ is hydrogen, acyl or the amino acid residue methionine, and mutants, fragments and derivatives thereof, and MRP-14 of the formula

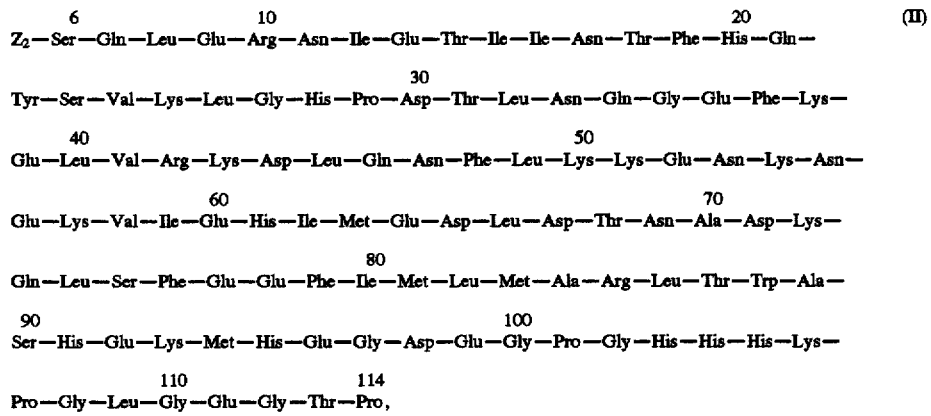

wherein $Z_2$ is hydrogen, acyl or an optionally acylated peptide residue of 1 to 5 amino acids, and mutants, fragments and derivatives thereof.

Acyl $Z_1$ or $Z_2$ is the acyl residue of a naturally occurring organic or inorganic acid, for example of formic acid, alkanecarboxylic acid, e.g. acetic, propionic, palmitic or myristic acid, or phosphoric or sulfuric acid, preferably acetic acid.

A peptide residue $Z_2$ is composed of one, two, three, four or five naturally occurring amino acids and is, for example, Met-, Thr-Cys-Lys-Met- or Met-Thr-Cys-Lys-Met-. Such a peptide residue may be acylated at the N-terminal amino group by an acyl residue as defined under acyl $Z_1$ or $Z_2$, e.g. acetyl, and is, for example, acetyl-Thr-Cys-Lys-Met-.

Mutants of the invention are polypeptides, wherein one or more, especially one, two or three, single amino acids of a compound of the formula I or II are replaced by a different amino acid or by a bond. Such mutants may be formed by spontaneous or chemically induced mutations at the DNA level or by replacement of amino acids by chemical synthesis.

Fragments of the invention are fragments of a compound of the formula I or II comprising at least 20 consecutive amino acids. Fragments of the invention may be formed by spontaneous or chemically-induced mutations at the DNA level, whereby a triplet coding for an amino acid is changed to a stop codon, or at the peptide level by cleaving peptide bonds chemically or enzymatically.

Derivatives of a polypeptide of formula I or II, mutant or fragment thereof are such wherein functional groups, e.g. amino, hydroxy, mercapto or carboxy groups, are derivatized, e.g. glycosylated, acylated, amidated or esterified. In glycosylated derivatives a carbohydrate residue or an oligosaccharide is linked to asparagine, serine and/or threonine. Acylated derivatives are substituted by the acyl group of a naturally occurring organic or inorganic acid, e.g. acetic acid, phosphoric acid or sulfuric acid, at amino groups, especially the N-terminal amino group, or at hydroxy groups, especially of tyrosine or serine. Esters are those of naturally occurring alcohols, e.g. of methanol or ethanol.

Derivatives of the invention are also dimers of a compound of the formula I or of a compound of the formula II, mutants or fragments thereof, wherein the mercapto group of a cystein residue is in the oxidized, i.e. disulfide form giving rise to intermolecular S—S bridges, and mixed dimers of a compound of the formula I, mutant or fragment thereof with a compound of the formula II, mutant or fragment thereof bound via the oxidized mercapto group of a cystein residue.

Further derivatives are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

Preferred is the compound MRP-8 of formula I, wherein $Z_1$ is Met, i.e. the amino acid residue methionine. The effective molecular weight of this polypeptide is 10.8 kD, but on sodium dodecyl sulfate polyacrylamide gel electrophoresis (SDS-PAGE), this peptide migrates as a peptide of 8 kD when compared with standard marker proteins.

Also preferred is the compound MRP-14 of formula II, wherein $Z_2$ is Thr-Cys-Lys-Met- or hydrogen. The latter compound is also called MRP-14d. The effective molecular weight of these polypeptides is 13.1 kD and 12.6 kD, respectively, but on SDS-PAGE, these peptides migrate as peptides of 14 kD when compared with standard marker proteins.

Preferred derivatives are dimers of MRP-8 of formula I, wherein $Z_1$ is Met, dimers of MRP-14 of formula II, wherein $Z_2$ is Thr-Cys-Lys-Met- and the mixed dimers of MRP-8 of formula I, wherein $Z_1$ is Met, with MRP-14 of formula II, wherein $Z_2$ is Thr-Cys-Lys-Met-, all bound via the oxidized mercapto group of a cystein residue.

The invention relates also to a process for the preparation of human macrophage migration inhibition factor related peptides, mutants, fragments and derivatives thereof, characterized in that a solution containing the desired compounds, for example a pre-purified extract, cell supernatant or culture filtrate of stimulated normal human leukocytes or of genetically engineered microorganisms or permanent mammalian cell lines, is purified by chromatographic methods and the compounds isolated and, if desired, fragments or derivatives prepared therefrom.

Pre-purified extracts, cell supernatants and culture filtrates of stimulated normal human leukocytes containing a compound of the formula II or derivatives thereof are prepared as described in EP 162 812. In particular, normal human mononuclear cells are stimulated to produce macrophage migration inhibition factor (MIF) and other lymphokines by suitable adjuncts, for example concanavalin A or phytohaemagglutinin, and are cultured according to customary methods. Extracts, cell supernatants or culture filtrates are then pre-purified by immunoaffinity chromatography on a column loaded with antibodies specific for human MIF, e.g. with monoclonal antibodies 1C5.

Extracts, cell supernatants and culture filtrates of genetically engineered microorganisms or permanent mammalian cell lines containing human macrophage migration inhibition factor related peptides are obtained and pre-purified as will be discussed hereinbelow.

Chromatographic methods contemplated for the preparation of the desired compounds are ion exchange chromatography, reversed phase high performance liquid chromatography, gel filtration, affinity chromatography, chromatography on hydroxylapatite, hydrophobic interaction chromatography and the like.

A suitable carrier material for ion exchange chromatography may be of organic or inorganic origin, e.g. cross-linked agarose, dextran, polyacrylamide, styrene/divinylbenzene copolymer, cellulose, or the like. This carrier material bears basic functional groups, e.g. tertiary amino functions, quaternary ammonium groups or acid functional groups, e.g carboxylic or sulfonic acid residues. Examples for preferred ion exchangers are those bearing diethylaminoethyl (DEAE) or diethyl-2-hydroxypropyl-ammonioethyl functional groups and those bearing sulfopropyl (SP) or carboxymethyl (CM) functional groups, either attached to carriers suitable for normal liquid chromatography, fast protein liquid chromatography (FPLC) or high performance liquid chromatography (HPLC). The separations and purifications with ion exchange chromatography are performed following established procedures, e.g. in aqueous buffer solutions of pH 5 to pH 9 containing increasing amounts of salt, for example sodium chloride.

Carrier material suitable for gel filtration or size exclusion chromatography includes cross-linked dextran, agarose, suitably modified polyacrylamide or silica, and the like. Optionally these carriers are modified with substituents bearing hydroxy functions, e.g. with 1-hydroxy- or 1,2-dihydroxy-lower alkyl groups. The chromatographic material is chosen so as to display optimal separation of peptides in the range of 5'000 to 20'000 Dalton (5 kD to 20 kD) molecular weight. Such gel filtration or size exclusion chromatography may be performed in a column suitable for normal liquid chromatography, FPLC or HPLC as above using aqueous buffer solutions around neutrality containing variable amounts of salt, e.g. sodium chloride.

Reversed phase chromatography is performed on silica-based carrier material bearing hydrophobic groups, e.g. alkyl groups of 1 to 20 carbon atoms, preferably 4, 8, 12 or 18 carbon atoms or mixtures of alkyl groups of 1 and 8 or 2 and 18 carbon atoms, respectively, or phenyl groups. Related to this method is the hydrophobic interaction chromatography, wherein agarose or a related material coated with alkyl groups of up to 12 carbon atoms and/or phenyl groups is used. These chromatographic techniques are applied using FPLC or HPLC. Solvents for processing of the polypeptides of the invention on silica-based reversed phase material are aqueous acids, e.g. aqueous trifluoracetic acid, containing increasing amounts of a polar, water-miscible organic solvent, e.g. acetonitrile, lower alcohols, e.g. methanol, ethanol or propanol, tetrahydrofuran, and the like, preferably acetonitrile.

Affinity chromatography is also contemplated for the purification of the peptides of the invention, using a suitable carrier material, e.g. cross-linked agarose, dextran or polyacrylamide bearing molecules with high affinity for a compound of formula I, mutants, fragments and derivatives thereof, for example antibodies, in particular polyclonal and monoclonal antibodies specific for the peptides of the invention as described hereinbelow.

The preferred chromatographic methods are ion exchange chromatography with carriers bearing sulfopropyl groups and reversed phase high performance liquid chromatography (HPLC).

The compounds of the invention are isolated by the usual techniques, for example filtration or ultrafiltration, dialysis, dissolution and reprecipitation in suitable salt and/or buffer solutions and solvent mixtures, solvent evaporation, lyophilization and the like.

Fragments of a MIF-related peptide are prepared e.g. by treatment with a protease. For example, papain, trypsin, α-chymotrypsin, thermolysin, pepsin, subtilisin, endoproteinase Lys-C from *Lysobacter enzymogenes*, V8 protease from *Staphylococcus aureus* or related proteases may be added to a solution of a compound of formula I or II, and the resulting mixture of fragments separated by chromatographic methods, e.g. by gel filtration and/or reversed phase HPLC.

Dimers of compounds of formula I or II containing a Cys residue are obtained by mild oxidation, e.g. with air, oxygen, iodine, dimethylsulfoxide and HCl or HBr, or other chemical oxidants. Conjugates of compounds of formula I with compounds of formula II are prepared likewise by oxidation of a suitable mixture.

In particular, compounds of the formula I or II, mutants, fragments and derivatives thereof can be prepared by recombinant DNA technique comprising, for example, culturing a transformed host expressing a peptide of the formula I or II, a mutant or derivative thereof under conditions which allow expression of the heterologous polypeptide and isolating the desired compound. More specifically, the desired compounds are prepared by a) isolating a DNA coding for a compound of formula I or II, or a fragment thereof from a cDNA or a genomic DNA library of human cells and optionally mutating it, or chemically synthesizing such a DNA, b) incorporating the DNA into an appropriate expression vector, c) transferring the obtained hybrid vector into a recipient host, d) selecting the transformed host from untransformed hosts, e.g. by culturing under conditions under which only the transformed host survives, e) culturing the transformed host under conditions which allow expression of the heterologous polypeptide, and f) isolating the compound of formula I or II, mutant, fragment or derivative thereof, and, if required, derivatizing the obtained compound of formula I or II, mutant or fragment thereof.

The steps involved in the preparation of these peptides by recombinant DNA technique will be discussed in more detail hereinbelow.

It is also possible to synthesize a compound of formula I or II, mutants and particularly fragments thereof by chemical methods, e.g. by condensation reactions as described in M. Bodanszky, Principles of Peptide Synthesis, Springer-Verlag 1984. Fragments are synthesized e.g. by a solid-phase method, wherein a N-protected amino acid is coupled to a suitable resin, the protecting group is removed, a second N-protected amino acid is condensed with the amino group of the first amino acid, the cycle of deprotection/ condensation with the next N-protected amino acid is repeated until the peptide residue of the desired composition is complete, and finally this peptide residue is cleaved from the resin and deprotected. Suitable resins, protecting groups, condensation reagents and reaction conditions are well known in the art.

The invention relates also to DNAs coding for a compound of formula I or II, to mutants thereof, e.g. DNAs wherein one or more, especially one, two, three or four, nucleotides are mutated, and to fragments of such DNA comprising at least 15 nucleotides. It is understood that such DNAs are single-stranded or double-stranded.

In particular, the invention concerns a DNA coding for MRP-8 of the formula $$Y_1-Y^M-Y^L-Y^T-Y^B-Y^L-Y^B-Y^K-Y^A-Y^L-Y^N-Y^S-Y^I-Y^I-Y^D-Y^V-Y^T-Y^H-Y^K-Y^Y- \quad \text{(III)}$$

$$Y^S-Y^L-Y^I-Y^K-Y^G-Y^N-Y^F-Y^H-Y^A-Y^V-Y^Y-Y^R-Y^D-Y^D-Y^L-Y^K-Y^K-Y^L-Y^L-Y^B-$$

$$Y^T-Y^B-Y^C-Y^F-Y^Q-Y^Y-Y^I-Y^R-Y^K-Y^K-Y^G-Y^A-Y^D-Y^V-Y^W-Y^F-Y^K-Y^B-Y^L-Y^D-$$

$$Y^I-Y^N-Y^T-Y^D-Y^G-Y^A-Y^V-Y^N-Y^F-Y^Q-Y^B-Y^F-Y^L-Y^I-Y^L-Y^V-Y^I-Y^K-Y^M-Y^G-$$

$$Y^V-Y^A-Y^A-Y^H-Y^K-Y^S-Y^H-Y^B-Y^B-Y^S-Y^H-Y^K-Y^B-Y^*-Y_3,$$

and a DNA coding for MRP-14 or of the formula $$Y_1-Y_2-Y^M-Y^S-Y^Q-Y^L-Y^B-Y^R-Y^N-Y^I-Y^B-Y^T-Y^I-Y^I-Y^N-Y^T-Y^F-Y^H-Y^Q-Y^Y-Y^S- \quad \text{(IV)}$$

$$Y^V-Y^K-Y^L-Y^G-Y^H-Y^P-Y^D-Y^T-Y^L-Y^N-Y^Q-Y^G-Y^B-Y^F-Y^K-Y^B-Y^L-Y^V-Y^R-Y^K-Y^D-$$

$$Y^L-Y^Q-Y^N-Y^F-Y^L-Y^K-Y^K-Y^B-Y^N-Y^K-Y^N-Y^B-Y^K-Y^V-Y^I-Y^B-Y^H-Y^I-Y^M-Y^B-Y^D-$$

$$Y^L-Y^D-Y^T-Y^N-Y^A-Y^D-Y^K-Y^Q-Y^L-Y^S-Y^F-Y^B-Y^B-Y^F-Y^I-Y^M-Y^L-Y^M-Y^A-Y^R-Y^L-$$

$$Y^T-Y^W-Y^A-Y^S-Y^H-Y^B-Y^K-Y^M-Y^H-Y^B-Y^G-Y^D-Y^B-Y^G-Y^P-Y^G-Y^H-Y^H-Y^H-Y^K-Y^P-$$

$$Y^G-Y^L-Y^G-Y^B-Y^G-Y^T-Y^P-Y^*-Y_3,$$

wherein $Y_1$ is a flanking DNA residue of 12 nucleotides or more containing a promoter sequence, $Y_2$ is $Y^M$—$Y^T$—$Y^C$—$Y^K$ or absent, $Y_3$ is a flanking DNA residue of one or more nucleotides or absent, $Y^A$ codes for alanine (A or Ala) and is GCT, GCC, GCA or GCG, $Y^C$ codes for cysteine (C or Cys) and is TGT or TGC, $Y^D$ codes for aspartic acid (D or Asp) and is GAT or GAC, $Y^E$ codes for glutamic acid (E or Glu) and is GAA or GAG, $Y^F$ codes for phenylalanine (F or Phe) and is TTT or TTC, $Y^G$ codes for glycine (G or Gly) and is GGT, GGC, GGA or GGG, $Y^H$ codes for histidine (H or His) and is CAT or CAC, $Y^I$ codes for isoleucine (I or Ile) and is ATT, ATC or ATA, $Y^K$ codes for lysine (K or Lys) and is AAA or AAG, $Y^L$ codes for leucine (L or Leu) and is TTA, TTG, CTT, CTC, CTA or CTG, $Y^M$ codes for methionine (M or Met) and is ATG, $Y^N$ codes for asparagine (N or Asn) and is AAT or AAC, $Y^P$ codes for proline (P or Pro) and is CCT, CCC, CCA or CCG, $Y^Q$ codes for glutamine (Q or Gln) and is CAA or CAG, $Y^R$ codes for arginine (R or Arg) and is CGT, CGC, CGA, CGG, AGA or AGG, $Y^S$ codes for serine (S or Ser) and is TCT, TCC, TCA, TCG, AGT or AGC, $Y^T$ codes for threonine (T or Thr) and is ACT, ACC, ACA or ACG, $Y^V$ codes for valine (V or Val) and is GTT, GTC, GTA or GTG, $Y^W$ codes for tryptophan (W or Trp) and is TGG, $Y^Y$ codes for tyrosine (Y or Tyr) and is TAT or TAC, and $Y^*$ is a stop codon TAA, TAG or TGA, a double-stranded DNA consisting of a DNA of formula III or IV and of a complementary DNA thereto, wherein adenine (A) combines with thymine (T) and vice versa, and guanine (G) combines with cytosine (C) and vice versa, that complementary DNA itself, genomic DNA, wherein one or more, especially one or two, introns interrupt the DNA of formula III or IV, a mutant of such DNAs, wherein one or more, especially one, two, three or four nucleotides are mutated, and fragments of such DNAs comprising at least 15 nucleotides.

Especially, the invention relates to a DNA coding for MRP-8 of the formula

```
                          10
       M  L  T  E  L  E  K  A  L  N  S  I  I  D  V  Y  H  K  Y            (V)
Y₁—ATGTTGACCGAGCTGGAGAAAGCCTTGAACTCTATCATCGACGTCTACCACAAGTAC
       10         20         30         40         50

20                       30
  S  L  I  K  G  N  F  H  A  V  Y  R  D  D  L  K  K  L  L  E
  TCCCTGATAAAGGGGAATTTCCATGCCGTCTACAGGGATGACCTGAAGAAATTGCTAGAG
       60         70         80         90        100        110

40                       50
  T  E  C  P  Q  Y  I  R  K  K  G  A  D  V  W  F  K  E  L  D
  ACCGAGTGTCCTCAGTATATCAGGAAAAAGGGTCCAGACGTCTGGTTCAAAGAGTTGGAT
      120        130        140        150        160        170

60                       70
  I  N  T  D  G  A  V  N  F  Q  E  F  L  I  L  V  I  K  M  G
  ATCAACACTGATGGTGCAGTTAACTTCCAGGAGTTCCTCATTCTGGTGATAAAGATGGGC
      180        190        200        210        220        230

80                       90
  V  A  A  H  K  K  S  H  E  E  S  H  K  E  *
  GTGGCAGCCCACAAAAAAAGCCATGAAGAAAGCCACAAAGAGTAG—Y₃,
      240        250        260        270        280
``` and a DNA coding for MRP-14 of the formula

```
          5              10                              20
          M  S  Q  L  E  R  N  I  E  T  I  I  N  T  F  H  Q  Y            (VI)
Y₁—Y₂—ATGTCGCAGCTGGAACGCAACATAGAGACCATCATCAACACCTTCCACCAATAC
            10         20         30         40         50

30                              40
  S  V  K  L  G  H  P  D  T  L  N  Q  G  E  F  K  E  L  V  R
  TCTGTGAAGCTGGGGCACCCAGACACCCTGAACCAGGGGGAATTCAAAGAGCTGGTGCGA
       60         70         80         90        100        110

50                              60
  K  D  L  Q  N  F  L  K  K  E  N  K  N  E  K  V  I  E  H  I
  AAAGATCTGCAAAATTTTCTCAAGAAGGAGAATAAGAATGAAAAGGTCATAGAACACATC
      120        130        140        150        160        170

70                              80
  M  E  D  L  D  T  N  A  D  K  Q  L  S  F  E  E  F  I  M  L
  ATGGAGGACCTGGACACAAATGCAGACAAGCAGCTGAGCTTCGAGGAGTTCATCATGCTG
      180        190        200        210        220        230
```

```
                                  90                                    100
            M   A   R   L   T   W   A   S   H   E   K   M   H   E   G   D   E   G   P   G
            ATGGCGAGGCTAACCTGGGCCTCCCACGAGAAGATGCACGAGGGTGACGAGGGCCCTGGC
               240         250         260         270         280         290
                                         110
          H   H   H   K   P   G   L   G   E   G   T   P   *
          CACCACCATAAGCCAGGCCTCGGGGGAGGGCACCCCCTAA—Y₃,
            300         310         320         330
``` wherein

- $Y_1$ is a flanking DNA residue of 12 nucleotides or more containing a promoter sequence, $Y_2$ is ATGACTTG-CAAA or absent and $Y_3$ is a flanking DNA residue of one or more nucleotides or absent,
- a double-stranded DNA consisting of a DNA of formula V or VI and of a complementary DNA thereto, that complementary DNA itself, genomic DNA, wherein one or more, especially one or two, introns interrupt the DNA of formula V or VI, a mutant of such DNAs, wherein one or more, especially one, two, three or four nucleotides are mutated, and fragments of such DNAs comprising at least 15 nucleotides.

The invention relates also to a DNA which hybridizes with a DNA of formula V or VI or with a DNA complementary to the DNA of formula V or VI.

An example of a DNA of the invention of the formula V coding for MRP-8 is e.g. the cDNA which is derived from mRNA of a human mononuclear leukocyte, of the formula Other particular cDNAs derived from mRNAs of human mononuclear leukocytes differ in the meaning of $Y_1$ (nucleotides 1 to 123 in formula VII). $Y_1$ is e.g. AAGTCTGTGGGCATC-, ATGTCTCTTGTCAGCTGTCTTTCAGAAGACCTGGT-GGGGCAAGTTCCGTGGGCATC-, TTGTCTCTTGTCAGCTGTCTTTCAGAAGACCTGAA-GGTTCTGTTTTTCAGGTGGGGCAAGTTCCGTGGG-CATC- or a sequence comprising nucleotides 108 to 123 or 86 to 123 of formula VII with an insert of a T between nucleotides 112 and 113.

A further example of a DNA of the formula V coding for MRP-8 is e.g. the genomic DNA which is isolated from human placenta and which contains an intron of 150 nucleotides between the amino acids 47 and 48 (nucleotides 141 and 142 of formula V), of the formula

```
AACTTGGAACAGCCCTTCTACATACACTCCATCTTCTCTATCTTAGTTACAAGTTTTTT        (VII)
      10        20        30        40        50        60

AATAAGAAATGGGCAAAGTCAGCTGTCTTTCAGAAGACCTGGTGGGGCAAGTCCGTGGGC
     70        80        90       100       110       120
                                10
           M   L   T   E   L   E   K   A   L   N   S   I   I   D   V   Y   H   K   Y
           ATCATGTTGACCGAGCTGGAGAAAGCCTTGAACTCTATCATCGACGTCTACCACAAGTAC
             130       140       150       160       170       180
      20                                30
       S   L   I   K   G   N   F   H   A   V   Y   R   D   D   L   K   K   L   L   E
       TCCCTGATAAAGGGGAATTTCCATGCCGTCTACAGGGATGACCTGAAGAAATTGCTAGAG
             190       200       210       220       230       240
  40                                  50
   T   E   C   P   Q   Y   I   R   K   K   G   A   D   V   W   F   K   E   L   D
   ACCGAGTGTCCTCAGTATATCAGGAAAAAGGGTGCAGACGTCTGGTTCAAAGAGTTGGAT
         250       260       270       280       290       300
  60                                  70
   I   N   T   D   G   A   V   N   F   Q   E   F   L   I   L   V   I   K   M   G
   ATCAACACTGATGGTGCAGTTAACTTCCAGGAGTTCCTCATTCTGGTGATAAAGATGGC
         310       320       330       340       350       360
  80                            90
   V   A   A   H   K   K   S   H   E   E   S   H   K   E   *
   GTGGCAGCCCACAAAAAAAGCCATGAAGAAAGCCACAAAGAGTAGCTGAGTTACTGGGCC
         370       380       390       400       410       420

CAGAGGCTGGGCCCCTGGACATGTACCTGCAGAATAATAAAGTCATCAATACCTCAAAAA
      430       440       450       460       470       480

AAAAA.
```

(VIII)

```
                                                                                                CTGGGTTGC    -1501
TTCCACCTTTTGGCTCTTGTAAATAATGCTGTATGAACATGAATGTACAAACATCTGTTTGAATCCCTGCATTCAATTCTTTGCATATACCAGGA            -1401
GCAGAATGATGATCATATGGTAATTCTGTGTTTATTATTGAGGAACAAACTTGCCGTTTTCATAACAGCTGCACTATTTACATTCCCACTAACAG            -1301
TGCATTAGGCTTCCAATTCTCTATGCCCTCACCAACACTTGTTTTCTGGGTTTAAAAGAAGTAGTCATCCTTGTAGGTGTCAGGTGGTATCTCATT          -1201
GTCGTTTGCTTCATGTTTCCTAAAGATTAGTAATTTCATATGCTTATTGACCATTTGTATATCTCTCTGGAGAAGTGTCTATTTGAGTCTTTCCCC          -1101
AATTTTGATTGGTTGTTGTTTTGTTGTGAGTTGTAGGGATTCTTTATATTCTGGATATTAATCCCTTATCAGATATTTGTTTTACAAATATTT            -1001
CTTTGTAACAGAAACACACCACAGTCTTCAAGGTTGAAGCCAGTTAATCTGAGTAGCATTTGTTAGTGGTGGGAGAGGATTTGTTCCTCCTGAA            -901
ATCCTGGGAATTGGCCACCTCCTCTTCTGGGGTCCCAGACACAATAATTAACCAAGAGAGGGTGAAAGGCTCCCTGTGTTTATGCAATGGCTCAGGCCCTTGTGA  -801
TCTCTTCAGCCAGTGATCCTGGGAACCCCAAGCAGCCTCCATCTCCAGGGCATGCTGTCCAGCTTTCACAGAACAGGAAAGCTGTGGAGGAGTGTGGCCAGGGTA  -701
AGTGCCGAGGGACCCCAAGCAGCCTCCATCTCCAGGGCATGCTGTCCAGCTTTCACAGAACAGGAAAGCTGTGGAGGAGTGTGGCCAGGGTA              -601
GGAATGGATATAGCCCTTGGCAACAACACATTTCCCACAAAGCACCACCAAAAGAACAACGATAGTTTAGTTTTTAGTAATGAACAATAGT              -501
TCTCATGACTAAAAGCCATCAGCCAGGAAGCTGTTCTCAACCCTTTGCGTCTTTGAAACCTCTGACAGAAGCCATGAGGAATGTTCTCA                -401
CTGAGTGCATGCACTCAAAATGATGCATTCAACTTCAGTTTCAGGGATGTATGGCCTGACCAATGCAGGGATTAGCAATCGCAATAGTGGA              -301
GAGGGCATGGGAGTGGGAATCTGGCTGAATCAAGCAAGTGAATGCCAGCAAGCCCAGAAAAAGAGCCCCTGCTTTTCCTCCTGGGCACTATTG            -201
CCCAGCAAATGCCTTCCTCCTCTTCCGGCTTCCTACCTCCCACCCCCAAAATTTCATTCTGCACGTGATTGCCACATTCACTGTTGAGAAACAGAGACT      -101
GTAGCAACTCTCTGGAGAGAAGAGCTGTCTCTGATGCCTGAAGCTGTGGGCAGCTGCCAAGCCTAACCGCTATAAAAGGAGCTGCCTCTCAGCCCTGC        -1
```

```
Exon 1
ATGTCTCTTGTCAGCTGTCTTTCAGAAGAGACCTG GTAAGTGGGACTGTCTGGGTTGGCCCCGACACTTTGGGCTTCTCTTGGGAGGGTCTTGGGGAAGTGGAG   100
CAGCCTTCCTGAGAGAGGAGAGAGAAGCTCAGGAGGTCTGAGCAAAGATACTCCTGGAGGTGGGAGTGAGGCAGGGATAAGGAGGATAAGGAGAGAGTATCCT   200
```

-continued

```
CCAGCACCTTCCAGTGGGTAAGGGCACACATTGTCTCCTAGGCTGGACTTTTTCTTGAGCAGAGGGTGGGGTGGTGGAGAGGTGGTAAGGAAAAGTCTACGGGGCCCCCGTGTGTG    300

TGCACATGTCTCTGTGAATGACCTTCCCCACACGTGTATCCCTATCATCCCTGCGTACTGCCTGGGGCATGCGCTTGGAGACCTGCAGGAGACCAGTGGGGCGGCGTTGGT    400

TATTTGAGAGTGCAGGCCAGGACAAGGCCATCGCTTGGGGCATGAATCCTCTGCGTACTGCCCTGGTCAGATGAACATGGCCTGACACTGTTGACGGTCTATCATCAGG    500

M  L  T  E  L  E  K  A  L  N  S  I  I  D  V  Y  H  K  Y  S
                      Exon 2                       1                                  10                       20
AAGGTTCTGTTTTTCAG GTGGGGCAAGTTCCGTGGGCATCATGTTGACCGAGTGCAGGAGCCTGCATCATCGACGTCTACCACAAGTACTCC    600

L  I  K  G  N  F  H  A  V  Y  R  D  D  L  K  K  L  L  E  T  E  C  P  Q  Y  I  R
                       30                                    40
CTGATAAAGGGGAATTTCCATGCCGTCTACAGGGATGACCTGAAGAAATTGCTAGAGACCGAGTGTCCTCAGTATATCAGG GTGAGGAGGGGCTGGGTGT    700

GGCGGGGCTCTCTGCCCTGGTCCTGCCCAGCCGTCCTGGGGCTGAGGCTGTCTGCCCCTTCATAGATGTATGCCTCGGCTCTCTCTGAGATCTTTAA    800

K  K  G  A  D  V  W  F  K  E  L  D  I  N  T  D  G  A  V  N  F  Q  E
                                 50                                  60                                 70
ACTCTCGGCTTTCTCCTCCCTCAATCTTGACAG AAAAAGGGTGCAGACGTCTGGTTCAAAGAGTTGGATATCAACACTGATGGTGCAGTTAACTTCCAGGAG    900

F  L  L  V  I  K  M  G  V  A  A  H  K  K  S  H  E  E  S  H  K  E  *  Exon 3
                  80                                 90
TTCCTCATTCGGTGATAAAGATGGGCGTGGCAGCCACAAAAAGAGCCATGAGGAAAGTCACAAAGAG  ATGCCTCTCTCTTATGCTTTTGTGAATGAGGTTTCCGGTGTGGAGGGAGGGTTGGA    1000

AAACCCAAAGGAAGAAAAAGAAATCTATGTTATCCCACCTCTACCTCTCACAAGCCTTTCACCCCTGCTGCCCCACATTCCTTCA    1100

GCCCCTCATTCGAGCATTGGAGGCTTAAGGATTCAAAAGTCGTCATGAATATAGCTAAATCTTAGCTTCCAGTGAGAGAGACAGAAAGAGCAAGAGAGGGG    1200

TGGGAACAGGGTGGTAGTATAGAAGTGTGTGGTGTGTGTGTCTGTGTCTGTGTGTCTGTGTGAGAGAGACAGAAAGAGCAAGAGAGGAAGGGGGG    1300

GTGATAGCTACATAGAAGTGTGTGTGTGATGTAGGTGGACAATGTTCAGAGTGCTCCATTAACAGGATAATCCTCACACCTGTCCACATAGGAAATAGTAGA    1400

AGAGGCTGATTGTGTGTGTGATGTAGGTGGACAATGTTCAGAGTGCTCCACTCCCAACTCAATTAAATGATAAAATATCTAAAAATACTTCCAAGGGGG    1500

CTTGGGGATTTGAAAATTTCTCCTCCTCTCCACTCCAACTCAATTAAATGATAAAATATCTAAAAATACTTCCAAGGGGCTGTCCACATAGGAAATAGTAGA    1600

TTAAGTCAAAGATAGGTTATTCATACGCTGCCTATGGGATTCTATGCTTTGATCAGAAAAATATTAAAAATACTTCCAAGGGGCTGTAGGAGGG    1700

AGCCAGAAGAGACGAGTGGTTCTCTCTGAGGTGGACATTAAAAAGAGAAAATGAGGGGAACCTTTTGACAAGAATGTCACCCAACTGATTTTC    1800

1900
```

-continued

ATGCTGTGTGTGGGGAATTTTCTGTTGTCCTCACTTAGGTGCTGGGGCAGTGGTGTTAGTGATGGGTAAAAAGGTAGGAAGCTGTCACAGAATCACTAA 2000

ACCAGGGTTCTTAACTTGTCTGTCTATACATCTCTGAAATTGGGTTGAAGTTGTGTGCATCATTTTGAGTGACGCACTGAGAACATTCCTCCACGGCTTC 2100

CATCGAGAGTCTCGAAAAGGCCCAACACCTCAAAAAGGTTAAGAACACTTGTCCTGCTTACTGGTTTTTAGTAACAAATGGCAGAGTATTTCTCTCTGTC 2200

TCTCTCTCTTTTTTTTTTGAGACACAGGGTCTTGTCTGTCACGTGACTAGAGTACAATGGGCATGATCATGGCTCACTGTAGCCTCGAA 2300

CACCTGGGCTCAAGTAATCCTCCCACCTCAGCCTCTTTAGTAGCTGGGACTACAGCATGAGCCACTGCCCTTGGCTAATTTTTAAATTATTTTTTGTAG 2400

AGATGGAAACTTGCTATGTTGCCCAGGCTAGTCTCAAACTCCTGACTCAAGCGATCCTCCTACCTTGGCCTCCCAAAGTGCTGAGATTACAGTGTGATC 2500

CACACCACACCTGGCCAAAGATTGGAGTATTTTATTGCTATTGTTGTGCTGGGTGGGTGGGTGTATGCTTTGTGGGGACGTGTGTTGTTGCCAAG 2600

GGCTAAATCAGTTCCTACCCTGCTGCCCACAGTCCTCCACAGCTTCCTGCTCTGTGAAGCTAAGGATACACCCCGATGATAAGCTGTCAACATA. 2695

An example of a DNA of the invention of the formula VI coding for MRP-14 is e.g. the cDNA which is derived from mRNA of a human mononuclear leykocyte, of the formula

```
                                                      1
                                                      M  T  C  K  M  S           (IX)
         AAAACACTCTGTGTGGCTCCTCGGCTTTGACAGAGTGCAACAGCATGACTTGCAAAATGTCG
              10        20        30        40        50        60

10                                   20
     Q  L  E  R  N  I  E  T  I  I  N  T  F  H  Q  Y  S  V  K  L
     CAGCTGGAACGCAACATAGAGACCATCATCAACACCTTCCACCAATACTCTGTGAAGCTG
         70        80        90        100       110       120

30                              40
  G  H  P  D  T  L  N  Q  G  E  F  K  E  L  V  R  K  D  L  Q
  GGGCACCCAGACACCCTGAACCAGGGGGAATTCAAAGAGCTGGTGCGAAAAGATCTGCAA
        130       140       150       160       170       180

50                              60
  N  F  L  K  K  E  N  K  N  E  K  V  I  E  H  I  M  E  D  L
  AATTTTCTCAAGAAGAAGAATAAGAATGAAAAGGTCATAGAACACATCATGGAGGACCTG
        190       200       210       220       230       240

70                              80
  D  T  N  A  D  K  Q  L  S  F  E  E  F  I  M  L  M  A  R  L
  GACACAAATGCAGACAAGCAGCTGAGCTTCGAGGAGTTCATCATGGTGATGGCGAGGCTA
        250       260       270       280       290       300

90                              100
  T  W  A  S  H  E  K  M  H  E  G  D  E  G  P  G  H  H  H  K
  ACCTGGGCCTCCCACGAGAAGATGCACGAGGGTGACGAGGGCCCTGGCCACCACCATAAG
        310       320       330       340       350       360

110
  P  G  L  G  E  G  T  P  *
  CCAGGCCTCGGGGAGGGCACCCCCTAAGACCACAGTGGCCAAGATCACAGTGGCCACGGC
        370       380       390       400       410       420

CACGGCCACAGTCATGGTGGCCACGGCCACAGCCACCCAT.
        430       440       450       460
```

A further example of a DNA of the formula VI coding for MRP-14 is e.g. the genomic DNA which is isolated from human placenta or fetal liver cells and which contains an intron between the amino acids 50 and 51 (nucleotides 138 and 139 of formula VI) of the formula

```
-901  ATCACTGTGGAGTAGGGGAAGGGCACTCCTGGGGTGGCAAGGTGGGAGGTAGTGAAAGGGAAGCTGGC
-801  CGGACAGGAAGGGCCATTCCAAGAGGGCTTTGTGCGCAGGGCTAAGCCAAGCAACTGGAGGTTCGTAGCAGGAGAAG
-701  GACACATCAAGCCACCAGGAGGCTAAGTAAAACAGTTGTCTCCAAGTTCCTGGAACCCTTGCTAGAAAAATGATGCT
-601  GAGAGATGCTAGAAACATATTCGCCCTGAGGCTCTCACTCAGACTGACCTATGTGACCTTGCAAGAGGAAGGTATCATCAGAACTGG
-501  GTCCCCTTCCTGCCAAGTCAGCCAACCAGCTATGTGACCTTGCCAGTTCTTCATCTACAATGCAAGAGGGTTGCCACCT
-401  CTGAGAACCCTCTAACCCCAAATCTCACCCTATGAATCTAAGAACACAACCCCTGCCATCCTAAGTATCACAGAGCT
-301  CAGACCATCCTGTTGGACTAAAAGGAAGGGCAGACTGCCATGGGGGCAGGGGTCAGCCGAGAGGCTCAGCCTCAAA
-201  GGGGATGGGGGCTGAGTGGTGCCAGGAGCAGCAGGCTCGCTCGGGAGTAGGGCCTTAGGATAGAAGGGAAATGAACTAAACAGCTTCCTC
-101  CAAACCAGTTTCAGGCCAGGGCTGGGAATTTCACAAAAAGCAGAAGGCCAAGTGCCCCCAGCCTCTGGCAGTTAC
  -1  CACACTGCTCACCTGTGAAGCAATCTTCCGGAGAACAGGCCAAGTGCCCCCAGTCAGGAGGAGCTGCCAGCAGCTCTGGC

┌──── Exon 1 ─────────────
 100                                                    │AAACACTCTGTGTGCCTCGGCTTTG│ GTAAGTGAGTCGCCAGCTTCCCCAGGCAGAAGCCTGCCTGCCGATTCCTTCTTCCTGACCAACTT
 200  CCTTCCAAATCTCCTCCTAGAGAAGCCCTCTGGTTGGCCCTGCCTACTTTAAAGTCATTTGTACATGTGTGACAGGCCATCTCCCAGTTAAGTGCAGCCTGTGCT
 300  CCTCAAATGCTTTTTGCACTCTGTAGATATTCTAAAAATCATTTGTAGGAGTGCTTAGTGAGTGTCAAGAAGTCAAAGAAGCTGAAAGATCTGCAAATTTCTCAAG
                                               M  T  C  K  M  S  Q  L  E  R  N  I  E  T  I  I  N  T  F  H  Q  Y  S
                                                                                10                        20
 400  TTCTTTTTATTTGCACTTCCCCACTATTTCTGTGAGTGCTTAGTGAGTGTCAAGAAGTCAAAGAAGCTGAAAGATCTGCAAATTTCTCAAG │GTAGGGGCTGGACTCTGGCAG
       V  K  L  G  H  P  D  T  L  N  Q  G  E  F  K  E  L  V  R  K  D  L  Q  N  F  L  K
                      30                        40                        50
                ┌──── Exon 2 ─────────────────────────────────────────────────────────
 500  TGAAGCTGGGGCACCCGAGACACCCTGAACCAGGGGGAATTCAAAGAGCTGGTGCGAAAAGATCTGCAAAATTTTCTCAAG│GTAGGGGCTGGACTCTGGCAG
 600  
```

```
                                                                               -continued
GTCTGACCCAGCCTCACCCGCAGTTTGGGTTGACAAGGGAGGATGGGAGTATGGGCTACAGGACGACAGGGTAAGCAATCAAGGGGAAGATTTGAGCTCCTGGAGCCCAGCCCCA        700
AGACGCAGCGAGTGTCCCTGTGTTATACAGGGCAGGTGCTCACAGTTACACAGGACGACAGGGTCAAGAAATTGCTCAATTGAACACCTGCTATTTGTCGGGC                   800
CCTGTTCTGGGCAGAGGGATGTAGTGGTAAATGGGAGCCCACTATTCCATGAGGAGACACAGTAAAGTTGTTGGCCAATAAAGAGCACAGATAAAGCC                         900
AAATGCCAATAAGTGCCTGGAAGAAATGAGATAGAGTGCGCTGTGGGCAATGGGGCTGGTGGGGTGACCAGTTAGGGTACATGAGAAGGGCC                              1000
TCTTTGAGGAGGTAACATTTGAGCTGAGCCCCGATGTTGGGGAGGAAGCCCTGAGGATGACACAAAGTGAGGAGACCCTAAGCCTCAGG                                 1100
GCGAACTTGGGGTGGAAGACTTGGGGCTTTTCTAATCCTAAGGGTCTGCGGGTGAAATGAATAAAGAGCACATGGAGCCTGCACAGCACT                                1200
CAGGGAACTGGGAGGTTTTTCCCCGCTCCAAAAATGATTAGGCAGTTCTAAGAAAAAGGCTGAGCACTTCCAACAGCTCCAACAGCCTTTTGTTTCTTTTCAAATT               1300
TGGGGAAAGTCGGGAACAGAGGCCTGCATTAAGAACATGGTTCTGCAGTCTCAGTCTGAGTTAGGGCCCTGACAGCTCTCCAGTCCCCGGAGCCAGACATCCTGGGGTAGGTCC       1400
CCAGCCCCTCCCAGTGCCCCTCCCTCCGCTTGGTAAGGTGGGAAGAAAGGGCCTTCAGACTTAGGGGCCTGTAAGGTGGAGGCCTCAGG                                 1500
CAGGCAGGATGCTGGGTGGGTAGGCAAGAAGCCCAGCAGAGGCCATCGGAAAACTATCCTCCACAGCCTCATGTGACCCCGCTTCACCCCCC                              1600
ACCTGACATCCCCCACCAGAAGCAAAGCGATGCTGTGGGAAGACAGAGCCTCATGGATGGGCTGCACAGGAGTGCTCGCATTGGCTGGGTACCC                            1700
CACAGGTTCTGGAGGGGACTTAGCGAGGTGACTCAG----------------------360 NT----------------------------TGC                           2100
CTCGGCCTCCCAAAGTGCTGGGATTACAAGCATGAGCCACCCTGTCCGACCATCTCCCCTTTATACTTTATCACACCCTGAGGTCAGCGGAGCACATA                        2200
CTCTGCTCTCTGACCCTCCATCCCCCTGCCACACCTAGGTTTTTCTAGTGTTCCCCGTTGTATTGGTTGAAATAAGTTCACTAATTGTAACCTCC                           2300
AGAGGGAAGGGAAGGGAGGGCAGGGAAGGAGTGCAGGGTAGCAGAGTGGAACTGGCTCTAAGTCAGATCTGAATTTGCATGCCCTCAATA                                2400
GTCAAGCCTGTGAAAACTAATGACCCTCTCTAGGACTGGTTTCAAGTCTTCCTCCAGGAAGATACCATTCCTAGCTGTTAAAGTTGTTATAAGGACCAAA                     2500
TGAGGTGACATTTCCAGGCTTACTCATGCCAAGGCAAGACCCTGGAACTCAGCTCTCCATTGCGCACCTAGCCTATGGTCATTTTAATCCAGCC                            2600
GTCATGGAGGAATAAACTGGAGAGCGTTTGGTATGTGCTCAGTGTCAGTGGCTGGTCATTACTGTGCTCCCAGTCCCCACCCCGGCACCACCCTCTCACAGCC                   2700
CCAGGGTCGAGGCTTCCTTGTACATTTGCCAGTCGGTCATTGCCAGCTGGCTCCCGTCCCCACCCTCTGGCCACCACCCCCAGCTCTCACAGCCTCTCTCCCCA                  2800
```

```
                    K  E  N  K  N  E  K  V  I  E  H  I  M  E  D  L  D  T  N  A  D  K  Q  L  S  F  E  E  F  I  M
                    51                          60                             70                          80
CCCGCAG AAGGAGAGAATAAGAATGAAAAGGTCATAGAACACATCATGGAGGACCTGGACACAAATGCAGACAAGCAGCTGAGCTTCGAGGAGTTCATCATG   2900

L  M  A  R  L  T  W  A  S  H  E  K  M  H  E  G  D  E  G  P  G  H  H  K  P  G  L  G  E  G  T  P
                         90                             100                           110
CTGATGGCGAGGCTAACCTGGGCCTCCCACGAGAAGATGCACGAGGGTGACGAGGGCCCTGGCCACCACAAGCCAGGCCTCGGGGAGGGCACCCCT   3000

*Exon 3
AAGACCACAGTGGCCAAGATCACAGTGGCCACGGCCACGGGCCACGGTCATGTGGCCACAGGCCACTAATCAGGAGGCCAGGCCACCCTGCCTC   3100

TACCCAACCAGGCCCCGGGGCTGTGTATGTCAAACTGTCTTGGCTGTGTGGGGCTAGGGGCTGGGGCAAATAAAGTCTCTTCCTCCAA GTCAGTGCTCTGTG   3200

TGCTTCTTCCACCTCTTCTCCAAGGCTCTGGCCTTAGACAGCCCTGTCCTTATCTGTGACTCAGCCCCTCATTCAGTATTAACA   3300

AAATGAGAAGCAGCAAAACATGGGTCTGTGCTAGGCCTCACCTCCCTGACCATGTCCTCACCTCTGACTTCAGGCCCCACTGTTCAGATCCCA   3400

GGCTCCCTGCCCATCTCAGACACCCTGTCCCAGCCTGTCCAGCCTGTCTTCACCCATCACTACTGTCACTGTACACTGTAGAAAGCAAAAAGGCATATCTACC   3500

CCTTGATATGCCTGCTACCTCACCAGCCCTCTTCTCCTAACAGAATTCGGTGTGTTATCTCACATTCCTCT   3600

GAAAGTCTTCAGAAACTGGACCTAGATAGTGCCACCCTGCCACCCTAATCAACCGAGTGCTCACCAAGTGGGAGTCTGAGAGCTTAGCCCTATGCCACCCTGG   3700

GATCAGAGAGCATGATCTCTCTTAACAGACCTGCCACCCTAATCAACGGAGTGCTCACCAAGTGGGAGTCTGAGAGCTTAGCCCTATGCCACCCTGG   3800

TCTCAACAGAATGGCAGAGTGAAGAAATGAGCTCCAGTCCGGGCTCTGCAG   3851
```

Furthermore, the invention relates also to RNAs coding for a compound of formula I or II, to mutants thereof, e.g. RNA wherein one or more nucleotides are mutated, and to fragments of such RNA, in particular to a RNA of the formula V or VI, wherein the various Y have the meanings given hereinbefore except that RNA residues replace DNA residues and hence uridine (U) replaces deoxy-thymidine (T), in particular to a RNA of formula VII or IX, wherein U replaces T.

The DNAs coding for a compound of formula I or II or for a mutant thereof and fragments of such DNAs or mutants can be prepared for example by culturing a transformed host and isolating the desired DNA therefrom, or by chemical synthesis through nucleotide condensation.

In particular, such DNAs can be prepared by a) isolating mRNA from human mononuclear leukocytes, selecting the desired mRNA, e.g. by hybridization with a DNA probe, preparing single-stranded DNA complementary to that mRNA, then double-stranded DNA therefrom (ds cDNA), or b) isolating genomic DNA from human cells, e.g. placenta or fetal liver cells, and selecting the desired DNA using a DNA probe, and c) incorporating ds cDNA of step a) or ds DNA of step b) into an appropriate expression vector, d) transforming an appropriate host with the obtained hybrid vector, e) selecting the transformed host which contains DNA coding for a compound of formula I or II, a mutant or fragment thereof from hosts containing no coding DNA, and f) isolating the desired DNA.

Polyadenylated messenger RNA is isolated from human mononuclear leukocytes by known methods. The leukocytes may be derived from fresh human blood, e.g. from buffy coats consisting of white blood corpuscules, or from leukocytes of an established continuous cell line which can be expanded in culture. Isolation methods involve, for example, homogenizing stimulated leukocytes in the presence of a detergent and a ribonuclease inhibitor, e.g. heparin, guanidinium isothiocyanate and mercaptoethanol, extracting the mRNA with suitable chloroform-phenol mixtures, optionally in the presence of salt and buffer solutions, detergents and/or cation chelating agents, and precipitating mRNA from the remaining aqueous, salt-containing phase with ethanol, isopropanol or the like. The isolated mRNA may be further purified by centrifuging in a cesium chloride gradient followed by ethanol precipitation and/or by chromatographic methods, e.g. affinity chromatography, for example chromatography on oligo(dT) cellulose or on oligo(U) sepharose. Preferably, such purified total mRNA is fractionated according to size by gradient centrifugation, e.g. in a linear sucrose gradient, or chromatography on suitable size fractionation columns, e.g. on agarose gels.

The desired mRNA is selected by screening with a DNA probe or by translation in suitable cells or cell-free systems and screening the obtained polypeptides.

Fractionated mRNA may be translated in cells, e.g. in frog oocytes, or in cell-free systems, e.g. in reticulocyte lysates or wheat germ extracts. The obtained polypeptides are screened for macrophage migration inhibitory activity or for reaction with antibodies raised against native macrophage migration inhibition factor (MIF), e.g. in an immunoassay, for example radioimmunoassay, enzyme immunoassay or immunoassay with fluorescent markers. Such immunoassays and the preparation of polyclonal and monoclonal antibodies are well known in the art and are applied accordingly. Monoclonal antibodies to MIF and immunoassays using them are described, e.g. in European Patent Application EP 162 812.

The selection of the desired mRNA is preferably achieved using a DNA hybridization probe, thereby avoiding the additional step of translation. Such hybridization probe may be a fully synthetic DNA consisting of at least 17 nucleotides or a DNA or DNA fragment isolated from a natural source or from a genetically engineered microorganism.

A synthetic DNA probe can be constructed on the basis of a partial amino acid sequence of a human MIF protein isolated from a natural source, e.g. the human MIF 8 kD described in EP 162 812 or a human MIF-related protein with molecular weight of approximatively 14 kD. Preferably mixtures of oligonucleotide comprising 17 or more nucleotides are prepared, wherein each member of the mixture is complementary to one fragment defined by six or more consecutive triplet codons Y of formula III or IV. Such DNA probes are also comprised by the present invention.

Examples for DNA probes of the invention are the 17-mer oligonucleotides complementary to the DNA fragments of formula $Y^D—Y^V—Y^Y—Y^H—Y^K$—TA corresponding to amino acids 14–19 of MRP-8 of formula I and of formula $Y^D—Y^V—Y^W—Y^F—Y^K$—GA corresponding to amino acids 52–57 of MRP-8 of formula I, and the 26-mer oligonucleotide mixture complementary to the DNA fragment of formula $Y^T—Y^I—Y^I—Y^N—Y^T—Y^F—Y^H—Y^Q$—TA corresponding to amino acids 14–22 of MRP-14 of formula II, in which formulas the meaning of $Y^D$, $Y^F$, $Y^H$, $Y^I$, $Y^K$, $Y^N$, $Y^Q$, $Y^T$, $Y^V$, $Y^W$ and $Y^Y$ is as defined under formula IV. The 26-mer oligonucleotides contain three inosine residues in place of a nucleotide complementary to a nucleotide of a triplet Y, thus reducing the number of complementary nucleotide-nucleotide interactions to 23.

The synthesis of such oligonucleotides is performed according to known methods as detailed hereinbelow, preferably by stepwise condensation using the solid phase phosphotriester, phosphite triester or phosphoramidite method, e.g. the condensation of dinucleotide coupling units by the phosphotriester method. These methods are adapted to the synthesis of mixtures of the desired oligonucleotides by using mixtures of two, three or four nucleotides dA, dC, dG and/or dT in protected form or the corresponding dinucleotide coupling units in the appropriate condensation step as described by Y. Ike et al. (Nucleic Acid Research, 1983, 11, 477).

The DNA probes have to contain a marker so that hybridization with the desired mRNA can be detected and the mRNA identified and separated from other mRNA not coding for a polypeptide of the present invention. Suitable are e.g. radioactive labels, such as $^{32}P$ in the 5'-end phosphate of the oligonucleotide, fluorescent markers or a label containing biotin which can be detected with suitably labelled avidin, e.g. avidin bearing a fluorescent marker or conjugated with an enzyme such as horseradish peroxidase.

Hybridization of size-fractionated mRNA with the DNA probes containing a marker is performed according to known procedures, i.e. in buffer and salt solutions containing adjuncts, e.g. calcium chelators, viscosity regulating compounds, proteins, irrelevant DNA and the like, at temperatures favoring selective hybridization, e.g. between 0° and 70° C., for example between 25° and 40° C. for the 17-mer oligonucleotides and between 30° and 50° C. for the 26-mer oligonucleotides, preferably at around 20° lower than the hybrid dsDNA melting temperature.

The preparation of a single-stranded complementary DNA from the selected mRNA template is well known in the art, as is the preparation of a double-stranded DNA from a single-stranded DNA. The mRNA template is incubated with a mix of deoxynucleoside triphosphates, optionally a radioactively labelled deoxynucleoside triphosphate (in order to be able to screen the result of the reaction), a primer sequence such as an oligo-dT residue hybridizing with the poly(A) tail of the messenger RNA and a suitable enzyme, e.g. a reverse transcriptase. After degradation of the template mRNA, the complementary DNA (cDNA) is incubated with a mix of deoxynucleoside triphosphates and a suitable enzyme as above to give a double-stranded DNA. Suitable enzymes are a reverse transcriptase, the Klenow fragment of E. coli DNA polymerase I or $T_4$ DNA polymerase. Optionally, the single-stranded DNA is first extended with a tail of like deoxynucleotides to allow the use of a primer sequence of complementary like deoxynucleotides, but the formation of dsDNA usually starts on spontaneous hairpin formation. Such dsDNA obtained as a result of hairpin formation is further processed with S1 nuclease which cuts the hairpin.

As an alternative to the preparation of cDNA from mRNA, genomic DNA may be isolated and screened for DNA coding for the desired polypeptide.

Genomic DNA is isolated from suitable human tissue, preferably from human placenta or human fetal liver cells, according to methods known in the art. A genomic DNA library is prepared therefrom by digestion with suitable restriction endonucleases, e.g. AluI and HaeIII, and incorporation into λ charon phage, e.g. λ charon 4A, following established procedures. The genomic DNA library replicated on nitrocellulose membranes is screened with a DNA probe, e.g. a synthetic DNA probe of at least 17 nucleotides or a cDNA derived from mRNA coding for the desired polypeptide, as described hereinbefore. When screening with a cDNA propagated in a suitable host microorganism, this cDNA is labelled e.g. by the well-known nick translation technique, then hybridized with the genomic DNA library in solutions containing salts and buffers and other adjuncts as described hereinbefore, preferably at temperatures between 40° and 80° C., e.g. around 65° C.

The incorporation of dsDNA prepared from mRNA or of genomic origin into an appropriate vector is well known in the art. For example, a suitable vector is cut and provided with tails of like deoxynucleotides. The dsDNA to be annealed then has to bear tails of complementary like deoxynucleotides, which is accomplished by incubation in the presence of the corresponding deoxynucleoside triphosphate and an enzyme such as terminal deoxynucleotidyl transferase. Otherwise, the dsDNA may be incorporated into the vector with the aid of linker oligodeoxynucleotides or else by blunt end ligation.

The transformation of an appropriate host with the obtained hybrid vector is well known in the art. For example, E. coli are conditioned for transformation by incubation in media containing calcium chloride, then treated with the hybrid vector. Transformed hosts are selected by a suitable marker, for example antibiotics resistance marker, e.g. tetracycline or ampicillin resistance.

The preparation of a DNA of the invention may also be performed by means of chemical synthesis. Suitable methods for the synthesis of DNA have been presented in summary form by S. A. Narang, Tetrahedron 1983, 39, 3. The known synthesis techniques allow the preparation of polynucleotides towards 40 bases in length, in good yield, high purity and in a relatively short time. Suitably protected nucleotides are linked with one another by the phosphodiester method [K. L. Agarwal et al., Angew. Chem. 1972, 84, 489], the more efficient phosphotriester method [C. B. Reese, Tetrahedron 1972, 34, 3143], phosphite triester method [R. L. Letsinger et al., J. Am. Chem. Soc. 1976, 98, 3655] or phosphoramidite method [S. L. Beaucage and M. H. Caruthers, Tetrahedron Letters 1981, 22, 1859]. Simplification of the synthesis of the oligonucleotides and polynucleotides is made possible by the solid phase method, in which the nucleotide chains are bound to a suitable polymer. H. Rink et al. [Nucleic Acids Research 1984, 12, 6369] use trinucleotides instead of individual nucleotides and link them by the phosphotriester method in the solid phase synthesis. A polynucleotide with up to 67 bases can thus be prepared in a short time and with good yields. The actual double-stranded DNA is built up enzymatically from chemically prepared overlapping oligonucleotides from both DNA strands, which are held together in the correct arrangement by base-pairing and are then chemically linked by the enzyme DNA ligase. Another possibility comprises incubating over-lapping single oligonucleotides from the two DNA strands in the presence of the four required deoxynucleoside triphosphates with a DNA polymerase, for example DNA polymerase I, the Klenow fragment of polymerase I or $T_4$ DNA polymerase, or with AMV (avian myeloblastosis virus) reverse transcriptase. The two oligonucleotides are thereby held together in the correct arrangement by base-pairing and are supplemented with the required nucleotides by the enzyme to give a complete double-stranded DNA [S. A. Narang et al., Anal. Biochem. 1982, 121, 356].

The invention further relates to hybrid vectors comprising a DNA coding for a compound of formula I or II, mutants thereof and fragments of such DNA operatively linked to an expression control sequence, and to processes for the preparation thereof.

The vector is selected depending on the host cells envisaged for transformation. Examples of suitable hosts are microorganisms, which are devoid of or poor in restriction enzymes or modification enzymes, such as yeasts, for example Saccharomyces cerevisiae, for example S. cerevisiae GRF 18, and strains of bacteria, in particular strains of Escherichia coli, for example E. coli X1776, E. coli HB 101, E. coli W3110, E. coli HB101/LM1035, E. coli JA221 or E. coli K12 strain 294, Bacillus subtilis, Bacillus stearothermophilus, Pseudomonas, Haemophilus, Streptococcus and others, and furthermore cells of higher organisms, in particular established human or animal cell lines, e.g. human embryonic lung fibroblasts L-132, human malignant melanoma Bowes cells, Hela cells, SV-40 virus transformed kidney cells of African green monkey COS-7 or chinese hamster ovary (CHO) cells. The above strains of E. coli, for example E. coli HB101, E. coli K12 and E. coli W3110, and of Saccharomyces cerevisiae, for example S. cerevisiae GRF 18, are preferred as hosts, furthermore the human embryonic lung fibroblast cell line L-132.

In principle, all vectors which replicate and express the desired polypeptide gene according to the invention in the chosen host are suitable. Examples of vectors which are suitable for the expression of the compounds of formula I or II in an E. coli strain are bacteriophages, for example derivatives of λ bacteriophages, or plasmids, such as, in particular, the plasmid ColE1 and its derivatives, for example pMB9, pSF2124, pBR317 or pBR322. The preferred vectors of the present invention are derived from plasmid pBR322. Suitable vectors contain a complete replicon and a marker gene, which allows to select and identify the hosts transformed with the expression plasmids on the basis of a phenotypical trait, and optionally signal sequences and enhancers. Suitable marker genes impart to the host, for example, resistance towards heavy metals, antibiotics and the like. Furthermore, preferred vectors of the present invention contain, outside the replicon and marker gene regions, recognition sequences for restriction endonucleases, so that the foreign DNA and, if appropriate, the expression control sequence can be inserted at these sites. The preferred vector, the plasmid pBR322 and derived plasmids, e.g. pUC9, pUC-KO, pHRi148 and pPLc24, contain an intact replicon, marker genes, which confer resistance e.g. towards tetracycline and ampicillin (tet$^R$ and amp$^R$), and a number of unique recognition sites for restriction endonucleases.

Several expression control sequences can be used for regulation of the gene expression. In particular, expression control sequences of highly expressed genes of the host to be transformed are used. In the case of pBR322 as the hybrid vector and *E. coli* as the host microorganism, for example, the expression control sequences (which contain, inter alia, the promoter and the ribosomal binding site) of the lactose operon, tryptophan operon, arabinose operon and the like, the β-lactamase gene, the corresponding sequences of the phage λ N gene, especially those containing the P$_L$ promoter, or the phage fd-coat protein gene and others are suitable. Whilst the plasmid pBR322 already contains the promoter of the β-lactamase gene (β-lac gene), the other expression control sequences must be introduced into the plasmid.

Vectors which are suitable for replication and expression in yeast contain a yeast replication start and a selective genetic marker for yeast. Hybrid vectors which contain a yeast replication start, for example chromosomal autonomously replicating segment (ars), are retained extrachromosomally within the yeast cell after the transformation and are replicated autonomously. Furthermore, hybrid vectors which contain sequences homologous to the yeast 2μ plasmid DNA can be used. Such hybrid vectors will get integrated by recombination into 2μ plasmids already existing within the cell, or replicate autonomously. 2μ sequences are particularly suitable for plasmids with a high transformation frequency and permit high copy numbers. The preferred yeast vector of the present invention is the plasmid pJDB207.

Suitable marker genes for yeasts are, in particular, those which impart antibiotic resistance to the host or, in the case of auxotrophic yeast mutants, genes which complement host lesions. Corresponding genes impart, for example, resistance towards the antibiotic cycloheximide or provide for protrophy in an auxotrophic yeast mutant, for example the URA3, LEU2, HIS3 or, in particular, TRP1 gene. Yeast hybrid vectors furthermore preferably contain a replication start and a marker gene for a bacterial host, in particular *E. coli*, so that the construction and cloning of the hybrid vectors and their intermediates can take place in a bacterial host.

Expression control sequences which are suitable for expression in yeast are, for example, those of highly expressed yeast genes. Thus, the promoters of the TRP1 gene, the ADHI or ADHII gene, acid phosphatase (PHO3 or PHO5) gene, isocytochrome gene or a promoter involved with the glycolytic pathway, such as the promoter of the enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, can be used.

Preferred vectors of the present invention contain promoters with transcriptional control, e.g. the promoters of the PHO5, ADH II and GAPDH genes, which can be turned on or off by variation of the growth conditions. For example, the PHO5 promoter can be repressed or derepressed solely by increasing or decreasing the concentration of inorganic phosphate in the medium.

Vectors suitable for replication and expression in mammalian cells are preferably provided with DNA from viral origin, e.g. from simian virus 40 (SV40), Rous sarcoma virus (RSV), adenovirus 2, bovine papilloma virus (BPV), papovavirus BK mutant (BKV), or mouse or human cytomegalovirus (CMV). Preferably, such vectors contain an origin of replication and an antibiotics resistance gene for propagation in *E. coli* together with an eukaryotic transcription regulatory sequence. In particular, such so-called shuttle vectors may be constructed from a pBR322 *E. coli* plasmid and SV40 and/or CMV enhancer and promoter regions. For example, the plasmid may contain the enhancer unit of the mouse or human cytomegalovirus major immediate-early gene, the SV40 enhancer combined with the human α-globin promoter, and/or in addition inducible promoters, such as the ones derived from the heat shock or metallothionein genes. Further it is also possible to utilize promoter or control sequences which are normally associated with the desired gene sequence. An origin of replication may be provided either by construction of the vector to include an exogeneous origin, such as derived from SV40, other viral source or provided by the host cell chromosomal replication mechanism. If the vector is integrated into the host cell chromosome, the latter method is often more efficient.

In a preferred embodiment, the present invention relates to hybrid vectors capable of replication and phenotypical selection in a host strain comprising a promoter and a DNA encoding a compound of formula I or II, a mutant or a fragment thereof, said DNA being positioned together with transcription start and termination signals as well as translation start and stop signals in said hybrid vector under the control of said promoter such that in a transformed host it is expressed to produce the polypeptide.

The invention also relates to a process for the preparation of a transformed host, which comprises transforming or transfecting a host with an expression vector containing a DNA of the invention regulated by an expression control sequence, and to the transformed or transfected hosts themselves.

Examples of suitable hosts are the above-mentioned microorganisms, such as strains of *Saccharomyces cerevisiae, Bacillus subtilis* and *Escherichia coli*. The transformation with the expression plasmids according to the invention is carried out, for example, as described in the literature, thus for *S. cerevisiae* [A. Hinnen, J. B. Hicks and G. R. Fink, Proc. Natl. Acad. Sci. USA 1978, 75, 1929], *B. subtilis* [Anagnostopoulos et al., J. Bacteriol. 1961, 81, 741] and *E. coli* [M. Mandel et al., J. Mol. Biol. 1970, 53, 159].

Accordingly, the transformation procedure of *E. coli* cells includes Ca$^{2+}$ pretreatment of the cells so as to allow DNA uptake, and incubation with the hybrid vector. The cells are transferred to a selective growth medium which allows separation of the transformed cells from the parent cells. Cells which do not contain the vector will not survive in such a medium. The transformation of yeast comprises, for example, the steps of (1) enzymatic removal of the yeast cell wall by means of glucosidases, (2) treatment of the obtained spheroplasts with the vector in the presence of polyethylene glycol and Ca$^{2+}$ ions and (3) regeneration of the cell wall by embedding the spheroplasts into agar. Preferably, the regeneration agar is prepared in a way to allow regeneration and selection of the transformed cells at the same time.

Further examples of suitable hosts are the above-mentioned mammalian cells, e.g. COS-7 cells, Bowes melanoma cells, chinese hamster ovary (CHO) cells or preferably embryonic lung cells L-132. The vectors are introduced into mammalian cells by transfection in the prescence of helper compounds, e.g. diethylaminoethyldextran, dimethyl sulfoxide, glycerol, polyethylene glycol or the like, or as co-precipitates of vector DNA and calcium phosphate. Further suitable methods include direct microinjection of vector DNA into the cell nucleus and electroporation, i.e. introduction of DNA by a short electric pulse increasing the permeability of cell membranes. The subsequent selection of transfected cells can be done using a selection marker which is either covalently integrated into the expression vector or added as a separate entity. Selection markers include genes which confer resistance to antibiotics, e.g. G-418 (neomycin) or hygromycin, or genes which complement a genetic lesion of the host cell such as the absence of thymidine kinase or hypoxanthine phosphoribosyl transferase.

A preferred selection system makes use of cells lacking dihydrofolate reductase (DHFR⁻), e.g. CHO cells, which absolutely require thymidine, glycine and purines for growth unless an exogenous DHFR gene is supplied. On introduction of a vector containing a DHFR gene linked to the gene coding for a polypeptide of the invention into suitable DHFR⁻ cells, e.g. CHO cells, transformed cells are selected by increasing the concentration of the anti-folate drug methotrexate in the medium. Such treatment furthermore amplificates the production of the desired polypeptide through amplification of the DHFR gene together with substantial flanking chromosomal regions containing the gene coding for the desired polypeptide.

Particularly preferred is a selection method wherein suitable mammalian cells, e.g. human embryonic lung cells L-132, are treated with co-precipitates of vector DNA containing the gene coding for a compound of formula I or II, a plasmid DNA containing a gene coding for antibiotics resistance, e.g. resistance to C-418, and calcium phosphate. The transformed cells are selected by culturing in the presence of the corresponding antibiotic, e.g. G-418, and by screening for expression of the desired polypeptide.

The transformed host cells are cultured by methods known in the art in a liquid medium containing assimilable sources of carbon, nitrogen and inorganic salts.

Various sources of carbon can be used for culture of the transformed hosts according to the invention. Examples of preferred sources of carbon are assimilable carbohydrates, such as glucose, maltose, mannitol or lactose, or an acetate, which can be used either by itself or in suitable mixtures. Examples of suitable sources of nitrogen are amine acids, such as casaminoacids, peptides and proteins and their degradation products, such as tryptone, peptone or meat extracts, yeast extracts, malt extract and also ammonium salts, for example ammonium chloride, sulfate or nitrate, which can be used either by themselves or in suitable mixtures. Inorganic salts which can also be used are, for example, sulfates, chlorides, phosphates and carbonates of sodium, potassium, magnesium and calcium.

The medium furthermore contains, for example, growth-promoting substances, such as trace elements, for example iron, zinc, manganese and the like, and preferably substances which exert a selection pressure and prevent the growth of cells which have lost the expression plasmid. Thus, for example, ampicillin is added to the medium if the expression plasmid contains an amp$^R$ gene. Such an addition of antibiotic substances also has the effect that contaminating antibiotic-sensitive microorganisms are destroyed. If a yeast strain which is auxotrophic in, for example, an essential amino acid is used as the host microorganism, the plasmid preferably contains a gene coding for an enzyme which complements the host defect. Cultivation of the yeast strain is performed in a minimal medium deficient in said amino acid.

Vertebrate cells are grown under tissue culture conditions using commercially available media optionally supplemented with growth-promoting substances and/or mammal sera. The cells are grown either attached to a solid support, e.g. a microcarrier or porous glass fibres, or free-floating in appropriate culture vessels.

Culturing is effected by processes which are known in the art. The culture conditions, such as temperature, pH value of the medium and fermentation time, are chosen so that a maximum titre of the polypeptide of the invention is obtained. Thus, an *E. coli* or yeast strain is preferably cultured under aerobic conditions by submerged culture with shaking or stirring at a temperature of about 20° to 40° C., preferably about 30° C., and a pH value of 4 to 8, preferably at about pH 7, for about 4 to 30 hours, preferably until maximum yields of the polypeptide of the invention are reached.

When the cell density has reached a sufficient value, the culture is interrupted and the polypeptide is isolated. If the polypeptide is fused with a suitable signal peptide sequence, it is excreted by the cell directly into the supernatant. Otherwise, the cells have to be destroyed, for example by treatment with a detergent, such as SDS, NP-40, Triton® or deoxycholic acid, or lysed with lysozyme, a similarly acting enzyme or with ultra-sound. If yeast is used as a host microorganism, the cell wall may be removed by enzymatic digestion with a glucosidase. Alternatively or additionally, mechanical forces, such as shearing forces (for example X-press, French press, Dyno mill) or shaking with glass beads or aluminium oxide, or alternating freezing, for example in liquid nitrogen, and thawing, for example to 30° to 40° C., as well as ultra-sound can be used to break the cells.

The cell supernatant or the solution obtained after centrifugation of the mixture obtained on breaking the cells, which contains proteins, nucleic acids and other cell constituents, is enriched in proteins, including the polypeptides of the invention, in a manner which is known per se. Thus, for example, most of the non-protein constituents are removed by polyethyleneimine treatment and the proteins including the polypeptides of the invention are precipitated, for example, by saturation of the solution with ammonium sulfate or with other salts. Otherwise, the cell supernatant or lysate is directly pre-purified using chromatographic methods.

The polypeptides prepared by genetically engineered microorganisms are purified by a combination of chromatographic separations, preferably by a combination of ion exchange chromatography with basic and acid functional groups and reversed phase high performance liquid chromatography as discussed hereinbefore. Other separation methods may be included in the purification protocol, e.g. filtration or ultrafiltration with molecular weight cut-off membranes, gel filtration, affinity chromatography, hydrophobic interaction chromatography, chromatography on hydroxylapatite, chromatofocusing, and methods of dialyzing, dissolving and reprecipitating in suitable salt and/or buffer solutions and solvent mixtures.

Preferred is a purification scheme wherein the crude cell supernatant or cell lysate is chromatographed sequentially on an ion exchange column bearing tertiary amino functions, on an ion exchange column bearing sulfonic acid residues and on a reversed phase liquid chromatography column. Other preferred schemes are those wherein ion exchange chromatography is performed only on one carrier containing sulfonic acid residues, and/or wherein gel filtration, i.e. size exclusion chromatography, is included in the purification protocol.

The invention concerns furthermore compounds of formula I or II, mutants, fragments and derivatives thereof, whenever prepared according to the methods of the present invention.

The invention concerns especially the DNA, the hybrid vectors, the transformed host cells, compounds of formula I and II and the processes for the preparation thereof as described in the Examples.

The immune regulating properties of a human macrophage migration inhibition factor related peptide, a mutant, fragment or a derivative thereof may be useful for the therapy of immune regulation diseases and chronic inflammatory diseases and for the protection against infections, preferably in the form of pharmaceutical preparations that contain a therapeutically effective amount of the active ingredient optionally together or in admixture with inorganic or organic, solid or liquid, pharmaceutically acceptable carriers.

The pharmaceutical preparations according to the invention are those for enteral, e.g. rectal or oral, administration and preferably for parenteral, e.g. intranasal, intramuscular, subcutaneous or intravenous, administration to warm-blooded animals, for example humans. Depending on the intended method of administration, the pharmaceutical preparations may be in unit dose form, for example in ampoules, vials, suppositories, dragées, tablets, capsules or nasal sprays in liquid or solid form.

The amount of the therapeutically effective compounds to be administered depends on the condition of the warm-blooded animal, for example the human, such as the body weight, the nature and severity of the disease and the general condition and also on the mode of administration, and is carried out in accordance with the assessment of the physician giving the treatment. The effective dose of a compound of formula I or II, of a mutant or fragment thereof is in the order of magnitude of from 0.001 to 1 µg per kg of body weight per day.

The pharmaceutical preparations according to the invention contain the customary inorganic or organic, solid or liquid pharmaceutically acceptable carriers, optionally together with other therapeutically effective compounds and/or adjuncts. There are preferably used solutions or suspensions of the active ingredient, especially isotonic aqueous solutions or suspensions, or also lyophilized preparations which are dissolved in water shortly before use. The pharmaceutical preparations may be sterilized and/or contain preservatives, stabilizers, wetting agents, emulsifiers, solubilizers, viscosity-increasing substances, salts for regulating the osmotic pressure and/or buffers, and also other proteins, for example human serum albumin or human blood plasma preparations.

Preferred are pharmaceutical preparations in the form of liposomes in aqueous dispersion containing a therapeutically effective amount of a MIF-related peptide, a mutant, fragment or derivative thereof. There are suitable, in particular, liposomes having a population of as homogeneous a size as possible and a diameter of approximately from $2.0 \times 10^{-8}$ to $5.0 \times 10^{-6}$ m consisting of one or more double layers of lipid components, for example amphipatic lipids, for example phospholipids, such as lecithin, cephalin or phosphatidic acid, and optionally neutral lipids, for example cholesterol, enclosing an aqueous interior containing a MIF-related peptide according to the invention. Preferred are liposomes consisting of a mixture of synthetic phosphatidylserine and phosphatidylcholine.

The invention further concerns polyclonal and monoclonal antibodies specific for a human macrophage migration inhibition factor related peptide, in particular for MRP-8 of formula I and for MRP-14 of formula II, and derivatives thereof.

Polyclonal antibodies against MIF-related peptides are of mammal origin, e.g. mouse, rat, rabbit, goat, sheep, equine, pig, chimpanzee or human origin. Preferred are mouse, rat, rabbit, goat or sheep antibodies, in particular rabbit antibodies. Such polyclonal antibodies may contain other antibodies than antibodies against compounds of formula I and compounds of formula II, respectively. In particular, polyclonal antibodies are a collection of antibodies with different affinity and selectivity towards MIF-related peptides. Preferred polyclonal antibodies are specific for MRP-8 and specific for MRP-14, respectively.

Preferred antibodies of the invention are monoclonal antibodies against MIF-related peptides. Monoclonal antibodies are also of mammal origin, e.g. mouse, rat or human origin, preferably mouse antibodies.

Particularly preferred are the monoclonal antibodies against MRP-8 with the designation 8-5C2 and 8-10D7 and the monoclonal antibodies against MRP-14 with the designation 14-6B2 and 14-19C9, and derivatives thereof. These monoclonal antibodies are secreted by the corresponding hybridoma cell lines with the designation 8-5C2, 8-10D7, 14-6B2 and 14-19C9, respectively.

Derivatives of antibodies of this invention are e.g. antibody fragments, radioactively labelled antibodies, and conjugates of the antibodies with e.g. enzymes, compounds with exceptional binding properties, e.g. avidin or biotin, fluorescent markers, chemiluminescent markers or paramagnetic particles.

Fragments of antibodies of this invention are e.g. Fab, Fab' or F(ab')$_2$ fragments, which retain their specificity for the antigenic determinants, i.e. which retain the characteristic binding pattern of the parent antibody to MIF-related proteins.

Radioactively labelled antibodies contain e.g. radioactive iodine ($^{123}$I, $^{125}$I, $^{131}$I), carbon ($^{14}$C), sulfur ($^{35}$S), tritium ($^3$H) or the like. Preferred are antibodies labelled with radioactive iodine, e.g. monoclonal antibodies labelled with $^{125}$I.

Antibody conjugates of the invention are e.g. conjugates with enzymes such as horseradish peroxidase, alkaline phosphatase, β-D-galactosidase, glucose-oxidase, glucoamylase, carboanhydrase, acetylcholinesterase, lysozyme, malate dehydrogenase or glucose-6-phosphate dehydrogenase, conjugates with biotin or avidin or conjugates with fluorescent markers, e.g. with fluorescein or rhodamine B, conjugates with chemiluminescent markers, e.g. acridinium esters, or conjugates with solid paramagnetic particles. In such conjugates the antibody is bound to the conjugation partner directly or by the way of a spacer or linker group. Preferred are conjugates of monoclonal antibodies with the enzymes horseradish peroxidase or alkaline phosphatase, and conjugates of polyclonal and monoclonal antibodies with biotin.

The selectivity of an antibody towards a MIF-related protein can be detected qualitatively in an enzyme-immunoassay wherein the wells of a microtiter plate are coated with the protein, then treated with the antibody to be tested, and bound antibody is detected with labelled antiserum directed against the antibody. For example, the selectivity of a mouse monoclonal antibody of the invention is determined in a sandwich type enzyme-immunoassay wherein the wells of a microtiter plate are coated with a rabbit polyclonal antibody to a MIF-related protein followed by the protein itself, then treated with the antibody to be tested, and bound monoclonal antibody is detected with labelled antiserum directed against the constant part of mouse antibodies.

The monoclonal antibodies can be further analyzed with respect to their immunoglobulin class and subclass, e.g. by the immuno-diffusion Ouchterlony method using class-specific second antibodies.

The antibodies of the invention and derivatives thereof are obtained by processes known per se. Polyclonal antibodies of the invention and derivatives thereof are obtained by a process, wherein a suitable mammal is immunized by two or more injections of a compound of formula I or II in the presence of an immune response enhancer, the blood serum of the immunized mammal is collected and the antibodies isolated and purified, and, if desired, the obtained antibodies are transformed into derivatives thereof.

Suitable mammals for the preparation of polyclonal antibodies are, for example, mice, rats, rabbits, goats, sheep, pigs or horses. Preferably mice or rabbits are used. They are immunized by two, three, four or more injections of the compound of formula I or II intradermally, subcutaneously, intravenously or intraperitoneally in regular or irregular intervals of a few days, e.g. three to seven days, up to several months, for example four weeks. The immune response enhancer is an adjuvans which stimulates the lymphocyte production, e.g. complete or incomplete Freund's adjuvans.

The immune response of the mammal is preferably monitored by a suitable antibody assay, e.g. an enzyme-immunoassay as described hereinbefore. The blood of the mammal is collected a few, e.g. two to five, days after the last booster immunization. The antibodies are isolated by known methods, e.g. by precipitation, centrifugation and/or chromatographic procedures. A crude immunoglobulin fraction may be obtained from the serum by precipitation with ammonium sulfate or the like. Such an immunoglobulin fraction can be further purified by gel filtration or molecular sieve chromatography, ion exchange chromatography, chromatography on DEAE cellulose or immunoaffinity chromatography, e.g. on carrier material bearing Staphylococcus protein A or, preferably, the corresponding MIF-related protein.

Antibody fragments, for example Fab, Fab' or F(ab')$_2$ fragments, which retain their specificity towards the antigenic determinants, can be obtained by methods known per se, e.g. by digestion of the antibodies with enzymes such as pepsin or papain and/or cleavage of disulfide bonds by chemical reduction.

Antibodies labelled with radioactive iodine are prepared by iodination methods known in the art, e.g. by labelling antibodies with radioactive sodium or potassium iodide and a chemical oxidant such as sodium hypochlorite, chloramine T or the like, or an enzymatic oxidant such as lactoperoxidase or glucose oxidase and glucose.

Conjugates of antibodies of the invention are prepared by methods known in the art, e.g. by reacting an antibody or a fragment thereof prepared as described hereinbefore with the enzyme in the presence of a coupling agent, e.g. glutaraldehyde, periodate, N,N'-o-phenylenedimaleimide, N-(m-maleimidobenzoyloxy)-succinimide, N-(3-[2'-pyridyldithio]-propionoxy)-succinimide, N-ethyl-N'-(3-dimethylaminopropyl)-carbodiimide or the like. Conjugates with avidin are prepared likewise. Conjugates with biotin are prepared e.g. by reacting antibodies with an activated ester of biotin such as the biotin N-hydroxysuccinimide ester. Conjugates with fluorescent or chemiluminescent markers are prepared in the presence of a coupling agent, e.g. those listed above, or by reaction with an isothiocyanate, preferably fluorescein-isothiocyanate. Conjugates with paramagnetic particles are obtained with preactivated particles or by coupling in the presence of e.g. glutaraldehyde or periodate.

The monoclonal antibodies of the invention and derivatives thereof are obtained by processes known per se, characterized in that hybridoma cells secreting said monoclonal antibodies a) are cultivated in vitro and the monoclonal antibodies isolated from the culture supernatant, or b) are propagated in vivo in a suitable mammal and the monoclonal antibodies recovered from body fluids of said mammal, and, if desired, the obtained monoclonal antibodies are converted into a derivative thereof.

Suitable culture media for the in vitro cultivation according to process a) are standard culture media such as Dulbecco's modified Eagle medium or RPMI 1640 medium, optionally replenished by a mammal serum, e.g. fetal calf serum, or other growth-sustaining supplements, e.g. 2-aminoethanol, insulin, transferrin, low density lipoprotein, oleic acid and the like, and trace elements. The isolation of the monoclonal antibodies is accomplished by precipitating the protein contained in the culture supernatants by ammonium sulfate or the like, followed by purifying the immunoglobulins by standard chromatographic methods, such as gel filtration, ion exchange chromatography, chromatography on DEAE cellulose or immunoaffinity chromatography.

In vitro production allows scale-up to give large amounts of the desired antibodies. Techniques for large scale hybridoma cultivation are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

Large amounts of the desired monoclonal antibodies can also be obtained by the propagation of hybridoma cells according to process b). Cell clones are injected into syngeneic mammals, which causes antibody-producing tumors to grow. After one to three weeks the desired monoclonal antibodies are recovered from body fluids of said mammal. As an example hybridoma cells derived from Balb/c mice are intraperitoneally injected into Balb/c mice optionally pretreated with a hydrocarbon such as pristane, and after one to two weeks, ascites fluid of these mice is collected. The desired monoclonal antibodies are isolated from the body fluids by methods known per se, e.g. by precipitating the proteins with ammonium sulfate or the like, followed by purifying the immunoglobulins by standard chromatographic methods, such as gel filtration, ion exchange chromatography, chromatography on DEAE cellulose or immunoaffinity chromatography.

Fragments, radioactively labelled derivatives and conjugates of monoclonal antibodies are prepared as described hereinbefore. Radioactively labelled monoclonal antibodies may also be prepared by adding radioactively labelled nutrients to the culture media of the in vitro cultivation of step a). Such labelled nutrients contain e.g. radioactive carbon ($^{14}$C).

The invention further concerns hybridoma cell lines, characterized in that they secrete monoclonal antibodies directed against MIF-related peptides, in particular against MRP-8 of formula I and against MRP-14 of formula II.

In particular the invention concerns cell lines which are hybrids of myeloma cells and B lymphocytes of a mammal immunized with compounds of formula I or II. Preferentially these cell lines are hybrids of mouse myeloma cells and B lymphocytes of a syngeneic mouse immunized with purified compounds of formula I or II.

Preferred are the hybridoma cell lines with the designation 8-5C2, 8-10D7, 14-6B2 and 14-19C9. These hybridoma cell lines are hybrids of the mouse myeloma cell line P3x63-Ag8.653 and of B lymphocytes of the spleen of Balb/c mice immunized with MRP-8 and MRP-14, respectively. They are stable cell lines, secrete the monoclonal antibodies with the corresponding designation and may be kept in deep-frozen cultures and reactivated by thawing and optional re-cloning.

The preferred hybridoma cell lines have been deposited on Sep. 9, 1987, at the "Collection Nationals de Cultures de Microorganismes", Institut Pasteur, 28 Rue du Docteur Roux, 75724, Paris Cedex 15, France under the regulations of the Budapest Treaty. The numbers of deposits assigned are: I-687 for cell line 14-19C9, I-688 for cell line 14-6B2, I-689 for cell line 8-10D7 and I-690 for cell line 8-5C2.

The invention concerns also a process for the production of hybridoma cell lines secreting monoclonal antibodies which bind to compounds of formula I or II, characterized in that a suitable mammal is immunized with a compound of formula I or II, antibody-producing cells of this mammal are fused with myeloma cells, the hybrid cells obtained in the fusion are cloned, and cell clones secreting the desired antibodies are selected.

Suitable antigens for the immunization of mammals in the process of the invention are the preferred compounds of formula I and II, MRP-8 and MRP-14, respectively, described hereinbefore. Preferred mammals for the immunization are mice, in particular Balb/c mice. The immunizations are performed e.g. as described hereinbefore for the preparation of polyclonal antibodies.

Antibody-producing cells of the immunized mammals, preferably spleen cells, taken two to five days after the final booster injection, are fused with myeloma cells of a suitable cell line in the presence of a fusion promoter. Several suitable myeloma cell lines are known in the art. Preferred are myeloma cell lines lacking the enzyme hypoxanthine guanine phosphoribosyl transferase (HGPRT) or the enzyme thymidine kinase (TK), which therefore do not survive in a selective culture medium containing hypoxanthine, aminopterin and thymidine (HAT medium). Particularly preferred are myeloma cells and derived cell lines that do not survive in HAT medium and do not secrete immunoglobulins or fragments thereof, such as the cell lines P3x63-Ag8.653 or Sp2/O-Ag14. Fusion promoters considered are e.g. Sendai virus or other paramyxo viruses, optionally in UV-inactivated form, calcium ions, surface-active lipids such as lysolecithin, or polyethylene glycol. Preferentially, the myeloma cells are fused with a three- to twentyfold excess of spleen cells from immunized mammals in a solution containing about 30% to about 60% polyethylene glycol of a molecular weight between 1000 and 4000 and about 10% to about 20% dimethyl sulfoxide.

After the fusion, the cells are resuspended and cultivated in selective HAT medium. Thereby, only hybridoma cells will survive, because they combine the ability to grow and replicate in vitro inherited from myeloma cells and the missing HGPRT or TK genes essential for the survival in the HAT medium inherited from the antibody-producing spleen cells of the immunized mammals.

Suitable culture media for the expansion of hybridoma cells are the standard culture media, such as Dulbecco's modified Eagle medium, minimum essential medium, RPMI 1640 medium and the like, optionally replenished by serum, e.g. 10 to 15% fetal calf serum. Optionally feeder cells are added at the beginning of the cell growth, e.g. normal mouse peritoneal exudate cells, spleen cells, marrow bone macrophages, or the like. The culture media are supplemented with selective HAT medium, at later stages with hypoxanthine/thymidine (HT) medium, in order to prevent normal myeloma cells over-growing the hybridoma cells.

The hybridoma cell culture supernatants are screened for the desired monoclonal antibodies, preferentially with an enzyme immunoassay or a radioimmunoassay. Positive hybridoma cells are cloned, e.g. by limiting dilution. The cloned cell lines may be frozen in a conventional manner.

The polyclonal and monoclonal antibodies of the invention and/or their derivatives are useful for the qualitative and quantitative determination of MIF-related proteins, in particular of compounds of formula I or II.

For instance, the antibodies or derivatives thereof, such as enzyme conjugates or radioactive derivatives, can be used in any of the known immunoassays, which rely on the binding interaction between the antigenic determinant of the MIF-related proteins and the antibodies. Examples of such assays are radioimmunoassays (RIA), enzyme-immunoassays, e.g. enzyme-linked immunosorbent assay (ELISA), immunofluorescence, immunoprecipitation, latex agglutination, and hemagglutination. Such immunoassays are useful e.g. in the qualitative and quantitative determination of the MIF-related proteins in biological fluids or tissues, e.g. of patients with inflammatory conditions and of patients or healthy human subjects with genetic predisposition of cystic fibrosis.

The antibodies according to the invention can be used as such or in the form of radioactively labelled derivatives in a radioimmunoassay (RIA). Any of the known modifications of an RIA can be used, for example RIA in homogeneous phase, solid phase RIA or heterogeneous RIA, single RIA or double (sandwich) RIA with direct or indirect (competitive) determination of the protein of the invention. There is preferred a sandwich RIA in which a suitable carrier, for example the plastics surface of a microtitre plate or of a test tube, for example of polystyrene, polypropylene or polyvinyl chloride, glass or plastics beads, filter paper, or dextran, cellulose acetate or nitrocellulose sheets or the like, is coated with a polyclonal or monoclonal antibody of the invention by simple adsorption or optionally after activation of the carrier, for example with glutaraldehyde or cyanogen bromide, and incubated with the test solution and a solution of a monoclonal antibody radio-actively labelled with $^{125}I$, the dissolved monoclonal antibody recognizing another epitope of the proteins of the invention than the carrier-bound monoclonal antibody, if such is used, and the amount of the proteins of the invention is determined by measuring the radioactivity bound to the carrier.

Particularly preferred is a sandwich radioimmunoassay as described hereinbefore, wherein a monoclonal antibody of the invention is bound to a bead, for example a polystyrene bead, this coated bead is incubated in a test or standard solution containing MIF-related proteins and is finally developed with a radiolabelled monoclonal antibody recognizing a different epitope.

The antibodies according to the invention can be used as such or in the form of enzyme-conjugated or biotin-conjugated derivatives in an enzyme-immunoassay (EIA). Such immunoassays include test procedures in which enzyme-labelled monoclonal antibody derivatives according to the invention, enzyme-labelled antibodies known per se that recognize and bind an epitope of the antibodies according to the invention, or enzyme-avidin conjugates are used. Any of the known modifications of an EIA can be used, for example EIA in homogeneous phase, solid phase EIA or heterogeneous EIA, single EIA or double (sandwich) EIA with direct or indirect (competitive) determination of the MIF-related protein.

There is preferred an ELISA (enzyme-linked immunoadsorbent assay) in which a carrier as described above for an RIA is coated with a polyclonal or monoclonal antibody according to the invention, incubated with a test solution containing a MIF-related protein and then with a polyclonal or different monoclonal antibody conjugated to biotin, and, finally, the bound antibody-biotin conjugate is developed by an enzyme-avidin conjugate, and the amount of the protein bound is determined by an enzyme substrate reaction.

There is also preferred an ELISA in which a carrier coated with a polyclonal or monoclonal antibody according to the invention is incubated with a test solution and with a solution of a monoclonal antibody that is conjugated with an enzyme, the dissolved monoclonal antibody recognizing a different epitope of the MIF-related protein than does the carrier-bound monoclonal antibody, if such is used. By an enzyme substrate reaction that results, for example, in a colour change and can be observed by eye or with optical measuring devices, the amount of bound enzyme, which is proportional to the amount of the protein in the test solution, is measured.

There is further preferred an ELISA in which a carrier coated with a polyclonal or monoclonal antibody according to the invention is incubated with a test solution, with a solution of a monoclonal or polyclonal antibody of a different species than the carrier-bound antibody and then with an enzyme-labelled second antibody that recognizes and binds the species-specific part of the dissolved antibody. The amount of bound enzyme is proportional to the amount of the protein in the test solution and can be determined by an enzyme substrate reaction.

The monoclonal antibodies according to the invention can be used as such or in the form of derivatives conjugated with fluorescent markers in immunofluorescence tests. Such immunofluorescence tests include procedures wherein monoclonal antibody derivatives according to the invention, e.g. derivatives conjugated with fluorescein, or fluorescent marker-labelled antibodies known per se that recognize and bind an epitope of the monoclonal antibodies according to the invention are used.

There is preferred an immunofluorescence test in which a carrier as described above for an RIA is coated according to standard methods with cells to be tested for the presence of a protein of the invention, the cells are fixed and permeabilized to allow interaction of proteinaceous material inside the cell with solutions applied, then incubated with a solution of a polyclonal or monoclonal antibody derivative according to the invention conjugated with a fluorescent marker, or incubated with a solution of a polyclonal or monoclonal antibody of the invention followed by a solution of a fluorescent marker-labelled second antibody that recognizes and binds the antibody of the invention, e.g. a fluorescein-labelled rabbit anti-mouse immunoglobulin. The presence of a protein of the invention is then detected and the protein localized by standard fluorescence microscopy or flow cytometry.

Also preferred is the corresponding enzyme immunohistological test in which the fixed cells are incubated with a polyclonal or monoclonal antibody of the invention followed by a solution of a enzyme-labelled second antibody that recognizes and binds the antibody of the invention, e.g. a peroxidase-labelled anti-rabbit or anti-mouse antiserum. The presence of a protein of the invention is then detected and the protein localized by an enzyme substrate reaction.

The use according to the invention of monoclonal antibodies and derivatives thereof as described hereinbefore for the qualitative and quantitative determination of the MIF-related proteins also includes other immunoassays known per se, for example immunodot analysis, immunoprecipitation tests with radiolabelled antibodies or radiolabelled MIF-related proteins, latex agglutination with antibody-coated or antigen-coated latex particles or hemagglutination with antibody-coated or antigen-coated red blood corpuscles or the like.

The invention relates also to test kits for the qualitative and quantitative determination of MIF-related proteins, in particular of compounds of formula I or II, containing polyclonal and/or monoclonal antibodies of the invention and/or derivatives thereof and, optionally, other monoclonal or polyclonal antibodies and/or adjuncts.

Test kits according to the invention for a radioimmunoassay contain, for example, a suitable carrier, uncoated or coated with a polyclonal or monoclonal antibody of the invention, optionally freeze-dried or concentrated solutions of a monoclonal or polyclonal antibody to a compound of formula I or II and/or a radiolabelled derivative thereof, standard solutions of the corresponding compound of formula I or II, buffer solutions and, optionally, polypeptides and detergents for preventing non-specific adsorption and aggregate formation, pipettes, reaction vessels, calibration curves, instruction manuals and the like.

Test kits according to the invention for an enzyme-immunoassay contain, for example, a suitable carrier, e.g. microtiter plates or nitrocellulose sheets, optionally freeze-dried or concentrated solutions of a polyclonal or monoclonal antibody to a compound of the formula I or II and of an enzyme-labelled or biotin-labelled monoclonal or polyclonal antibody to this protein, solutions of an enzyme-avidin conjugate, if a biotin-labelled antibody is used, enzyme substrates in solid or dissolved form, standard solutions of a protein of the invention, buffer solutions and, optionally, polypeptides and detergents, pipettes, reaction vessels, calibration curves, colour scale tables, instruction manuals and the like.

The monoclonal antibodies and antibody derivatives of the invention are used for the qualitative and quantitative determination of MIF-related proteins, in particular of compounds of formula I or II, e.g. MRP-8 and MRP-14, respectively, preferably in enzyme-immunoassays. The reliable determination of the amount of MRP-8 and MRP-14 in biological fluids, tissue sections and cells allows a simple detection of inflammatory conditions and/or genetic predisposition for cystic fibrosis. Furthermore, the monoclonal antibodies and antibody derivatives can be used in the isolation and purification of the MIF-related proteins of the invention from natural sources or from recombinant host cells by immunoaffinity chromatography.

The MIF-related peptides MRP-8 and MRP-14 of this invention occur in varying amounts of normal granulocytes and monocytes depending on the donors. Upon cultivation of granulocytes and monocytes, the number of MRP-8 and MRP-14 positive cells increase up to day 3 of culture and then decline approaching zero levels from day 10 and on. MRP-8 and MRP-14 seem not to be present in normal human tissue except in intravascular monocytes e.g. in liver, MRP-14 also in monocytes in the lung and in placenta.

However, in chronic inflammatory lesions MRP-8-positive macrophages are detected. In the case of dermal sarcoidosis also endothelial cells contain MRP-8. MRP-14-positive marcophages are seen in substantial number in rheumatoid arthritis tissue. MRP-8 and MRP-14 are expressed by subsets of tissue marcophages in primary chronic polyarthritis and other chronic inflammation in a pattern different from acute inflammation such as gingivitis.

The invention therefore concerns a method of diagnosis of chronic inflammatory conditions, characterized in that the antibodies to MRP-8 and to MRP-14 described hereinbefore are used to determine the amount and pattern of expression of MRP-8 and MRP-14 in tissue.

Cystic fibrosis (CF) is an autosomal recessive disease the aetiology of which is not yet known. There is a need for a simple method which allows rapid and reliable determination whether a subject is normal, CF heterozygous or CF homozygous. CF heterozygotes are clinically unaffected but may transmit the disease to the next generation.

A screening program of plasma samples of healthy donors, CF heterozygotes, CF homozygotes and patients with different inflammatory and allergical conditions and other diseases reveals the usefulness of MRP-14 as a marker for cystic fibrosis (Table).

TABLE

Determination of MRP-14 in plasma samples[a]

| Sample type | Samples tested | MRP-14 mean (µg/ml) | range[c] |
|---|---|---|---|
| Healthy donors | 39 | 0.043 | 0.003–0.132 |
| CF homozygotes | 11 | 1.076 | 0.204–5.78 |
| CF heterozygotes | 7 | 0.611 | 0.161–1.020 |
| Rheumatoid polyarthritis | 13 | 0.618 | 0.093–1.48 |
| Asthma | 2 | 0.595 | 0.357–0.476 |
| T-cell lymphoma | 2 | 1.32 | 0.240–2.04 |
| Neurodermitis | 1 | 1.840 | — |
| Psoriasis | 6 | 0.027 | 0.014–0.036 |
| Miscellaneous[b] | 7 | — | <0.030 |

[a]Sandwich type ELISA of Example 42, two independent experiments per sample (standard deviation within 10%)
[b]Mycosis fungoides, sarcoidosis, lepra, contact dermatitis.
[c]Highest and lowest value observed The average amount of MRP-14 found in healthy donors is 0.043 µg/ml with a maximum value of 0.132 µg/ml. Patients suffering from CF show a plasma concentration between 0.204 and 5.78 µg/ml with a mean value of 1.076 µg/ml. CF heterozygotes, i.e. plasma donors which are parents of CF patients but not clinically affected themselves, show average MRP-14 concentrations of 0.611 µg/ml with a minimum value of 0.161 µg/ml. Taking into account the reproducibility of the standard assay of ±10%, it will therefore be possible to judge reliably whether an otherwise healthy subject is heterozygous in CF or not with a limit set around 0.15 µg/ml.

Patients suffering from rheumatoid polyarthritis, asthma, T-cell lymphoma and neurodermitis show also elevated levels of MRP-14, whereas patients with several other diseases including psoriasis have MRP-14 concentrations in the normal range.

The amount of MRP-8 found in plasma samples of healthy donors, CF homozygotes and CF heterozygotes is usually less than 0.01 µg/ml and not indicative of cystic fibrosis.

The invention therefore concerns a method of reliable diagnosis of cystic fibrosis, characterized in that antibodies to MRP-14 described hereinbefore are used to determine the amount of MRP-14 in plasma samples of otherwise healthy subjects supposed to be homozygous or heterozygous in cystic fibrosis.

Figure 1A:
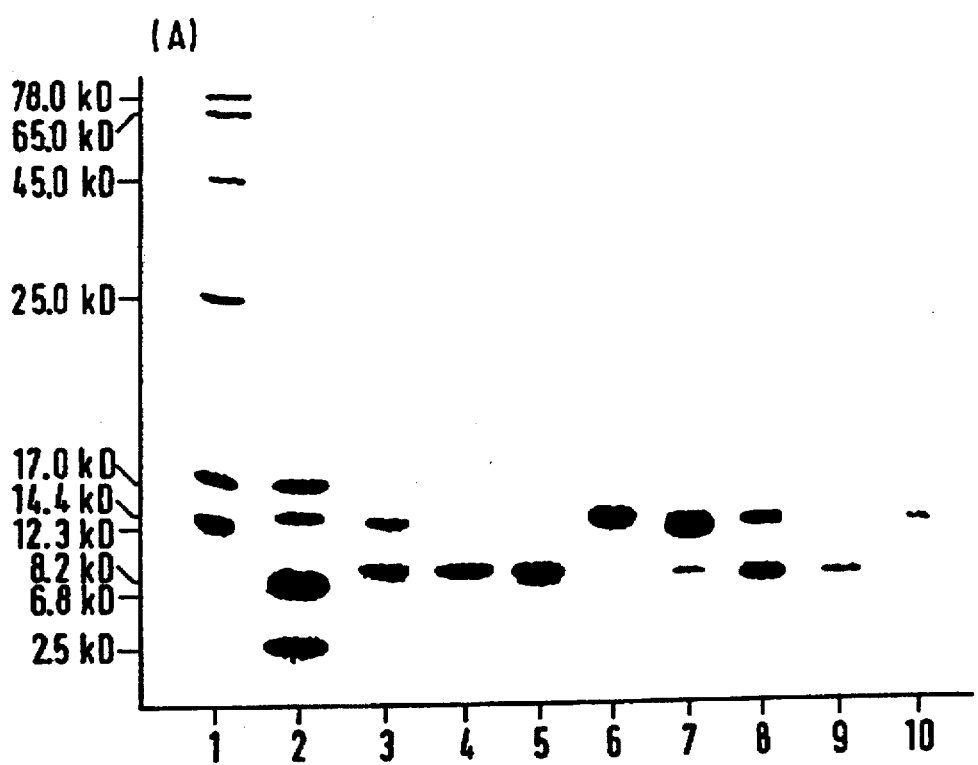
FIGS. 1A, 1B displays polyacrylamide gels of SDS-PAGE under reducing (FIG. 1A) and non-reducing (FIG. 1B) conditions as described in Example 1.2. Lane 1 and 2: molecular weight markers. Lane 3: Total protein as eluted from the 1C5 immunoaffinity column of Example 1.1. Lanes 4 to 10: HPLC fractions I to VIII.

The following Examples serve to illustrate the present invention but should not be construed as a limitation thereof.

The abbreviations used in the Examples have the following meanings:

ATP adenosine triphosphate
bp base pairs
BSA bovine serum albumin
cDNA complementary DNA
cpm counts per min (radioactive decay)
2'-deoxyadenosine
dATP 2'-deoxyadenosine triphosphate
dC 2'-deoxycytidine
dCTP 2'-deoxycytidine triphosphate
DEAE diethylaminoethyl
dG 2'-deoxyguanosine
dGTP 2'-deoxyguanosine triphosphate
DMEM Dulbecco's modified Eagle's medium
DMSO dimethyl sulfoxide
DNA deoxyribonucleic acid
dNTP mixture of dATP, dCTP, dGTP and dTTP
dpm desintegrations per min (radioactive decay)
ds DNA double-stranded DNA
dT (2'-deoxy-)thymidine
DTT 1,4-dithiothreitol
dTTP thymidine triphosphate
EDTA ethylenediamine-tetraacetic acid
FAB-MS fast atom bombardment mass spectroscopy
FCS fetal calf serum
FPLC fast protein, polypeptide, polynucleotide liquid chromatography
HAT hypoxanthine/aminopterin/thymidine
HBS Hepes buffered physiological saline
Hepes N-2-hydroxyethylpiperazine-N'-2-ethanesulfonic acid
HPLC high performance liquid chromatography
IgG immunoglobulin G
kb kilobase
kD kilo-Dalton (molecular weight)
MEM minimum essential Eagle's medium
MIF macrophage migration inhibition factor
mRNA messenger RNA
MRP MIF related peptide
OD optical density
PAGE polyacrylamide gel electrophoresis
PBS phosphate buffered physiological saline
PMSF phenylmethylsulfonyl fluoride
RNA ribonucleic acid
rpm revolutions per min
SDS sodium dodecyl sulfate
TFA trifluoroacetic acid
Tris tris(hydroxymethyl)aminomethane
tRNA transfer RNA The following buffer solutions and media are used:

Denhardt's solution 0.1% polyvinylpyrrolidone (PVP-360, Sigma), 0.1% Ficoll 400 (Pharmacia), 0.1% BSA.
elution buffer 10 mM Tris-HCl, pH 7.5, 1 mM EDTA, 0.2% SDS.
GuSCN buffer 4M guanidinium isothiocyanate, 50 mM Tris-HCl, pH 7.5, 10 mM EDTA, 2% sodium N-lauroylsarcosinate (sarkosyl), 140 mM β-mercaptoethanol.
LB medium (L broth) 1% Bacto® tryptone (Difco), 0.5% Bacto® yeast extract (Difco), 170 mM NaCl, adjusted to pH 7.5 with NaOH.
PBS 136 mM Nacl, 2 mM KCl, 8 mM $Na_2HPO_4$, 1.4 mM $KH_2PO_4$.
RVT buffer 200 mH Tris-HCl, pH 8.3 at 42° C., 20 mM $MgCl_2$, 280 mM KCl, 20 mM DTT.
SOC medium 2% tryptone (Gibco), 0.5% yeast extract (Gibco), 10 mN NaCl, 2.5 mM KCl, 10 mM $MgCl_2$, 5 mM $MgSO_4$, 20 mM glucose.
SSC buffer 15 mM sodium citrate, 150 mM NaCl, adjusted to pH 7.0 with NaOH.
TBE buffer 89 mM Tris (TRIZMA® base), 89 mM boric acid, 1 mM EDTA.
TNE buffer 10 mM Tris-HCl, pH 8.0, 1 mM EDTA, 0.1M NaCl.
wash buffer 10 mM Tris-HCl, pH 7.5, 1 mM EDTA, 0.5M NaCl, 0.2% SDS.

EXAMPLE 1

Isolation and purification of natural MIF related peptides 1.1. Reversed phase HPLC: Human mononuclear cells are stimulated and cultured, and the resulting cell culture supernatants concentrated and purified by an immunoaffinity chromatography column carrying monoclonal antibodies 1C5 as described in European Patent Application 162 812. Fractions containing proteins are made 1% in TFA and separated in portions of 1.1 ml on a Vydac® 214 TP 5415 reversed phase HPLC column (The Separations Group, Hesparia Calif., USA) using Waters Inc. HPLC equipment. The column is equilibrated in a mixture of 65% TFA 0.1% in water and 35% TFA 0.07% in acetonitrile, and the product eluted by a linear gradient over 30 min. ending with a mixture of 45% TFA 0.1% in water and 55% TFA 0.07% in acetonitrile at a flow rate of 1 ml/min. The eluate is monitored for absorbance at 220 nm with a Kratos Spectroflow 773 HPLC UV detector. Seven individual peaks with retention times of 11.8 min (I), 12.6 min (II), 13.4 min (III), 14.4 min (IV), 15.2 min (V), 16.0 min (VI), and 16.6 min (VII) are collected manually according to the UV absorbance.

Figure 1B:
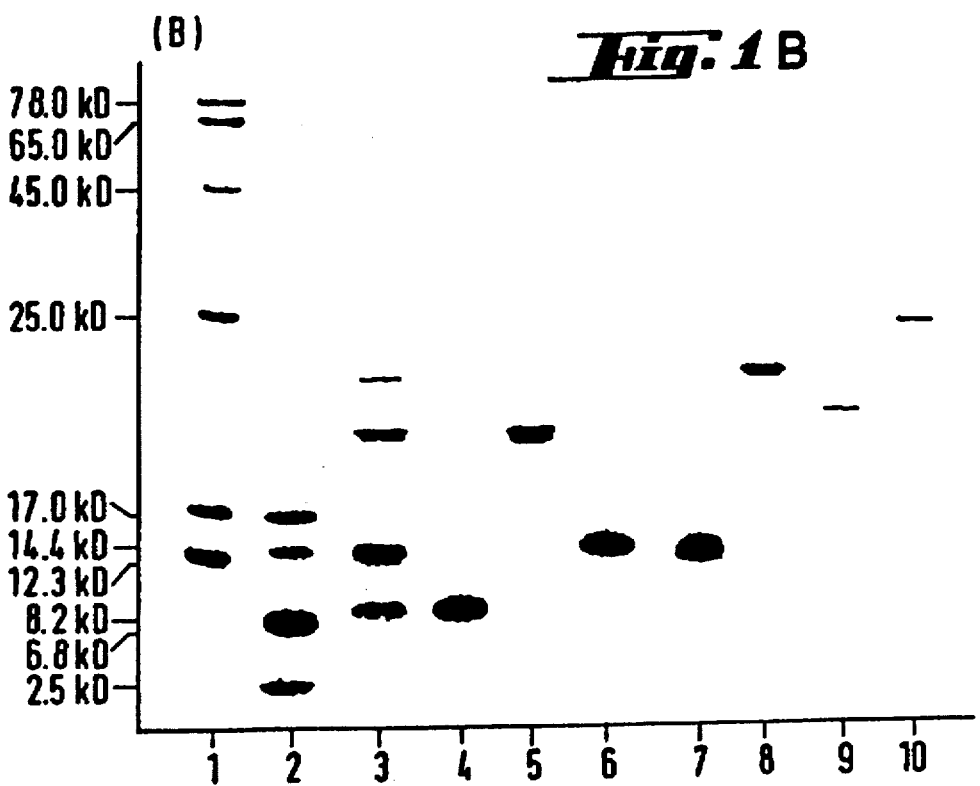

1.2. Analysis by SDS-PAGE: Aliquots of fractions I to VII are analyzed by SDS-PAGE under reducing and non-reducing conditions [U. K. Laemmli, Nature 1970, 227, 680] and stained with Coomassie Blue R-250 (FIG. 1). Aliquots (1–5%) of the HPLC fractions are dried in vacuo, dissolved in 20 µl dissociation buffer with or without (reducing) DTT (1%), heated for 2 min at 96° C. and applied to a 15% polyacrylamide gel.

The protein of fraction I is identical with the known human MIF protein of apparent molecular weight 8 kD described in EP 162 812. Fraction II contains dimeric MIF protein 8 kD appearing as a double band at 16.5 kD under non-reducing conditions and as a strong band at 8 kD with a faint, slightly faster moving band under reducing conditions. The protein of fraction III appears at 14 kD under reducing and non-reducing conditions and is named MRP-14. The protein of fraction IV exhibits a double band at 13 kD and is named MRP-14'. The protein of fraction V with apparent molecular weight of 20 kD consists of the disulfide linked heterodimer of the 8 kD MIF protein and MRP-14 as shown under reducing conditions. The protein of fraction VI of 17.5 kD is a further disulfide linked heterodimer of a 8 kD protein, and the protein of fraction VII appearing at 23.5 kD is the disulfide linked dimer of MRP-14.

1.3. Alternative method of isolation of natural MIF related peptides: 770 ml of the concentrated supernatant of cultured human mononuclear cells of European Patent Application 162 812 are dialysed extensively against 50 mM sodium acetate (NaOAc) buffer, pH 4, and pumped onto a SP Trisacryl® M (LKB) ion exchange column (2.6×10 cm). The column is washed until the UV 254 nm absorption reaches baseline level. Proteins bound to the column are eluted using a linear gradient of NaCl in 50 mM NaOAc, pH 4.0, ranging from 0.0M to 1.0M NaCl (300 ml) at a flow rate of 1.8 ml/min. Individual fractions of 18 ml are collected and analyzed by SDS-PAGE.

MRP-8, MRP-14 and MRP-14' are eluted together in the same fractions between 250 ml and 280 ml of the total gradient volume corresponding to approximately 0.8M–0.9M NaCl. The pool of MRP containing fractions is concentrated by ultrafiltration on a YM-10® membrane (Amicon) and made 1% in TFA. Isolation of pure MRP-8, MRP-14 and MRP-14' respectively is achieved on a Vydac® 214 TP 510 reverse phase HPLC column (The Separations Group, USA). The column is equilibrated in a mixture of 75% TFA 0.1% in water and 25% TFA 0.07% in acetonitrile, and the proteins are eluted by a linear gradient over 45 min ending with a mixture of 45% TFA 0.1% in water and 55% TFA 0.07% in acetonitrile at a flow rate of 3 ml/min. The eluate is monitored for absorbance at 235 nm. Individual peaks are collected manually according to the absorption reading. MRP-8, MRP-14 and MRP-14' are identified by comparison with the peptides isolated according to Example 1.1.

EXAMPLE 2

Enzymatic cleavage of MRP-14

25 µg of the protein of fraction III (Example 1) named MRP-14 are incubated for 6 h at room temperature with 0.5 µg of *Staphylococcus aureus* V8 protease (Cooper Biomedical) in 100 µl 50 mM $NH_4HCO_3$. The progress of digestion is monitored by analysis of small aliquots (2%) of the incubation mixture on a Vydac® 214 TP 5415 reversed phase HPLC column (The Separations Group). Preparative separations of the peptide fragments are achieved on the same column with a linear gradient of 60 min from 100% TFA 0.1% in water to 100% TFA 0.07% in acetonitrile at a flow rate of 1 ml/min. Three fractions are collected manually according to the UV absorbance at 220 nm at retention times of 20.7 min (A), 22.7 min (B) and 24.8 min (C).

EXAMPLE 3

Amino acid sequence analysis of *Staphylococcus aureus* V8 protease fragments of MRP-14

Fractions A, B and C (Example 2) are evaporated in vacuo, dissolved each in 25 µl 0.1% aqueous TFA and subjected to an amino acid sequence determination on a gas phase protein sequencer model 470 from Applied Biosystems.

The N-terminal amino acid sequences found are:

Thr—Ile—Ile—Asn—Thr—Phe—His—Gln—Tyr—Ser—Val—Lys—Leu—Gly— (A)

Phe—Ile—Met—Leu—Met—Ala—Arg—Leu—Thr—Trp—Ala—Ser—$X_{13}$—Glu—Lys—Met— (B)

Leu—Val—$X_3$—Lys—Asp—Leu—$X_7$—Asn—Phe—Leu—Lys—Lys—Glu—Asn—Lys—Asn—Glu—Lys—Val—Ile—$X_{21}$—$X_{22}$—Ile— (C)

Wherein $X_n$ means an undetermined amino acid at position n from the N-terminal.

EXAMPLE 4

Isolation of messenger RNA from human mononuclear blood leukocytes $1.6 \times 10^{10}$ mononuclear human blood leukocytes are isolated from buffy coats and treated with concanavalin A for 2 h as described in European Patent Application 162 812. After 16 h of incubation at 37° C. in RPMI 1640 medium (5% $CO_2$) in spinner cultures, the cells are collected by centrifugation for 15 min at 350×g. The fluffy cell pellet of approximately 10 ml is dissolved in 50 ml GuSCN buffer and homogenized in a Sorvall omnimixer (100 ml) at maximum speed for 90 sec. Subsequently, the solution is thoroughly mixed with 60 ml of phenol previously equilibrated with a solution containing 10 mM Tris-HCl pH 7.5, 100 mM NaCl and 1 mM EDTA. Phase separation is achieved by addition of 60 ml of chloroform, mixing and centrifugation at 3000 rpm in a tabletop centrifuge. The aqueous phase including some of the nonviscous interphase is collected and 60 ml of equilibrated phenol and chloroform are added sequentially. The mixture is centrifuged, and the aqueous phase and the nonviscous interphase are recovered. These steps are repeated 3–4 times until all interphase has virtually disappeared. Nucleic acids are precipitated at −20° C. by addition of 2 volumes of ethanol (100 ml). The RNA is further purified from contaminating DNA as follows: the nucleic acids are dissolved in 6 ml $H_2O$. 1.5 ml of 0.5M EDTA pH 7.5, then a mixture of 7.5 g of baked CsCl and 215 µl 1N HCl are added. The solution is layered over two 2 ml cushions of 5.7M CsCl in 0.1M EDTA pH 7.5 (final) in two TST41 tubes (Kontron). The tubes are filled up with $H_2O$ and centrifuged in a TST41 rotor for 16 h at 20° C. At the end of the run most of the supernatant is removed and the tube is drained by quickly inverting. The glazy RNA pellet is dissolved in 4 ml elution buffer by vortexIug and occasional warming (2 min) at 37° C. The RNA is precipitated by addition of 10 ml of ethanol and centrifugation in a HB 4 rotor (Sorvall) for 10 min. The RNA (9.5 mg) is briefly dried and dissolved in 0.4 ml of elution buffer. After heating for 2 min at 68° C. and chilling on ice, 0.44 ml of 5M NaCl are added and the solution is applied to a column containing 0.5 g oligo-dT cellulose (type 7, Pharmacia) equilibrated in wash buffer. After three subsequent applications of the sample, the column is washed with 15 ml of wash buffer, and the bound RNA eluted with 4 ml of elution buffer. The eluted material is heated for 2 min at 68° C., chilled, and 0.44 ml of 5M NaCl are added. The solution is applied to the re-equilibrated oligo-dT cellulose column (three times). After washing with 15 ml of wash buffer the bound RNA is eluted with 4 ml of elution buffer. The RNA is precipitated overnight at −20° C. by addition of 0.25 ml of 3M NaOAc pH 5.5 and 10 ml of ethanol. The precipitate (110 μg) is collected by centrifugation (15 min at 16000×g), dissolved in 0.4 ml $H_2O$ and re-precipitated by addition of 25 μl of 3M NaOAc and 1 ml of ethanol. After chilling in dry-ice for 10 min the RNA is collected by centrifugation for 5 min in an Eppendorf centrifuge. The pellet is air dried and dissolved in 110 μl of $H_2O$.

EXAMPLE 5

Size fractionation of polyadenylated RNA

90 μg of polyadenylated RNA (Example 4) are denatured at 80° C. for 2 min in 200 μl of 50% DMSO, 10 mM Tris-HCl pH 7.5, 1 mM EDTA and 0.5% SDS. After cooling and addition of 300 μl $H_2O$, the solution is layered onto 11.5 ml of a linear sucrose gradient 5–15% w/v in 100 mM NaCl, 10 mM Tris-HCl pH 7.5, 1 mM EDTA and 0.5% SDS, in a TST41 rotor (Kontron). After centrifugation at 41000 rpm for 4.5 h at 25° C., 30 0.4 ml fractions are collected and individual UV spectra recorded. The RNA from individual fractions is precipitated by addition of 15 μl 0.3M NaOAc pH 5.5 and 1 ml of ethanol. After incubation overnight at −20° C., the RNA is collected by centrifugation, dissolved and reprecipitated as above. Finally the RNA is dissolved in 20 μl $H_2O$.

EXAMPLE 6

Localization of MRP-8 mRNA among the size-fractionated RNA

Mixed oligodeoxynucleotides are synthesized on the basis of the known partial aminoacid sequence of MRP-8. Oligodeoxynucleotide mixture 1 has the composition 5'-TAYTTRTGRTANACRTC-3', wherein A, T, G, and C stand for adenosine, thymidine, guanosine, and cytosine, respectively, Y and R for pyrimidines (T,C) and purines (A,G), respectively, and N for any of the four deoxynucleotides. Oligodeoxynucleotide mixture 2 is composed of 5'-TCYTTRAACCANACRTC-3', wherein the codes have the same meaning as above. These two mixtures of 64 and 32 different 17-mers represent the possible complementary DNA strands to amino acids 14–19 and 52–57, respectively, of MRP-8. The oligodeoxynucleotides are synthesized following the procedure of Y. Ike et al., Nucleic Acid Research 1983, 11, 477. The 5' ends of the oligodeoxynucleotides are rendered radioactive (1–2×10$^9$ dpm/μg) using γ-$^{32}$P-dATP (5000 Ci/mmol) and polynucleotide kinase (Pharmacia) using standard procedures (T. Maniatis, E. F. Fritsch and J. Sambrook, "Molecular cloning, a laboratory manual", Cold Spring Harbor Laboratory, 1982). 2×2 μl of the size-fractionated RNA of Example 5 are spotted on replica filters (Pall-Biodyne™) and baked at 80° C. for 2 h in a vacuum oven. The filters are prehybridized for 3 h at 32° C. in 50 ml of Denhart's solution containing 0.9M NaCl, 180 mM Tris-HCl pH 8.0, 6 mM EDTA, 0.5% SDS and 50 μg/ml sheared single stranded calf thymus DNA. After removing the prehybridization solution, one filter is hybridized for 36 h at 29° C. in 1.5 ml of prehybridization solution containing in addition 5×10$^7$ dpm of oligodeoxynucleotide mixture 1. The second filter is hybridized at 32° C. in the same solution containing 5×10$^7$ dpm of oligodeoxynucleotide mixture 2. At the end of the hybridization the filters are washed at 25° C. (filter 1) and 29° C. (filter 2) 15 min with 250 ml of 0.6M NaCl, 0.12M Tris-HCl pH 8.0, 4 mM EDTA and 0.2% SDS and four times 15 min with 250 ml 0.3M NaCl, 0.06M Tris-HCl pH 8.0, 2 mM EDTA and 0.2% SDS. After drying the filters are exposed for 3 days at −80° C. on X-ray film using an Ilford Fast Tungstate Screen®. By comparison of the replicas, fraction 23 (9S) is estimated to contain most MRP-8 mRNA.

EXAMPLE 7

Localization of MRP-14 mRNA among the size-fractionated RNA

Oligodeoxynucleotide mixture 3 of the composition 5'-TAYTGRTGRAAIGTRTTIATIATNGT-3', wherein I stands for inosine, i.e. a mixture of 64 different 26-mers representing the possible complementary DNA strands to a mRNA coding for amino acids 1–9 of the peptide fragment A of Example 3, is synthesized and rendered radioactive (1–2×10$^9$ dpm/μg) as described in Example 6.

Size fractionated RNA is prepared as described in Example 5 except that 40 fractions of 0.3 ml are collected and the precipitated RNA is dissolved in 40 μl $H_2O$.

2×2 μl of this RNA are spotted on replica filters and baked at 80° C. The filters are prehybridized, then hybridized in the presence of 5×10$^7$ dpm of above oligodeoxynucleotide mixture 3 and washed as described in Example 6, except that the hybridization temperature is 37° C. By comparison of the replicas on X-ray film, fractions 12 and 13 are estimated to contain most MRP-14 mRNA.

EXAMPLE 8 cDNA cloning of MRP-8

8.1. Preparation of ds cDNA: 3 μg of 9S mRNA coding for MRP-8 from fraction 23 (see Example 6) are incubated for 90 min at 42° C. in a 50 μl reaction mixture containing 100 mM Tris-HCl (pH 8.3 measured at 42° C.), 10 mM $MgCl_2$, 140 mM KCl, 10 mM DTT, 1 mM of each dNTP, 100 μg/ml oligo-dT$_{12-18}$ (Pharmacia), 90 units RNasin™ (Genofit), 40 units AMV reverse transcriptase (Genofit) and 30 μCi of α-$^{32}$P-dCTP (3000 Ci/mmol). The reaction is stopped by addition of 2 μl 0.5M EDTA pH 7.5. The RNA is degraded by incubation with 25 μl of 0.15N NaOH for 1 h at 65° C. The solution is neutralized by addition of 25 μl Tris-HCl pH 8.0 and 6 μl 1N HCl. After addition of SDS to 0.5%, the solution is extracted with 100 μl phenol-chloroform (1:1) equilibrated with TNE buffer. The aqueous phase is passed over a 2 ml column containing Sephadex® G-50 (Pharmacia) in TNE buffer. 2×10$^6$ dpm $^{32}$P (1.6 μg) single stranded cDNA are recovered from the breakthrough fraction (0.4 ml) and precipitated by addition of 1 ml ethanol. The precipitate is collected by centrifugation and rendered double stranded in a 50 μl reaction mixture containing 100 mM Hepes pH 6.9, 10 mM $MgCl_2$, 2.5 mM DTT, 70 mM KCl, 0.5 mM of each dNTP and 40 units of DNA polymerase "large fragment" (Boehringer) overnight at 15° C. For digestion with S1 nuclease, the reaction is diluted with 30 μl $H_2O$, 20 μl of a solution containing 1M NaCl, 250 mM NaOAc pH 4.5, 5 mM $ZnSO_4$ and 2.5% glycerol, and 1 μl 1N HCl. After addition of 2 units S1 nuclease (Pharmacia) the mixture is incubated for 30 min at 30° C. The reaction is stopped by the addition of 5 μl 0.5M EDTA pH 7.5, 5 μl 1M Tris-HCl pH 8.3 and 5 μl 20% SDS, extracted with phenol-chloroform and chromatographed on Sephadex® G-50 as above. 2 µg of double stranded cDNA are recovered and precipitated with ethanol.

8.2. cDNA library in *E. coli*: The ds cDNA of Example 8.1 is extended with homopolymeric dC-tails in a 200 µl reaction mixture containing 200 mM potassium cacodylate pH 6.9, 1 mM CoCl$_2$, 1 mM DTT and 0.75 µM dCTP. After prewarming for 10 min at 30° C., 120 units terminal deoxynucleotidyl transferase (Pharmacia) are added and the mixture incubated for 15 min at 30° C. 4 µl of 0.5M EDTA pH 7.5 and 2 µl 20% SDS are added, and the DNA is extracted, chromatographed and precipitated as above. 40 ng (20 µl) of this dC-tailed cDNA are mixed with 8 µl (100 ng) of oligo-dG$_{10-20}$ tailed pUC9 DNA (Pharmacia) and 172 µl TNE buffer and sequentially incubated at 65° C. for 10 min, at 46° C. for 1 h, at 37° C. for 1 h and at room temperature for 1 h. The annealed cDNA plasmid DNA is used to transform competent *E. coli* HB 101 cells (strain LM 1035), which have been prepared for transformation as described by D. Hanahan, J. Mol. Biol. 1983, 166, 557. 1 µl of annealed DNA is added to 200 µl of competent cells and left on ice for 30 min. This procedure is performed 60 times. After a heat shock of 90 sec and chilling in ice for 2 min, 0.8 ml of SOC medium are added per tube which is then incubated for 60 min at 37° C. After the incubation all tubes are combined and plated out on 3 McConkey agar plates (12 cm) containing 25 µg/ml of ampicillin. The plates are incubated overnight at 37° C. The resulting 2500 recombinants per plate are lifted onto nylon membranes (Pall-Biodyne™) and two replicas made. The master filter is stored at 4° C. on an agar plate and the replicas are processed for colony hybridization as described in the Maniatis handbook.

8.3. Prescreening: The replica filters of Example 8.2 are prehybridized for 2 h at 32° C. in 100 ml of 2× Denhart's solution containing 0.9M NaCl, 0.18M Tris-HCl pH 8.0, 6 mM EDTA, 0.2% SDS and 50 µg/ml of denatured calf thymus DNA. Hybridization is performed for 36 h in 1 ml of the same solution containing 2×10$^7$ dpm oligonucleotide mixture 2 (Example 6) in a sealed plastic bag. After hybridization the filters are washed and exposed on a X-ray film overnight. Positives appear on both replica filters. The six positive colonies are grown up and their plasmid DNAs are isolated for restriction analysis.

The longest cDNA insert out of these 6 clones (approx. 500 base pairs, clone 3) is chosen to rescreen the same cDNA library and a second cDNA library, which is generated to obtain full length cDNA clones as follows:

8.4. Second cDNA library: 10 µl (1 mg/ml) of 9S mRNA coding for MRP-8 (fraction 23, Example 6) are incubated in a solution containing 25 µl RVT buffer, 2.5 µl of 20 mM dNTP mix, 5 µl of 1 mg/ml oligo-dT$_{12-18}$ (Pharmacia), 1 µl α-$^{32}$P-dCTP (10 µCi, 3000 Ci/mmol), 3 µl RNasin™ (60 units, Biotec), 3 µl AMV reverse transcriptase (66 units, Genofit), and 2 µl of H$_2$O. The mixture is incubated for 1.5 h at 42° C., then the reaction stopped by addition of 2 µl 0.5M EDTA pH 7.5. The RNA is degraded and the cDNA collected as in Example 8.1. The cDNA is extended with oligo-dC tails in a reaction mixture containing 32 µl cDNA (2.8 µg), 10 µl 1M potassium cacodylate pH 7.0, 5 µl 10 mM CoCl$_2$, 5 µl mM DTT and 10 µCi of $^3$H-dCTP (20 Ci/mmol, 10 µl lyophylized). After preincubation for 5 min at 37° C., 3 µl of terminal deoxynucleotidyl transferase (81 units, Pharmacia) are added and incubation is allowed to proceed for 10 min. 50 µl of TNE buffer are added and the solution is extracted with 0.1 ml phenol-chloroform mix. The cDNA is precipitated by addition of 0.2 ml ethanol and chilling in dry-ice. After centrifugation the pellet is washed with 70% ethanol, air-dried and dissolved in 13 µl of H$_2$O.

A solution of above cDNA in 13 µl H$_2$O, 25 µl RVT buffer, 2.5 µl of 20 mM dNTP mix, 5 µl 0.2 mg/ml oligo-dG$_{12-18}$ (Pharmacia), 3 µl α-$^{32}$P-dCTP (10 mCi/ml, 3000 Ci/mmol) and 3 µl of reverse transcriptase (66 units, Genofit) is incubated at 42° C. for 1.5 h. The reaction is stopped by addition of 2 µl 0.5M EDTA pH 7.5 and 50 µl TNE buffer, and the mixture is extracted with 0.15 ml phenol-chloroform mix. The aqueous phase is applied onto a Sephadex® G-50 column (2.5 ml in TNE buffer) and the breakthrough fraction (0.4 ml) by addition of 1 ml ethanol and chilling in dry-ice. The resulting containing 1.3 µg of ds cDNA is collected. The DNA is precipitated pellet is taken up in 32 µl H$_2$O and the DNA extended with oligo-dC tails as described above for single stranded cDNA. The reaction is stopped by addition of 1 µl 0.5M EDTA pH 7.5, and the sample loaded onto a horizontal 1% agarose gel in TBE buffer using slots with a width of 0.5 cm. After electrophoresis for 1 h at 5 V/cm, the region containing cDNA with an approximate size between 0.35 and 0.7 kb is excised and placed in two micro-collodion bags (Sartorius) and presoaked in H$_2$O. 0.3 ml H$_2$O are added and the bags are placed in an electrophoresis apparatus containing half-concentrated TBE buffer. The DNA is electroeluted at 5 V/cm electrode distance for 20 min and recovered from the bag by vigorous pipetting. After extraction with 0.6 ml phenol-chloroform mix, 40 µl of 3M NaOAc pH 5.5 and 1.2 ml ethanol are added and the solution chilled in dry-ice for 10 min. After centrifugation (5 min, Eppendorf centrifuge) 164 ng of ds cDNA are recovered and dissolved in 18 µl of 10 mM Tris-HCl pH 8.0 and 1 mM EDTA.

20 µl (27 ng) of above cDNA are annealed with 8 µl (100 ng) of oligo-dG$_{10-20}$ tailed pUC9 DNA (Pharmacia) and the resulting DNA used to transform competent *E. coli* HB 101 cells (strain LM 1035) as described above (Example 8.1) The resulting 2600 recombinants per plate are lifted onto nylon membranes (Pall-Biodyne™) and two replicas made. The master filter is stored at 4° C. on an agar plate and the replicas are processed for colony hybridization as described in the Maniatis handbook.

8.5. Screening: The cDNA insert from 1 µg plasmid of clone 3 (Example 8.3) is removed by digestion with HindIII and EcoRI restriction endonuclease and isolated by agarose gel electrophoresis and gel elution. The pure cDNA insert (100 ng) is rendered radioactive using a nick translation kit from Amersham (N.5000) following the instructions given by the supplier. The radioactive cDNA probe has a specific activity of 5×10$^8$ dpm/µg.

The replica filters of Example 8.4 are prehybridized for 2 h in 100 ml of 2× Denhart's solution containing 0.9M NaCl, 0.18M Tris-HCl pH 8.0, 6 mM EDTA, 0.2% SDS and 50 µg/ml of denatured calf thymus DNA. Hybridization is performed overnight in 1 ml of the same solution containing the heat-denatured nick-translated cDNA probe (60×10$^6$ dpm) in a sealed plastic bag. After hybridization the filters are washed in 200 ml of 0.9M NaCl, 0.18M Tris-HCl pH 8.0, 6 mM EDTA and 0.2% SDS, twice at 65° C., followed by two washes at 65° C. with 200 ml of 0.45M NaCl, 0.09M Tris-HCl pH 8.0, 3 mM EDTA and 0.2% SDS and two washes with 200 ml of 0.15M NaCl, 0.03M Tris-HCl pH 8.0, 1 mM EDTA and 0.2% SDS. The filters are exposed on an X-ray film over night and positives appear on both replica filters.

EXAMPLE 9 cDNA cloning of MRP-14

9.1. Preparation of ds cDNA: 20 µl (0.125 mg/ml) each of mRNA coding for MRP-14 from fractions 12 and 13

(Example 7) are incubated for 60 min at 42° C. in a solution containing 70 μl RVT buffer, 7 μl of 20 mM dNTP mix, 10 μl of 1 mg/ml oligo-dT$_{12-18}$ (Pharmacia), 3 μl RNasin™ (60 units, Biotec), 2 μl AMV reverse transcriptase (66 units, Genofit) and 7 μl α-$^{32}$P-dCTP (1 μCi, 3000 Ci/mmol). The reaction is stopped by addition of 6 μl 0.5M EDTA pH 7.5. The RNA is degraded by incubation with 3.75 μl of 1N NaOH for 1 h at 65° C. The solution is neutralized by addition of 25 μl Tris-HCl pH 8.0 and 6 μl 1N HCl. After addition of SDS to 0.5%, the solution is extracted with 100 μl phenol-chloroform (1:1) equilibrated with TNE buffer. The aqueous phase is passed over a 2 ml column containing Sephadex® G-50 (Pharmacia) in TNE buffer. 2×10$^5$ dpm $^{32}$P (1.0 μg) single stranded cDNA are recovered from the breakthrough fraction (0.4 ml) and precipitated by addition of 1 ml ethanol. The precipitate is collected by centrifugation.

The cDNA is extended with oligo-dC tails as described for MRP-8 cDNA in Example 8.4., then treated with dNTP mix, oligo-dG$_{12-18}$ α-$^{32}$P-dCTP and 3 μl of reverse transcriptase in RVT buffer at 37° C. for 60 min. After phenol-chloroform extraction, the aqueous phase is applied onto a Sephadex® G-50 column (2.5 ml in TNE buffer) and the breakthrough fraction (0.4 ml) containing 0.53 μg of ds cDNA is collected. The DNA is extended with oligo-dC tails, then loaded onto a horizontal 1% agarose gel in TBE buffer using slots with a width of 0.5 cm. After electrophoresis for 1 h at 5 V/cm, the region containing cDNA with an approximate size between 0.5 and 0.75 kb is excised and electroeluted as described in Example 8.4. 100 ng of ds cDNA are recovered and dissolved in 200 μl of 10 mM Tris-HCl pH 8.0 and 1 mM EDTA.

9.2. cDNA library in *E. coli:* 20 ng (20 μl) of dC-tailed ds cDNA of Example 9.1 are mixed with 30 μl (60 ng) of oligo-dG$_{10-20}$ tailed pUC-KO DNA and 20 μl tenfold concentrated TNE buffer and sequentially incubated at 65° C. for 10 min, at 46° C. for 1 h, at 37° C. for 1 h and at room temperature for 1 h. The pUC-KO plasmid is a derivative of pUC9 (available from Pharmacia) in which the promoter/operator region of the lac Z gene is deleted between the HaeII restriction site just outside the promoter sequence and the HindIII restriction site within the polylinker, leaving the other sequences of the pUC9 plasmid unchanged. The annealed cDNA plasmid DNA is used to transform competent *E. coli* HB 101 cells (strain LM 1035) as described in Example 8.2 for MRP-8 cDNA. From 6 McConkey agar plates each containing 2500 recombinants two replicas are made. The master filters on nylon membranes are stored at 4° C. on an agar plate and the replicas are processed for colony hybridization.

9.3. Screening: The replica filters of Example 9.2 are hybridized at 37° C. in a solution containing 2×10$^7$ dpm of the oligodeoxynucleotide mixture 3 of Example 7 in a sealed plastic bag as described under prescreening in Example 8.3. The positive colonies are grown up and their plasmid DNAs are isolated for restriction analysis.

A recombinant plasmid named pMRP-14-10 containing an insert of approx. 500 nucleotides is chosen to rescreen the same cDNA library. The cDNA insert from 1 μg plasmid of this clone pMRP-14-10 is removed by digestion with HindIII and EcoRI restriction endonuclease and rendered radioactive (specific activity of 5×10$^8$ dpm/μg) using a nick translation kit. This probe is used to screen once more the replica filters of Example 9.2 as described in Example 8.5. Positives appear on both replica filters.

EXAMPLE 10

DNA sequence coding for MRP-8

Figure 2:
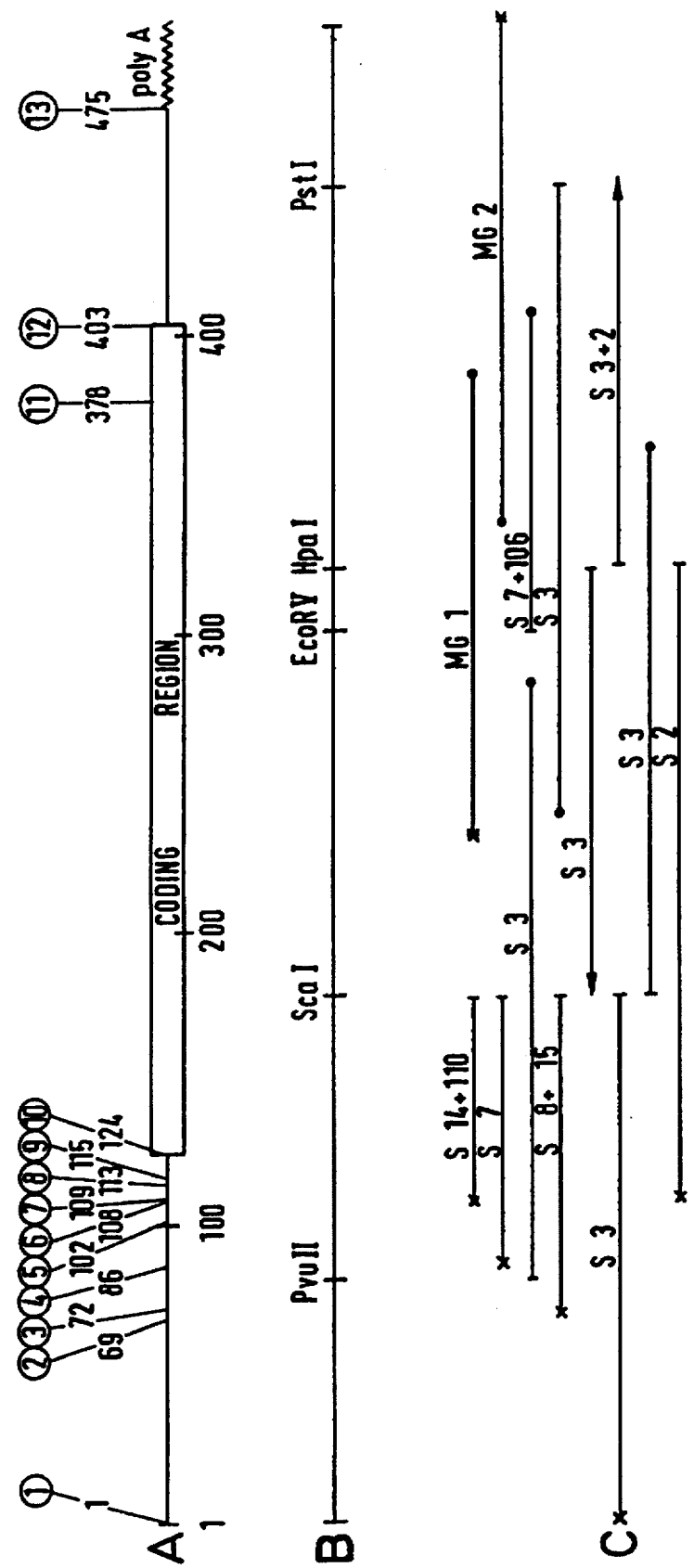
FIG. 2 gives a schematic representation of the cDNA of MRP-8 of formula VII isolated from clone 3. In part A, the coding region is shown. The encircled numbers refer to base positions at which cDNA isolated from other clones differ from the cDNA of clone 3 and to other special features discussed in Example 10. Lane B shows the positions of restriction sites used for sequencing. Part C summarizes the sequence strategy showing start (vertical line) and end (arrowhead) of sequence at restriction site, end of clear sequence (dot) and end of DNA of the respective clone (cross). Numbers refer to the different clone numbers, letters to the method of sequencing (S: Sanger, MG: Maxam and Gilbert).

The cDNA insert of clone 3 (Example 8.3) and a number of cDNA inserts from positive clones of Example 8.5 are chosen for the determination of the full nucleotide sequence using the well-known methods of Sanger and of Maxam and Gilbert. The sequence of the coding region is determined on both strands and restriction sites used in the sequencing strategy determined on overlapping fragments as well. The strategy is summarized in FIG. 2 (Part C), and restriction sites given (Part B). The coding cDNA sequence of clone 3 (and the amino acid sequence for which it codes) is given in formula VII. Part A of FIG. 2 schematically represents the full sequence of this cDNA. Special features and discrepancies between this cDNA of clone 3 and other clones are indicated by the numbers and are listed below:

1. Position 1: end of clone 3, the sequence up to position 68 is only present in clone 3 and is not found in the gene.
2. Position 69: ends of clones 8 and 15; an A in clones 3 and 8 and a T in clone 15.
3. Position 72: 6-base change from GGCAAA in clone 3 to TCTCTT in clones 8 and 15.
4. Position 86: end of clone 7.
5. Position 102: 17-base insertion AAGGTTCT-GTTTTTCAG in clone 15.
6. Position 108: end of clone 14.
7. Position 109: end of clones 2 and 110.
8. Position 113: insertion of a T in clones 7, 8, 14 and 15.
9. Position 115: base change to a T in clones 2 and 110.
10. Position 124: start of the coding region.
11. Position 378: insertion of AA in clone 2 not found in the gene.
12. Position 403: end of the coding region.
13. Position 475: start of the poly-A tail.

EXAMPLE 11

DNA sequence coding for MRP-14

Figure 3:
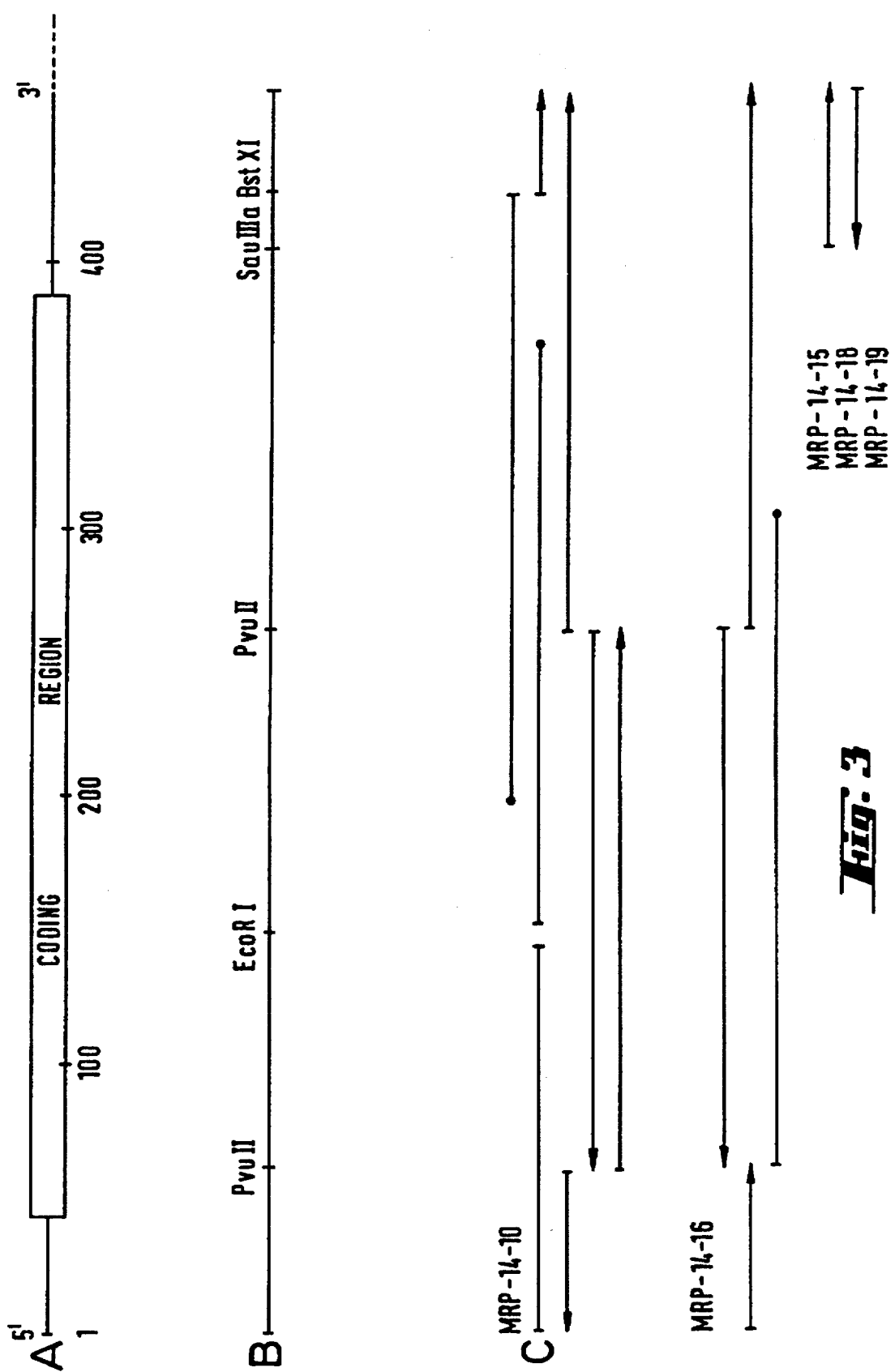
FIG. 3 gives a schematic representation of the cDNA of MRP-14 of formula IX with the coding region (lane A), position of restriction sites used for sequencing (lane B) and sequence strategy (lane C) applied to clone MRP-14-10, clone MRP-14-16 and clones MRP-14-15, 18 and 19 (Example 11). The figure displays start (vertical line) and end (arrowhead) of sequencing and end of clear sequence (dot).

The cDNA insert of two clones (Example 9.3, pMRP-14-10 and pMRP-14-16) are chosen for the determination of the full nucleotide sequence. The strategy is summarized in FIG. 3. The coding cDNA sequence of these clones (and the amino acid sequence for which it codes) is identical and is given in formula IX.

Three more clones (pMRP-14-15, 18 and 19) are analyzed at the 3'-end. All display identical sequences as depicted in formula IX, thus lacking the natural 3'-end of the mRNA.

EXAMPLE 12

Expression of MRP-8 in *E. coli* under control of the trp promoter

An expression vector for *E. coli* containing a trp promoter and a DNA insert coding for MPR-8 is prepared essentially as described for the corresponding Eglin C expression vector in European Patent Application EP 146 785.

12.1. Vector preparation: 20 μg of plasmid pHRi 148 (EP 146 785) are digested to completion using BamHI. The ends are dephosphorylated using 3 units of calf intestinal alkaline phosphatase. The DNA is extracted with phenol-chloroform mix, then digested to completion using EcoRI. The vector DNA is isolated by agarose gel electrophoresis and electroelution as described above for cDNA in Example 8.4. The vector DNA is dissolved in H$_2$O at a concentration of 0.5 μg/ml.

12.2. Linker preparation: Oligodeoxynucleotides 5'-AATTCATGCTGACTGAGC-3' and

5'-TCAGTCAGCATG-3' are synthesized using standard procedures (H. Rink et al., Nucleic Acid Research 1984, 12, 6369). 2 µg of the shorter oligodeoxynucleotide are phosphorylated using ATP and polynucleotide kinase and ligated to 2 µg of the unphosphorylated larger oligodeoxynucleotide with DNA ligase. Following ligation the dsDNA is digested to completion with AluI. The DNA is extracted with phenol-chloroform mix, precipitated with ethanol and dissolved in 10 µl $H_2O$.

12.3. Preparation of the insert DNA: 20 µg of clone 3 cDNA (Example 8.3) is digested to completion with BamHI and PvuII, and the cDNA insert of approx. 480 bp isolated by agarose gel electrophoresis and gel elution. 3 µg of this DNA fragment are digested partially with AluI, and a fragment of approx. 430 bp isolated as above. 70 ng of this DNA are ligated to 8 µl of the linker DNA solution of Example 12.2 in 8 µl $H_2O$. The resulting DNA is digested to completion with EcoRI and BamHI, and the resulting fragment of approx. 440 bp isolated by PAGE and electroelution.

12.4. Vector and insert ligation: 0.5 µg of the vector of Example 12.1 and 50 ng of the insert-linker DNA of Example 12.3 are ligated. The resulting DNA is used to transform competent E. coli HB 101 cells (strain LM 1035) as described above (Example 8.2). A recombinant pMRP-8-trp displaying the expected restriction enzyme pattern and DNA sequence of the insert is chosen for the expression of MRP-8.

12.5. Fermentation: E. coli containing pMRP-B-trp (Example 12.4) is grown overnight at 37° C. in 200 ml of medium containing 7 g $Na_2HPO_4$, 3 g $KH_2PO_4$, 0.5 g NaCl, 1 g $NH_4Cl$, 5 g glucose, 0.02 g $CaCl_2$, 0.25 g $MgSO_4$, 25 g casamino acids, 0.1 g thiamine and 50 mg ampicillin per liter. The culture is diluted with 800 ml of the same, prewarmed medium supplemented with 12.5 µg/ml β-indole-acrylic acid. After 4.5 h, the optical density $OD_{650}$ reaches 1.3. The cells are collected by centrifugation. Control cultures using E. coli containing pHRi148 are processed in the same way.

12.6. Lysozyme extract: The bacterial pellet is resuspended in 50 ml of 50 mM Tris-HCl pH 8.0, 30 mM NaCl and 1 mg/ml chicken egg-white lysozyme. The suspension is kept 1 h on ice. 0.1 mM PMSF are added and the cells are broken by three cycles of freezing in liquid nitrogen and thawing at 37° C. The lysate is cleared by centrifugation for 30 min at 17000 rpm in a SS34 rotor (Sorvall) at 4° C.

12.7. Urea-sonified extract: 22.5 ml of a cell suspension ($OD_{650}$=20) in 50 mM Hepes pH 8.0, 30 mM NaCl and 0.1% ethanolamine prepared from a bacterial pellet of Example 12.5 are mixed with 18 g of urea. The suspension is sonified 3×30 sec with 30 sec intervalls with a MSE Soniprep® 150 using a 9.5 mm probe and 24 micron amplitude. The lysate is cleared by centrifugation at 17000 rpm in a Sorvall SS34 rotor for 30 min at 20° C. The supernatant is made 0.1 mM in $CaCl_2$, $MgCl_2$, $CoCl_2$, $ZnCl_2$, $MnCl_2$, $CuSO_4$ and $FeSO_4$ and dialysed against three changes of 10 mM Hepes pH 7.5, 130 mM NaCl and 0.1 mM of the same salts as above. The dialysate is cleared by centrifugation as in Example 12.6.

EXAMPLE 13

Expression of MRP-14 in E. coli under control of the trp promoter

An expression vector for E. coli containing a trp promoter and a DNA insert coding for MPR-14 is prepared essentially as described in Example 12.

13.1. Linker preparation: The following oligodeoxynucleotides are synthesized using standard procedures (H. Rink et al., Nucleic Acid Research 1984, 12, 6369): (1) 5'-AATTCATGACTTGCAAAATGTCGCAG-3', (2) 5'-CTGCGACATTTTGCAAGTCATG-3', (3) 5'-AATTCATGTCGCAG-3' and (4) 5'-CTGCGACATG-3'. The oligodeoxynucleotides 1 and 3 are phosphorylated using ATP and polynucleotide kinase according to standard procedures. Equimolar mixtures of phosphorylated oligodeoxynucleotide 1 and unphosphorylated oligodeoxynucleotide 2 as well as of phosphorylated oligodeoxynucleotide 3 and unphosphorylated oligodeoxynucleotide 4 are made. Mixture 1–2 is used for the construction of plasmids expressing MRP-14, mixture 3–4 is used for the construction of plasmids expressing MRP-14d, which lacks the first four aminoacids of MRP-14.

13.2. Vector preparation: 1 µg each of vector DNA from plasmid pHRi 148 prepared as in Example 12.1 is ligated to 50 pmol of the linker mixtures 1–2 and 3–4, respectively, of Example 13.1. The vector DNA is separated from the free linkers by agarose gel electrophoresis and gel elution. 10 µg of clone pMRP-14-10 cDNA (Example 9.3) is digested to completion with BamHI and PvuII, and the cDNA insert of approx. 430 bp isolated by agarose gel electrophoresis and gel elution. 25 ng each of this cDNA insert are ligated to 0.2 µg of the vector-linker 1–2 (for MRP-14) and 0.2 µg of the vector-linker 3–4 (for MRP-14d), respectively. The resulting DNAs are used to transform competent E. coli HB 101 cells (strain LM 1035) as described above. Recombinants pMRP-14-trp and pMRP-14d-trp displaying the expected restriction enzyme pattern and DNA sequence of the insert are chosen for the expression of MRP-14 and MRP-14d, respectively.

13.3. Fermentation of transformed E. coli and MRP-14 extraction: E. coli containing pMRP-14-trp or pMRP-14d-trp (Example 13.2) are grown and processed as described in Example 12.3.

The cells are treated with lysozyme or broken by sonification in urea solution and the lysate worked up as described in Examples 12.6 and 12.7.

EXAMPLE 14

Expression of MRP-8 in E. coli under control of the promoter $P_L$ of phage λ

14.1. Vector construction: Plasmid pPLc24 (E. Remaut, P. Stanssens and W. Fiers, Gene 1981, 15, 81) is digested with EcoRI, then treated with Klenow polymerase and dNTP mix in order to render the ends blunt-ended. The DNA is digested with BamHI, and the resulting vector DNA isolated by agarose gel electrophoresis and electroelution. pMRP-8-trp DNA (Example 12.4) is digested to completion with BamHI and digested partially with HpaI. The fragment of approx. 440 bp is isolated by agarose gel electrophoresis and electroelution. The fragment is ligated to the vector DNA derived from pPLc24 and the resulting DNA used to transform wild type E. coli K12. The transformants are plated out on L-plates containing 40 µg of ampicillin. Standard sequence analysis of recombinants is performed to ensure the correctness of the constructions. DNA of a correct construction is used to transform E. coli strains W3110 and HB101, both harbouring λcI857 (Remaut et al., loc. cit.). The transformants are plated out on L-plates containing 40 µg/ml of kanamycin and ampicillin. Resulting recombinants pMRP-8-$P_L$ are used for fermentation.

14.2. Fermentation: Recombinants pMRP-8-$P_L$ are grown at 30° C. overnight in LB medium containing 40 µg/ml of ampicillin and kanamycin. The cultures are diluted 1:5 with the same medium and incubated at 42° C. for 2.5 h. The cells are lysed as described in Examples 12.6 or 12.7.

EXAMPLE 15

Expression of MRP-14 and MRP-14d in *E. coli* under control of the promoter $P_L$ of phage λ

Vectors are constructed from pMRP-14-trp and pMRP-14d-trp DNA (Example 13.2), respectively, and plasmid pPLc24 and used to transform *E. coli* K12, W3110 and HB101 as described in Example 14.1. Resulting recombinants pMRP-14-$P_L$ and pMRP-14d-$P_L$ are grown in LB medium and lysed as described in Example 14.2.

EXAMPLE 16

Construction of a plasmid for MRP-8 expression in *S. cerevisiae*

16.1. Isolation of the pJDB207 vector fragment: 6 µg of plasmid pJDB207R/PHO5-TPA12-2 (European Patent Application EP 143 081) are digested to completion with restriction endonuclease BamHI. The resulting DNA fragments of 6.8 kb and 2.4 kb in size are precipitated by ethanol and resuspended in 400 µl of 50 mM Tris-HCl pH 8.0. 4.5 units of calf intestine alkaline phosphatase (Boehringer, Mannheim) are added. The mixture is incubated for 1 h at 37° C. Subsequently, the phosphatase is inactivated by incubation at 65° C. for 1.5 h. The solution is adjusted to 150 mM NaCl. The DNA solution is applied to a 100 µl bed of DE52 (Whatman) anion exchanger equilibrated with 10 mM Tris-HCl pH 7.5 containing 150 mM NaCl and 1 mM EDTA. After washing with the same buffer, the DNA is eluted with 400 µl of 1.5M NaCl, 10 mM Tris-HCl pH 7.5 and 1 mM EDTA and precipitated by ethanol. The large 6.85 kb BamHI fragment is separated from the small fragment on a 1% agarose gel in TBE buffer. The DNA fragment is electroeluted from the gel, purified by DE52 anion exchange chromatography (see above), precipitated with ethanol and resuspended in $H_2O$ at a concentration of 0.1 pmol/µl.

16.2. Isolation of a 534 bp PHO5 promoter fragment: 10 µg plasmid p31/R (European Patent Application EP 100 561) are digested with EcoRI and BamHI. The resulting 3 fragments are separated on a 1.2% agarose gel in TBE buffer. The 534 bp BamHI-EcoRI fragment comprises the PHO5 promoter. The DNA fragment is electroeluted from the gel, purified by DE52 chromatography, ethanol precipitation and resuspended at a concentration of 0.1 pmol/µl.

16.3. Isolation of a 0.4 kb DNA fragment coding for MRP-8: 10 µg of plasmid pMRP-8-trp (Example 12.4) are digested with BamHI and EcoRI. The resulting two DNA fragments are separated on a 1.2% agarose gel. The 0.4 kb fragment is isolated as above and resuspended in $H_2O$ at a concentration of 0.1 pmol/µl.

16.4. Ligation of DNA fragments: 0.1 pmol (0.45 µg) of the 6.8 kb BamHI vector fragment, 0.2 pmol (70 µg) of the 534 bp BamHI-EcoRI PHO5 promoter fragment and 0.2 pmol (52 ng) of the 0.4 kb EcoRI-BamHI fragment of pMRP-8-trp are ligated in 15 µl of 60 mM Tris-HCl pH 7.5, 10 mM $MgCl_2$, 10 mM DTT, 1 mM ATP with 600 units of $T_4$ DNA ligase (Biolabs) at 15° C. for 6 h. A 1 µl aliquot of the ligation mixture is added to 100 µl of calcium treated, transformation competent *E. coli* HB101 cells. 12 transformed, ampicillin resistant colonies are grown individually in LB medium containing 100 µg/ml of ampicillin. Plasmid DNA is prepared according to the method of Holmes et al. (Anal. Biochem. 1981, 114, 193) and analyzed by BamHI and HindIII/EcoRI digests. The appearance of a 780 bp EcoRI-HindIII fragment indicates the correct orientation of the PHO5 promoter-MRP-8 DNA insert. Such a clone is isolated and referred to as pJDB207R/PHO5-MRP-8.

EXAMPLE 17

Construction of plasmids for MRP-14 and MRP-14d expression in *S. cerevisiae*

Plasmids for MRP-14 and MRP-14d expression in *Saccharomyces cerevisiae* are prepared from plasmid pJDB207R/PHO5-TPA12-2 and 0.4 kb EcoRI-BamHI fragments of pMRP-14-trp and pMRP-14d-trp (Example 13.2), respectively, as described in Example 16.

Transformed, ampicillin resistant colonies of *E. coli* HB101 cells are grown individually in LB medium containing 100 µg/ml of ampicillin. Plasmid DNA is prepared and analysed by BamHI and HindIII/EcoRI digestion. The appearance of a 780 bp EcoRI-HindIII fragment indicates the correct orientation of the PHO5 promoter-MRP-14 or -MRP-14d DNA insert. Such clones are isolated and referred to as pJDB207R/PHO5-MRP-14 and pJDB207R/PHO5-MRP-14d, respectively.

EXAMPLE 18

Transformation of *Saccharomyces cerevisiae* GRF18

Plasmids pJDB207R/PHO5-MRP-8, pJDB207R/PHO5-MRP-14 and pJDB207R/PHO5-MRP-14d are introduced into *Saccharomyces cerevisiae* strain GRF18 (α, his 3-11, his 3-15, leu 2-3, leu 2-112, $kan^R$) using the transformation protocol described by Hinnen et al. (Proc. Natl. Acad. Sci. USA 1978, 75, 1929). Transformed yeast cells are selected on yeast minimal media plates deficient in leucine. Single transformed yeast colonies are isolated and referred to as *Saccharomyces cerevisiae* GRF18/pJDB207R/PHO5-MRP-8, GRF18/pJDB207R/PHO5-MRP-14 and GRF18/pJDB207R/PHO5-MRP-14d.

EXAMPLE 19

Fermentation of transformed yeast strains

Cells of the above transformed yeast strains *Saccharomyces cerevisiae* GRF18/pJDB207R/PHO5-MRP-8, GRF18/pJDB207R/PHO5-MRP-14 and GRF18/pJDB207R/PHO5-MRP-14d are grown in 50 ml of yeast minimal medium (Difco Yeast Nitrogen Base without amino acids to which 2% glucose and 20 mg/l L-histidine are added) with shaking at 30° C. for 25 h to a density of $3 \times 10^7$ cells/ml. The cells are washed in 0.9% NaCl and used to inoculate 100 ml of low $P_i$ minimal medium prepared according to the recipe of the Difco Yeast Nitrogen Base medium (without amino acids) with 0.03 g/l $KH_2PO_4$, 1 g/l KCl, 10 g/l L-asparagine instead of $(NH_4)_2SO_4$, 2% glucose and 1 g/l L-histidine. The medium is inoculated to a starting $OD_{600}$ of 0.25. The cells are grown at 30° C. for 24 h and harvested at an $OD_{600}$ of 2.

Cells of 35 ml of low $P_i$ medium are collected by centrifugation and resuspended in a total volume of 4 ml of cold 66 mM sodium phosphate buffer pH 7.4 and 0.1% (v/v) Triton® X-100. The cell suspension is transferred to a 30 ml Corex tube, 8 g of glass beads (0.4 mm in diameter) are added and the suspension is shaken on a Vortex Mixer (Scientific Instruments Inc., USA) at full speed for 4 min and then cooled in an ice bath. More than 90% of the cells are broken by this procedure. Cell debris and glass beads are sedimented by centrifugation for 10 min at 8000 rpm at 4° C. in a Sorvall HB-4 rotor. The supernatant is transferred to Eppendorf tubes, frozen in liquid nitrogen and stored at −60° C.

EXAMPLE 20

Isolation and purification of MRP-8

20.1. DEAE ion exchange chromatography: 72 ml of crude lysate of Example 12.6 is dialysed (Spectrapor® membrane No. 3, 3.5 kD cutoff, Spectrum Medical Industries) against 20 mM Tris-HCl, 0.01% DTT pH 8.5. The dialysed solution is pumped onto a DEAE Trisacryl® M (LKB) ion exchange column (2.6×10 cm) equilibrated with the dialysis buffer. After loading of the sample the column is washed with dialysis buffer (80 ml) until the UV 254 nm absorption reaches baseline level (Uvicord® S, LKB). Proteins bound to the column are eluted using a linear gradient of NaCl in dialysis buffer ranging from 0.0M to 0.2M NaCl, then dialysis buffer/0.2M NaCl (80 ml) and dialysis buffer/1.0M NaCl (200 ml) at a flow rate of 1.8 ml/min (peristaltic pump P-I, Pharmacia). Individual 9 ml fractions (collected with a Ultrorac® II, LKB) are analyzed by SDS-PAGE [U. K. Laemmli, Nature 1970, 227, 680] on 15% polyacrylamide slab gels and pooled according to their MRP-8 content. The pool of fractions eluting between 180–380 μS (Bio Rad conductivity monitor) is concentrated by ultrafiltration (YM-10 membrane, Amicon) to a volume of 5.5 ml.

Samples of crude lysate of Example 12.7, 14.2 and 19 containing MRP-8 are processed likewise.

20.2. Size exclusion chromatography: The concentrated pool from Example 20.1 is separated with a TSK G 3000 SWG high performance gel filtration column (LKB) equilibrated in 30 mM NaOAc and 150 mM NaCl pH 6.5 on a HPLC system consisting of a HPLC pump 2150, a 2 channel recorder 2210 from LKB and a HPLC UV detector Spectroflow® 757 from Kratos. The maximal sample volume applied is 2 ml, the flow rate 3 ml/min, and fractions are collected automatically every minute (fraction collector Superrac® 2211, LKB). Based on the analysis by SDS-PAGE, the fractions eluting between an elution volume of 163 ml and 182 ml are pooled and concentrated to a volume of 6 ml by ultrafiltration as above.

20.3. High resolution ion exchange chromatography on a Mono Q® column: 0.8 ml of the concentrated pool of Example 20.2 is diluted with 3 ml water and adjusted to pH 8.5 with dilute ammonia. This solution is applied to a Mono Q® HR 5/5 column (FPLC, Fast Protein, Polypeptide, Polynucleotide Liquid Chromatography system, Pharmacia) equilibrated in 20 mM diethanolamine-HCl pH 8.5. The column is washed with 12 ml diethanolamine buffer and the proteins eluted with a linear NaCl gradient in the same buffer ranging from 0.0M NaCl to 0.125M NaCl over 21 min at a flow rate of 1.5 ml/min. Fractions of individual peaks are collected manually according to the UV 280 nm elution pattern.

20.4. Sulfopropyl ion exchange chromatography: As an alternative to the purification with size exclusion chromatography and Mono Q® ion exchange chromatography (Examples 20.2 and 20.3) the concentrated pool from Example 20.1 (52 ml containing approx. 250 mg protein) is dialysed against 50 mM NaOAc/0.01% DTT, pH 5.5 (starting buffer) and pumped onto a SP Trisacryl® M (LKB) ion exchange column (2.5×10 cm) equilibrated in the same buffer. The column is washed with more buffer until the UV 254 nm absorption reaches baseline level. Proteins bound to the column are eluted using a linear gradient of NaCl in starting buffer ranging from 0.0M to 0.5M NaCl (300 ml), then starting buffer/0.5M NaCl (100 ml) and starting buffer/1.0M NaCl (100 ml) at a flow rate of 2.0 ml/min. MRP-8 is eluted between 0.25M–0.35M NaCl. Purity as judged by SDS-PAGE is greater than 90% at this stage.

20.5. Reversed phase HPLC: The protein fraction of Example 20.3 or 20.4 is further purified on a Vydac® 218 TP 5415 reversed phase HPLC column (The Separations Group, Hesparia, Calif., USA) using a Varian 5000 liquid chromatograph. The column is equilibrated in a mixture of 65% TFA 0.1% in water and 35% TFA 0.07% in acetonitrile. 5 min after sample injection, a linear gradient of 12 min is started ending at 45% TFA 0.1% in water and 55% TFA 0.07% in acetonitrile at a flow rate of 1 ml/min. The eluate is monitored for UV absorbance at 215 nm.

MRP-8 is eluted in 2 separate peaks with retention times of 14.5 min and 15.8 min, respectively. As shown by SDS-PAGE under reducing and non-reducing conditions, the faster eluting material represents the monomeric form of MRP-8 (apparent molecular weight 8 kD), whereas the second peak consists of the dimeric disulfide-linked derivative of MRP-8 (apparent molecular weight 16 kD).

EXAMPLE 21

Characterization of MRP-8

21.1. Amino acid sequence analysis: The purified MRP-8 of Example 20 is subjected to N-terminal amino acid sequence analysis using a gas-phase protein sequencer model 470 (Applied Biosystems) according to the method of M. W. Hunkapillar and L. E. Hood, Methods in Enzymology 1983, 91, 399. The anilino-thiazolinone derivatives are rearranged to phenylthiohydantoin (PTH) amino acids by treatment with 25% aqueous TFA at 50°. The PTH amino acids are analyzed on a Zorbax CN® HPLC column (DuPont, 200×4.6 mm) [R. Knecht et al., Anal. Biochem. 1983, 130, 65]. The following N-terminal amino acid sequence is found:

$$\text{Met—Leu—Thr—Glu—Leu—Glu—Lys—Ala—Leu—Asn—Ser—Ile—Ile—Asp—Val—Tyr—X}_{17}\text{—}$$
$$\text{Lys—Tyr—Ser—Leu—Ile—Lys—Gly—Asn—Phe—X}_{27}\text{—Ala—Val—Tyr—X}_{31}\text{—Asp—Asp—Leu—}$$
$$\text{Lys—Lys—Leu—Leu—Glu—Thr—Glu—X}_{42}\text{—Pro—Gln—Tyr—Ile—X}_{47}\text{—Lys—Lys—Gly—Ala—}$$
$$\text{Asp—Val—Trp—Phe—Lys—.}$$

$X_{17}$, $X_{27}$, $X_{31}$, $X_{42}$ and $X_{47}$ represent non-determined amino acids. This sequence is in accord with the sequence of formulas I or VII determined by cDNA analysis (Example 10).

21.2. Reversed phase HPLC: Analytical reversed phase HPLC is performed on a Vydac® 218 TP-B5-5μ (4.0×120 mm) column with human MIF 8 kD of EP 162 812, MRP-8 of Example 20 and a mixture thereof using a linear 30 min gradient from 65% TFA 0.1% in water and 35% TFA 0.08% in acetonitrile to 45% TFA 0.1% in water and 55% TFA 0.08% in acetonitrile at a flow rate of 1 ml/min. Human MIF 8 kD and MRP-8 are indistinguishable under these conditions and elute with a retention time of 11.2 min (UV absorbance at 215 nm).

21.3. Size exclusion chromatography: MRP-8 and the dimeric disulfide-linked MRP-8 derivative of Example 20 are chromatographed on a Shimpack® Diol 150 high performance size exclusion chromatography column (Shimadzu, 7.9×500 mm) in 30 mM Tris-HCl and 150 mM NaCl pH 7.0 at a flow rate of 1 ml/min. The UV absorption is measured at 215 nm. Monomeric MRP-8 is eluted after 16.4 min with an apparent molecular weight of 30 kD and the dimeric MRP-8 derivative after 15.1 min with an apparent molecular weight of 42 kD when compared to standard molecular weight markers cytochrome c (12 kD), myoglobin (17 kD), carbonic anhydrase (30 kD), ovalbumin (45 kD) and BSA (66.2 kD).

21.4 Mass spectroscopy: The molecular weight of MRP-8 is determined with the Fast Atom Bombardment (FAB-MS) method according to M. Barber et al. (Nature 1981, 293, 270) on a ZAB-SE spectrometer (VG Analytical Ltd., Manchester, GB) at 8 kV. Ionisation is achieved with a cesium gun at 35 kV. Thioglycerol containing 0.1% TFA is used as a matrix.

M (calculated): 10'832.53

M (found): 10'833.6±2.1 (mean of 4 measurements).

Aliquots of MRP-8 are digested with 1/10 the amount of either trypsin, chymotrypsin or V8 protein from *Staphylococcus aureus* in 50 mM $NH_4HCO_3$. V8 fragments are converted to methyl esters with 1.25N HCl in methanol 1 h at room temperature. Trypsin fragments (50 µg) are oxidized with 50 µl performic acid (1 part 30% $H_2O_2$ and 19 parts HCOOH) for 2 h at room temperature. FAB-MS of underivatized, esterified and oxidized fragments allows the unequivocal identification of the MRP-8 fragments comprising amino acids 1 to 16, 19 to 41, 57 to 70 and 72 to 77, respectively.

EXAMPLE 22

Isolation and purification of recombinant MRP-14

22.1. DEAE ion exchange chromatography: 90 ml of crude lysate of Example 13.3 from *E. coli* containing pMRP-14-trp is dialysed and purified on a DEAE Trisacryl® M (LKB) ion exchange column (5×10 cm) as described in Example 20.1. MRP-14 elutes at a concentration of 0.12 to 0.15M NaCl in 20 mM Tris-HCl, 0.01% DTT, pH 8.5 (dialysis buffer). Samples of crude lysate of Example 15 and 19 containing MRP-14 are processed likewise. 22.2. Sulfopropyl ion exchange chromatography: The pool of recombinant MRP-14 containing fractions from Example 22.1 (68 ml) is acidified to pH 5.5 with 10% acetic acid and pumped onto a SP Trisacryl® M (LKB) ion exchange column (2.5×10 cm) equilibrated with 50 mM NaOAc/0.01% DTT, pH 5.5 (starting buffer). The column is washed with starting buffer until the UV 254 nm absorption reaches baseline level. Proteins bound to the column are eluted using a linear gradient of NaCl in starting buffer ranging from 0.0M to 0.5M NaCl, then starting buffer/0.5M NaCl (80 ml) and starting buffer/1.0M NaCl (200 ml) at a flow rate of 1.7 ml/min. Individual 17 ml fractions are collected and analyzed by SDS-PAGE. Recombinant MRP-14 from pooled fractions is judged to be more than 90% pure at this stage according to SDS-PAGE.

22.3. Reversed phase HPLC: Recombinant MRP-14 of Example 22.2 is further purified on a HPLC column (0.4×12 cm) packed with 218 TP-B5-5µ (The Separations Group). The equipment and conditions of Example 1.1 are used. Thus, at a linear 30 min gradient of 65 to 45% TFA 0.1% in water and 35 to 55% TFA 0.07% in acetonitrile and a flow rate of 1 ml/min, MRP-14 is eluted after 13.8 min. Dimeric, disulfide-linked MRP-14 elutes after 16.2 min. This dimer can be converted to monomeric MRP-14 by treatment with 0.2% DTT for 15 min at room temperature.

22.4. Amino acid sequence analysis: The purified MRP-14 of Example 22.3 is subjected to N-terminal amino acid sequence analysis as described in Example 21.1. The following N-terminal amino acid sequence is found:

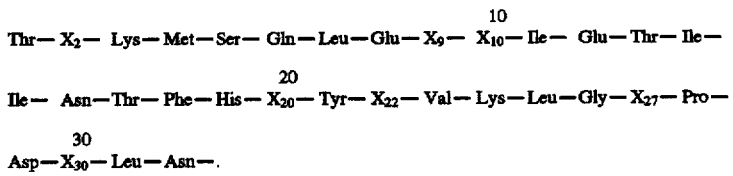

$X_2$, $X_9$, $X_{10}$, $X_{20}$, $X_{22}$, $X_{27}$ and $X_{30}$ represent non-determined amino acids. The amino acid methionine expected at the N-terminal of MRP-14 has obviously been cleaved by the *E. coli* host harbouring pMRP-14-trp.

22.5. Mass spectroscopy: FAB-MS was performed as described in Example 21.4:

M (calculated, first amino acid Thr): 13'110.94

M (found): 13'112.8 (accumulated signal of 3 individual analyses).

FAB-MS of trypsin, chymotrypsin and V8 digests allowed the unequivocal identification of the MRP-14 fragments comprising amino acids 10 to 19, 23 to 52, 58 to 77 and 79 to 93.

EXAMPLE 23

Isolation and purification of recombinant MRP-14d 23.1. DEAE ion exchange chromatography: 320 ml of crude lysate of Example 13.3 from *E. coli* containing pMRP-14d-trp is dialysed and loaded on a DEAE Trisacryl® M ion exchange column (2.6×10 cm) as described in Example 20.1. The column is washed with 80 ml dialysis buffer, then eluted using a linear gradient of NaCl in dialysis buffer ranging from 0.0M to 0.2M NaCl. MRP-14d is eluted between 0.08 and 0.19M NaCl.

23.2. Sulfopropyl ion exchange chromatography: The combined fractions containing recombinant MRP-14d from Example 23.1 (70 ml) are acidified to pH 5.5 and loaded onto a SP Trisacryl® M ion exchange column as described in Example 22.2. MRP-14d is eluted using a linear gradient of 0.0M to 0.5M, then 0.5M and 1.0M NaCl in starting buffer as above and judged to be more than 95% pure according to SDS-PAGE.

23.3. Amino acid sequence analysis: The purified MRP-14d of Example 23.2 is subjected to N-terminal amino acid sequence analysis as described in Example 21.1. The following N-terminal amino acid sequence is found:

```
            5                              10
Ser— Gln— Leu— Glu— Arg— Asn— Ile— Glu— Thr— Ile— Ile— Asn— Thr— Phe—

15                      20                     25
His— Gln— Tyr— Ser— Val— Lys— Leu— Gly— His— Pro— Asp— Thr— Leu— Asn—

30                  35
Gln— Gly— Glu— Phe— Lys— Glu— Leu— Val—.
```

The amino acid methionine expected at the N-terminal of MRP-14d is missing.

EXAMPLE 24

Human genomic DNA coding for MRP-8

24.1. Isolation of human placenta genomic DNA: A human placenta is minced to powder by freezing tissue slices in liquid nitrogen and crushing in a mortar. The DNA is isolated by gently lysing several aliquots of 2 ml of this fine tissue powder in 30 ml of 0.1M EDTA, 0.1M Tris-HCl pH 7.5, 1% sarkosyl, 0.3M β-mercaptoethanol and 100 µg/ml proteinase K at 50° C. for 2 h on a rotary disk. In order to avoid formation of clumps, the powder is passed through a fine sifter prior to addition to the lysis buffer. 28 g CsCl and 10 mg ethidium bromide are added and the DNA banded by equilibrium Centrifugation in a VT50 Beckman rotor at 49000 rpm for 36 h. The bands are separated and ethidium bromide extracted three times with isoamyl alcohol. The DNA is extensively dialysed against 1000 volumes of 10 mM Tris-HCl pH 7.5 and 0.5 mM EDTA at 4° C. for two days.

24.2. Restriction digest: 10 to 15 µg of human placenta DNA (Example 24.1) are restricted to completion according to the protocols of the manufacturer with either restriction endonuclease BamHI, HindIII, EcoRI or PstI (Boehringer) for 2 h at 37° C. The restriction digests are loaded in separate slots (10 µg per slot) on a 0.6% agarose gel in 50 mM Tris-acetate pH 8.0 and 1 mM EDTA and run at 4° C. at 100 V during 6 h in this buffer. After electrophoresis the gel is stained with ethidium bromide (5 µg/ml $H_2O$) for 10 min and photographed with the help of an UV 260 nm transilluminator.

24.3. Southern blot: The stained gel of Example 24.2 is exposed to UV irradiation at 260 nm for 5 min to allow efficient transfer of high molecular weight DNA molecules. The gel is then incubated for 30 min in 0.4N NaOH and 0.6M NaCl for denaturation and for 30 min in 0.5M Tris-HCl pH 7.5 and 1.5M NaCl for neutralization. The gel is placed on a glass plate previously packed in 3 MM Whatman paper and immersed in a 20× SSC buffer (3M NaCl and 0.3M sodium citrate). A "GeneScreen plus"® membrane (New England Nuclear) prewetted with 2× SSC and a 5 cm pile of 3 MM Whatman paper are layered on the gel to allow the fluid transfer of nucleic acids in 20× SSC during 18 h at room temperature.

24.4. Hybridization with a MRP-8 cDNA probe: The BamHI, EcoRI, HindIII and PstI restriction digests of total human placenta DNA (Example 24.2) are examined for fragments containing sequences homologous and partially related to the human MRP-8 cDNA (clone 3 of Example 8.3). The placenta DNA fragments on "GeneScreen plus"® are hybridized at low and high stringency with a $^{32}P$ labelled probe of MRP-8 cDNA ($1.2\times10^7$ cpm/µg). This probe is prepared form the plasmid of clone 3 (Example 8.3) by digestion with PvuII/PstI, which cleaves a fragment of 369 bp, and nick translation as described in Example 8.5. The membrane with the DNA fragments is hybridized at 65° C. in 6× SSC buffer, 5× Denhart's solution, 0.1% SDS and 100 µg/ml calf thymus sonificated carrier DNA for 12 h with $5-10\times10^6$ cpm/ml of the MRP-8 cDNA probe. The membrane is washed at 65° C. in 6× SSC, 4× SSC, 2× SSC, 1× SSC and 0.1× SSC buffer containing 0.1% SDS successively, dried and exposed for autoradiography. Low stringency hybridization is performed likewise except for washing at 65° C. in 6× SSC containing 0.1% SDS only.

Only strongly hybridizing DNA fragments are observed at high and low stringency. The BamHI digest yields a hybridizing 18 kb fragment, HindIII a 22 kb, EcoRI a 21 kb, and PstI a 5 kb fragment. This result strongly suggests that the MRP-8 gene is present as a single copy in the human genome. To check whether the genomic DNA is indeed digested to completion, a control southern blot is hybridized with a human tissue plasminogen activator cDNA probe (S. Friezner-Degen, B. Rajput and E. Reich, J. Biol. Chem. 1986, 261, 6972). The published band pattern with BamHI, EcoRI, HindIII and PstI fragments is confirmed.

24.5. Isolation of genomic clones containing the MRP-8 gene: A human λ charon 4A genomic library is constructed from human fetal liver DNA by limited digestion with restriction endonucleases HaeIII and AluI (R. M. Lawn, E. F. Fritsch, R. C. Parker, G. Blake and T. Maniatis, Cell 1978, 15, 1157–1174). This library is screened with the MRP-8 cDNA probe as described in Example 24.4. 600'000 independent phage lambda plaques are transferred to nylon membranes (Pall-Biodyne™) and hybridized in duplicate with $8\times10^6$ cpm $^{32}DNA$ probe per membrane according to standard protocols (Maniatis handbook). The master plates are kept at 4° C. for several months. Six positive plaques are picked up, purified and the lambda DNA isolated for further analysis. Southern blot analysis of the DNA showed that all six recombinant phages contain the complete gene on the phage human DNA insert. A HpaII 5 kb long DNA fragment containing the complete MRP-8 coding region is subcloned from phage λ clone 3 into a wild type pBR322 vector linearized with ClaI giving rise to the plasmid pBRMRP-8/3A-HpaII.

EXAMPLE 25

Sequence analysis of plasmid pBRMRP-8/3A-HpaII

Figure 4:
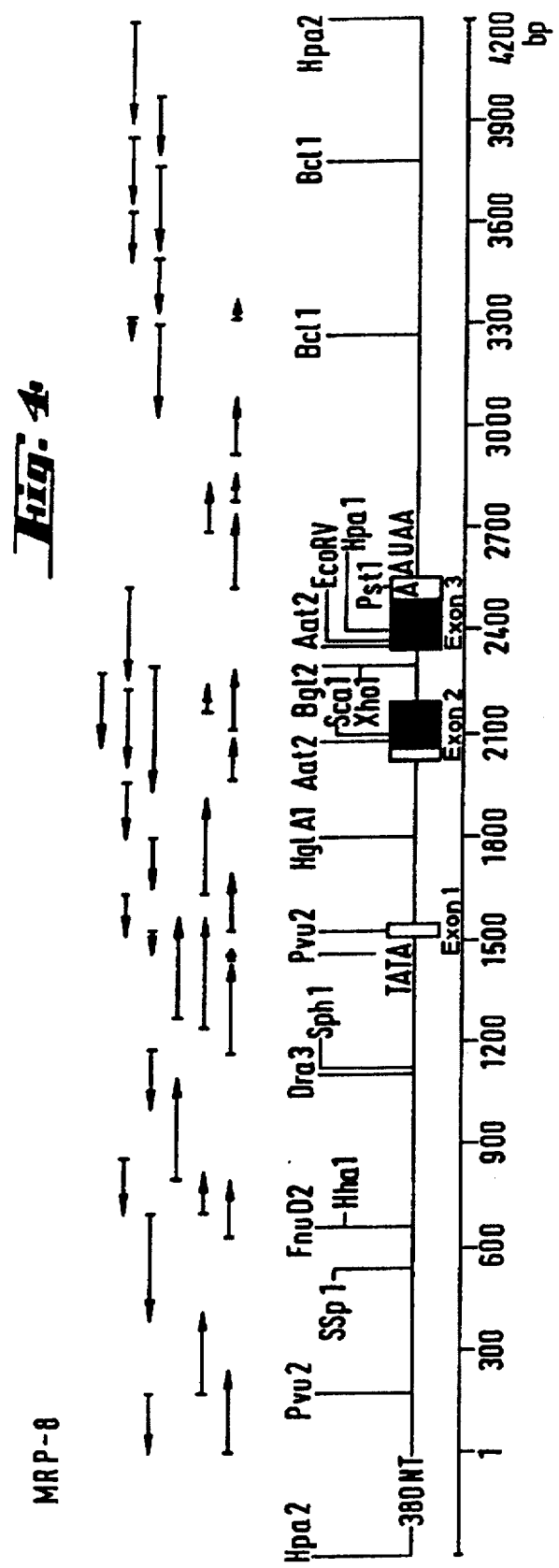
FIG. 4 gives a schematic representation of the genomic DNA of formula VIII (MRP-8). The lower lane shows the positions of restriction sites used for sequencing, the positions of exon 1, 2 and 3 (bars) and the coding sequence between the triplets ATG and TAG (black bars). The upper lane summarizes the sequence strategy showing start of sequence at restriction sites and end of readable sequence or end of sequence at restriction sites. The method of sequencing was according to Sanger and Coulson.

The sequencing strategy is depicted in FIG. 4 and the sequenced areas shown by lines and black circles pointing into the DNA sequencing direction. The DNA sequencing is performed on bacteriophage M13 single stranded templates according to the manufacturers protocol (Amersham). The complete DNA sequence of the MRP-8 gene is read on both strands.

The MRP-8 gene contains two introns (intron 1 and 2) and three exons (exon 1–3). Intron 1 interrupts the 5' untranslated region 23 nucleotides upstream from the ATG initiation codon while intron 2, which is 150 bp in length, interrupts the coding region at amino acid position 47. The non-coding exon 1 is 33 bp long. Exon 2 is 164 bp long and codes for the MRP-8 protein from amino acids 1 to 47 while exon 3 is 211 bp long and codes from amino acid 48 to 93 (C-terminus). The 56 bp long mRNA leader sequence is interrupted at 33 bp downstream the CAP site by the 484 bp long intron 1. The mRNA trailer up to the poly(A) addition site is 70 nucleotides long. The poly(A) addition site is deduced from the 3' end DNA sequence of the full length MRP-8 cDNA (Example 10). Thus the length of the MRP-8 mRNA is 408 nucleotides.

The complete DNA sequence of the gene coding for MRP-8 as well as the flanking DNA regulatory regions are shown in formula VIII. Regulatory DNA sequences as well as intron-exon junctions are overlined in formula VIII. At the 5' end of the gene a 5'-TATAAAA-3' promoter element is found 29 bp upstream the major MRP-8 mRNA CAP site. At the 3' end a poly(A) addition signal 5'-AATAAA-3' is found 53 bp downstream the amber codon. Beside the conserved splicing sites which are in agreement with the established GT/AG rule (R. Breathnach et al., Proc. Nat. Acad. Sci. USA 1978, 75, 4853–4857), the introns contain a polypyrimidine stretch and a consensus DNA sequence for the lariat structure formation.

EXAMPLE 26

Human genomic DNA coding for MRP-14

26.1. Hybridization of human placenta genomic DNA with a MRP-14 cDNA probe: The BamHI, EcoRI, HindIII and PstI restriction digests of total human placenta DNA of Example 24.2 are examined for fragments containing sequences homologous and partially related to the human MRP-14 cDNA (clone pMRP-14-10 of Example 9.3). The placenta DNA fragments on "GeneScreen plus"® are hybridized at low and high stringency with a $^{32}$P labelled probe of MRP-14 cDNA ($1.2\times10^7$ cpm/μg). This probe is prepared from the plasmid of clone pMRP-14-10 (Example 9.3) by digestion with DraIII/AvaI, which cleaves a fragment of 364 bp, and nick translation as described in Example 9.3. The membrane with the DNA fragments is hybridized at 5° C. in 6× SSC buffer, 5× Denhart's solution, 0.1% SDS and 100 μg/ml calf thymus sonificated carrier DNA for 12 h with $5-10\times10^6$ cpm/ml of the MRP-14 cDNA probe. The membrane is washed at 65° C. in 6× SSC, 4× SSC, 2× SSC, 1× SSC and 0.2× SSC buffer containing 0.1% SDS successively, dried and exposed for autoradiography. Low stringency hybridization is performed likewise except for washing at 65° C. in 4× SSC containing 0.1% SDS only.

Only strongly hybridizing DNA fragments are observed at high and low stringency. The BamHI digest yields a hybridizing 11.6 kb fragment, and PstI a 6 kb fragment. The HindIII and EcoRI digests both yield two fragments, i.e. for HindIII 5.7 and 3.6 kb, for EcoRI 5.4 and 2.7 kb. This result strongly suggests that the MRP-14 gene is present as a single copy in the human genome.

26.2. Isolation of genomic clones containing the MRP-14 gene: A human λ charon 4A genomic library is constructed from human fetal liver DNA and screened with the MRP-14 cDNA probe as described in Example 24.5. 600'000 independent phage lambda plaques are transferred to 20 nylon membranes and hybridized according to standard protocols. Four positive plaques are picked up, purified and the lambda DNA isolated for further analysis. Southern blot analysis of the DNA showed that all four recombinant phages contain the complete gene on the phage human DNA insert. A PstI 6 kb long DNA fragment containing the complete MRP-14 coding region is sub-cloned from phage λ clone 2 into a wild type pUC9 vector linearized with PstI giving rise to the plasmid pUCMRP-14/Pst6.

EXAMPLE 27

Sequence analysis of plasmid pUCMRP-14/Pst6

Figure 5:
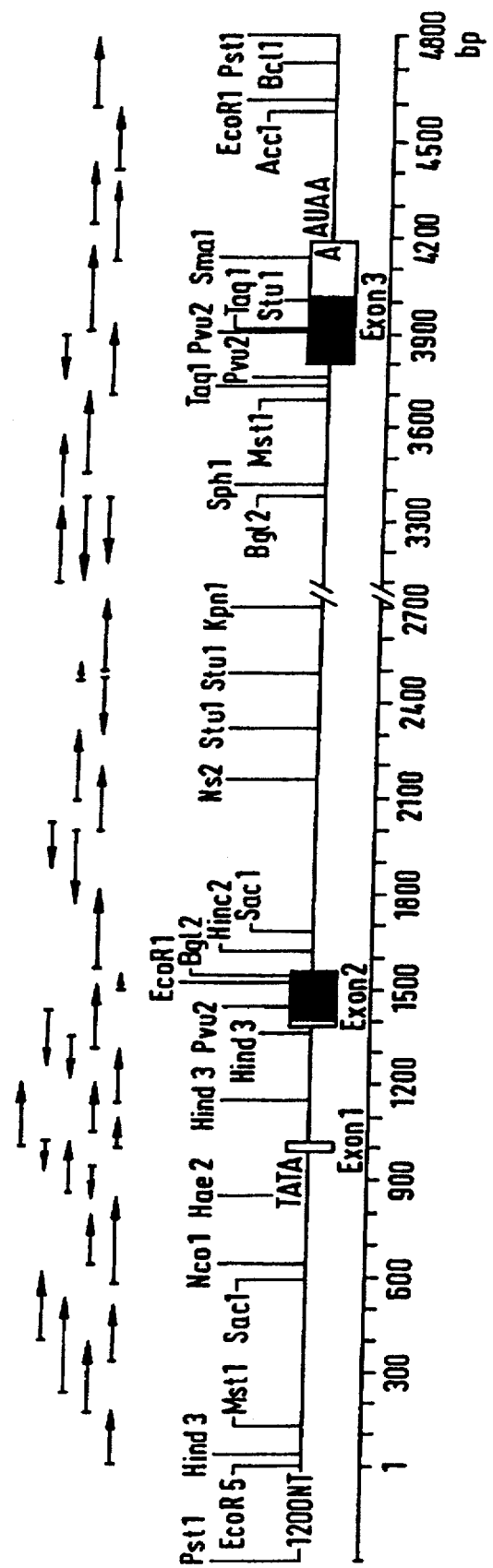
FIG. 5 gives a schematic representation of the genomic DNA of formula X (MRP-14). The positions of restriction sites, of exons 1, 2 and 3 (bars) and of the coding sequence between the triplets ATG and TAA (black bars) are shown. The sequence strategy can be deduced from the arrows: The sequence was read from a restriction site (beginning of the arrow) to the next restriction site or end of readable sequence. The sequencing method of Sanger and Coulson was used.

The sequencing strategy is depicted in FIG. 5 and the sequenced areas shown by lines and black circles pointing into the DNA sequencing direction. The DNA sequencing is performed with the dideoxy chain termination method on bacteriophage M13 single stranded templates and on double stranded supercoiled DNA templates according to the Maniatis handbook. The coding region of the MRP-14 gene is interrupted by two introns, intron 1 and intron 2. Intron 1 is 387 bp long and interrupts the 5' untranslated region 15 bp upstream from the ATG initiation codon. Intron 2 is about 2227 bp long and interrupts the coding region at amino acid position 50. The non-coding exon 1 is 28 bp long. Exon 2 is 165 bp long and codes for the MRP-14 protein from amino acid 1 to 50 while exon 3 is 389 bp long and codes for amino acid 51 to 114 (COOH terminus).

The DNA sequence of the gene coding for MRP-14 as well as the flanking DNA regulatory regions are shown in formula X. Between positions 1737 and 2098, the sequence is not known. Regulatory DNA sequences as well as intron-exon junctions are overlined in formula X. At the 5' end of the gene a 5'-TATAAAT-3' promoter element is found 29 bp upstream from the MRP-14 mRNA CAP site. At the 3' end a poly(A) addition signal 5'-AAATAAA-3' is found 164 bp downstream the ochre codon. Beside the conserved splicing sites which are in agreement with the established GT/AG rule (R. Breathnach et al., Proc. Nat. Acad. Sci. USA 1978, 75, 4853–4857), the introns contain a polypyrimidine stretch and a consensus DNA sequence for the lariat structure formation.

EXAMPLE 28

Construction of a vector for MRP-8 expression in mammalian cells

Figure 6:
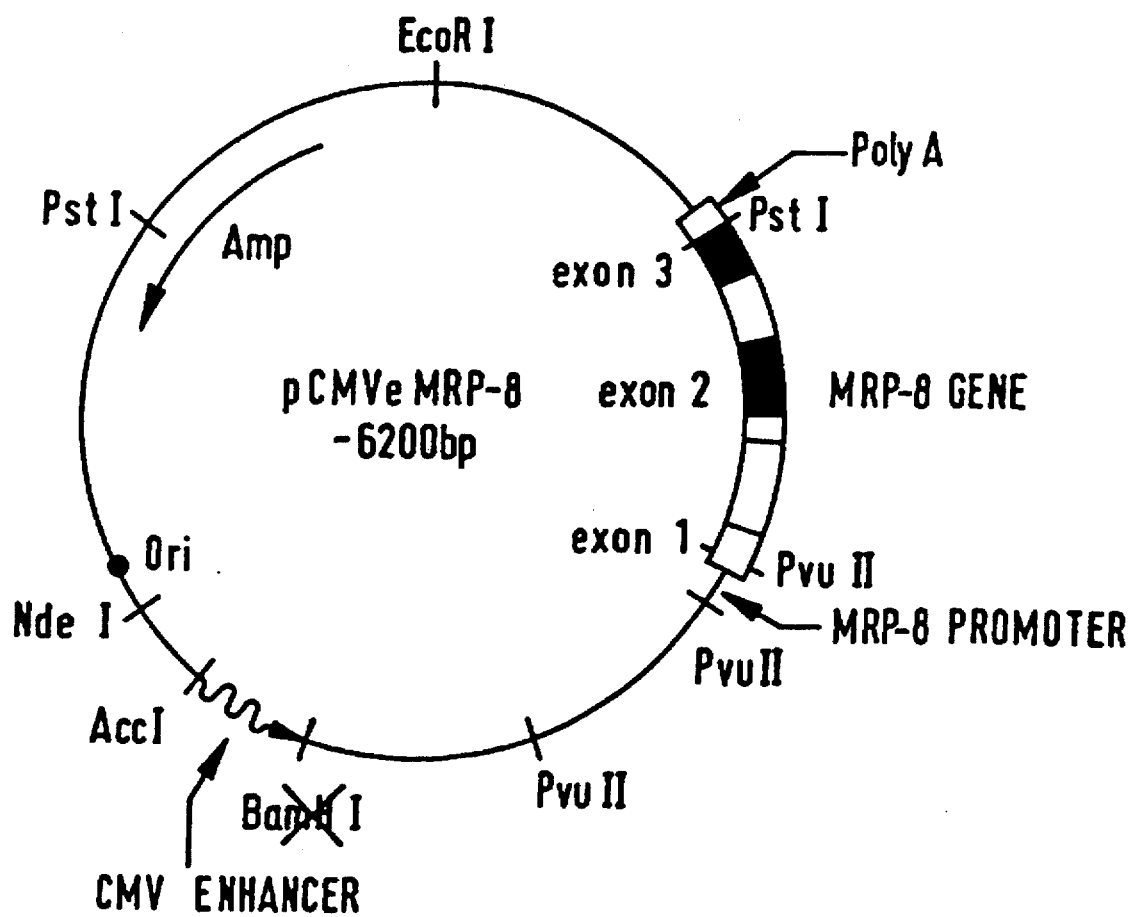
FIG. 6 displays a restriction map of plasmid pCMVe/MRP-8 with the relative positions of the origin Ori, the ampicillin resistance gene Amp$^R$, the human CMV enhancer and the three exons of the gene coding for MRP-8.

An expression vector pCMVe/MRP-8 is constructed by standard DNA manipulation and is shown in FIG. 6. The plasmid has the pBR322 origin of replication and the ampicillin resistance gene for propagation in E. coli. It contains the BamHI/EcoRI 4320 bp long DNA fragment derived from plasmid pBRMRP-8/3A-HpaII of Example 24.5, which carries the MRP-8 coding region, the 5' as well as the 3' DNA regulatory elements, further an eukaryotic transcription regulatory sequence in the form of a very strong constitutive enhancer on a 300 bp long DNA fragment located between the AccI site (position 2246 in pBR322) and the BamHI site from the BamHI/EcoRI 4320 bp long DNA fragment. This human cytomegalovirus (HCMV) enhancer from the major IE1 gone promoter region (M. Boshart, F. Weber, G. Jahn, K. Dorsch-Häsler, B. Fleckenstein and W. Schaffner, Cell 1985, 41, 521–530) is derived from plasmid pBR322AccI by standard DNA manipulation (Maniatis handbook). Plasmid pBR322AccI is made by ligating the 2144 bp long AccI/HindIII DNA fragment from pBR322 (J. G. Sutcliffe, Proc. Nat. Acad. Sci. USA 1978, 75, 3737–3741) using XbaI linkers (Biolabs Inc.) with the 300 bp long HCMV enhancer containing DNA fragment isolated by cutting the pSV40-HCMV (recombinant C4) with NcoI. The 300 bp NcoI enhancer DNA fragment covers the region upstream the initiation site between nucleotide −262 and −524 in the HCMV major IE1 gene promoter.

EXAMPLE 29

Construction of a vector for MRP-14 expression in mammalian cells

Figure 7:
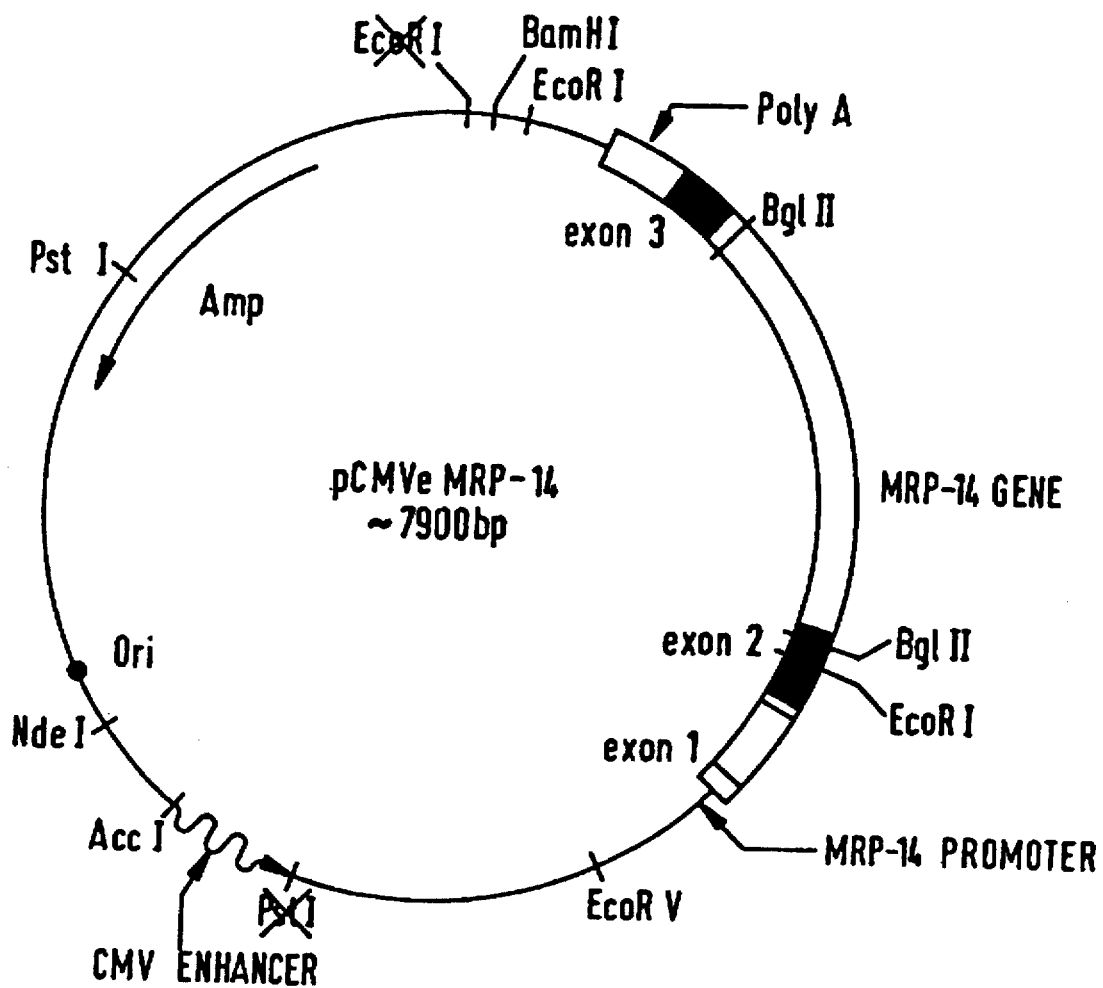
FIG. 7 displays a restriction map of plasmid pCMVe/MRP-14 with the relative position of the origin Ori, the ampicillin resistance gene Amp$^R$, the human CMV enhancer, the MRP-14 promoter region and the three exons coding for MRP-14.
Figure 8:
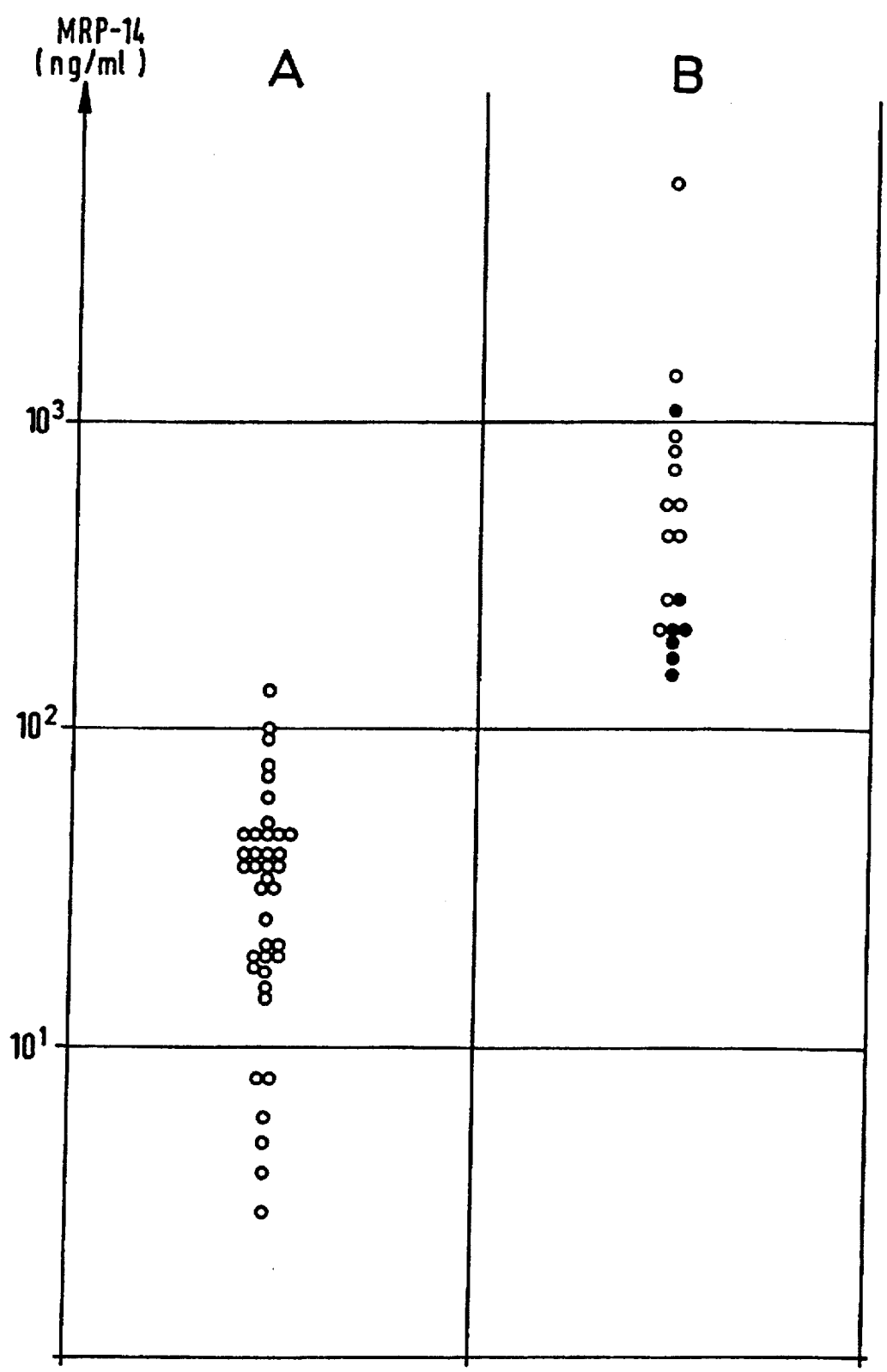
FIG. 8 shows the plasma concentration of 39 normal healthy donors (A) and a total of 18 cystic fibrosis (CF) patients whereby open circles denote homozygotes and filled dots denote heterozygotes (B). The representation is on a logarithmic scale in ng/ml MRP-14. The plasma samples taken with heparin are made up to 1 mM phenylmethane-sulfonyl fluoride and tested in duplicate by the sandwich ELISA of Example 42 using the polyclonal antibody to MRP-14 of Example 35.

An expression vector pCMVe/MRP-14 is constructed by standard DNA manipulation and is shown in FIG. 7. The plasmid is identical to the plasmid pCMVe/MRP-8 of Example 28 except that it contains the PstI 6000 bp long DNA fragment derived from plasmid pUCMRP-14/Pst6 of Example 26.2, which carries the MRP-14 coding region, the 5' as well as the 3' DNA regulatory elements.

EXAMPLE 30

Gene transfer and transient expression of the plasmids pCMVe/MRP-8 and pCMVe/MRP-14 in mammalian cells The MRP-8 gene and the MRP-14 gene are transfected into mammalian cells with a modified DEAE-dextran technique (J. H. Cutchan and J. Pagano, J. Natl. Cancer Inst. 1968, 41, 351–357; J. Banerji, L. Olson and W. Schaffner, Cell 1983, 33, 729–740).

30.1. Expression of pCMVe/MRP-8: Plasmid DNA of Example 28 is purified two times successively on CsCl/ ethidium bromide density gradients and resuspended in 10 mM Tris-HCl and 1 mM EDTA pH 7.5, then mixed with DEAE-dextran (0.5 mg/ml, Pharmacia, molecular weight $5 \times 10^6$) in DMEM (Gibco) containing 10 mM Hepes (Gibco) to a final concentration of 1 µg/ml plasmid DNA. The solution is incubated at room temperature for 10 min. A mock control containing the plasmid without gene is treated identically.

COS-7 cells (ATCC CRL 1651, SV-40 virus transformed kidney cells of African green monkey, Y. Gluzman, Cell 1981, 23, 175–182), Bowes cells (RPMI 7272, human malignant melanoma, D. C. Rijken and D. Collen, J. Biol. Chem. 1981, 256, 7035–7041) and L-132 cells (ATCC CCL 5, human embryonic lung fibroblasts, C. Davis et al., Fed. Proc. 1960, 19, 386) are plated in MEM containing 5%–10% FCS (Gibco) in 96 well microtiter plates or 10 cm Petri dishes (Falcon). The cell density reaches 60%–80% confluency after 24 h. The cell monolayer is rinsed twice with DMEM. The plasmid DNA DEAE-dextran mixture is added (50 µl per microtiter plate well and 1.2 ml per 10 cm Petri dish). The cells are incubated for 30 min at 37° C./5% $CO_2$, then for 90 min to 120 min at 37° C./7.5% $CO_2$ depending on the cell type. The cells are further incubated with 15% (v/v) DMSO (Merck) in DMEM for 90 sec, rinsed twice with DMEM, then incubated in 100 µl (per microtiter plate well) or 10.0 ml (per Petri dish) MEM containing 5.0% (v/v) FCS and 5 mM sodium butyrate (Sigma) for 12 h at 37° C./5% $CO_2$. The medium is changed to MEM containing 5% (v/v) FCS. The transfected cells are checked for expression of MRP-8 after 48 to 72 h.

30.2. Expression of pCMVe/MRP-14: Plasmid DNA of Example 29 is purified, mixed with DEAE-dextran and added to L-132 cells as above (Example 30.1). The L-132 cells are incubated for 30 min at 37° C./7.5% $CO_2$, and further processed as above. The transfected cells are checked for expression of MRP-14 after 48 to 72 h.

EXAMPLE 31

Characterization of MRP-8 expressed in mammalian cells 31.1. RNA isolation from L-132 cells transfected with pCMVe/MRP-8: A pellet containing $7 \times 10^6$ L-132 cells is resuspended in 500 µl GuSCN buffer 48 h after transfection (Example 30.1). They are homogenized by passing the GuSCN solution several times through a sterile disposable 1 ml pipette tip. The lysed cells are treated with phenol, and the nucleic acids precipitated according to a standard procedure (Maniatis handbook). The nucleic acids are centrifuged, redissolved in 7.5 ml of 10 mM Tris-HCl pH 7.0 and 1 mM EDTA and added to 7.5 g of CsCl (Merck). The CsCl solution is loaded on a 2 ml 5.7M CsCl cushion in a TST41 (15 ml) ultracentrifuge polyallomer tube. The RNA molecules are pelletted after 16 h at 2900 rpm at 20° C. in a Kontron TST41 rotor. The DNA remaining on top of the CsCl cushion is removed. The RNA pellet is redissolved in 2 ml elution buffer, precipitated with ethanol, resuspended in 100 µl 0.1% SDS and used for the primer extension experiment. The concentration is determined spectrophotometrically and amounts to 30–50 µg RNA per $10^6$ cells.

31.2. Preparation of a radioactive primer: A radioactive primer is prepared by annealing at 60° C. 500 ng of a synthetic DNA oligomer 5'-GGCTCGACCTCTTTCGGAAC-3' complementary to position 131 to 150 of MRP-8 cDNA of formula VII to 1 µg of a M13 single stranded template containing the complete MRP-8 cDNA sequence (Example 10) for 60 min. The oligomer is elongated by incubating in 50 µl of a solution containing 5 units of Klenow DNA polymerase (Boehringer) and 60 µCi of the four radiolabelled $\alpha$-$^{32}$P-dNTP at room temperature for 30 min. The reaction is chased with 5 µl chase mix (0.2 mM dNTP) for 15 min and stopped at 65° C. during 5 min. The newly synthesized DNA is restricted with PvuII and the reaction mixture separated by denaturing 8M urea 8% PAGE. The elongation product, a 68 nucleotides long DNA fragment, is cut out and eluted from the polyacrylamide gel. The specific activity of the synthesized primer is $0.5 \times 10^7$ cpm/µg.

31.3. Mapping of the 5' end of MRP-8 mRNA: 10 µg of total RNA from transfected human L-132 cells (Example 31.1) are coprecipitated with $1 \times 10^6$ cpm of the synthetic primer of Example 31.2 with ethanol. The nucleic acids are resuspended in 27 µl sterile $H_2O$ and 3 µl 2.5M KCl by shaking for 30 min. RNA and primer are denatured at 99° C. for 3 min and annealed at 60° C. for 1 h. 30 µl of triply concentrated reverse transcriptase buffer (60 mM Tris-HCl pH 8.8, 30 mM $MgCl_2$, 30 mM DTT) are added and the reaction mixture adjusted to 3 mM dNTP mix in 90 µl. 10 units of reverse transcriptase (BRL) are added and the reaction mixture incubated for 30 min at 37° C., then stopped with 4 µl 0.5M EDTA pH 7.5. The RNA is hydrolysed by alkali treatment with 50 mM NaOH for 1 h at 65° C. The nucleic acids are neutralized, then precipitated with ethanol in the presence of carrier tRNA. The nucleic acids are resuspended in formamide sample buffer (80% formamide, 10 mM NaOH, 1 mM EDTA, 0.1% xylene cyanol, 0.1% bromophenol blue) and the extended primer visualized on a DNA sequencing 8M urea 8% PAGE in TBE buffer. 90% of the elongated RNA molecules comigrate with a deoxyadenosine located 30 bp downstream the 5'-TATAAAA-3' regulatory element. The same result are obtained when poly(A) RNA isolated from human blood mononuclear cells are assayed with the same primer as described above. No such elongated product is detected out of the mock-transfected cell RNA molecules when the latter are assayed under identical conditions as for the pCMVe/ MRP-8 transfected cells.

31.4. Immunohistological detection of MRP-8 in situ: Cells transfected with pCMVe/MRP-8 of Example 30.1 are fixed with glutaraldehyde using established protocols.(J. Br üggen et al., Cancer Immunol. Immunother. 1983, 15, 200–205): The cell monolayer is rinsed twice with PBS and incubated with 0.05% (v/v) glutaraldehyde (Fluka) in PBS for 5 min at room temperature followed by rinsing twice with PBS.

The fixed cells are tested for the expression of MRP-8 using a modified version of an immunoperoxidase technique (J. Brüggen et al., 1983, loc. cit.; Suter et al., Cancer Immunol. Immunother. 1983, 16, 53–58) in the following way: After blocking of nonspecific binding with 10% (v/v) normal swine serum (Gibco), the cells are incubated with a monospecific rabbit anti-MRP-8 serum (Example 34.1) for 30 min at 37° C. The specific antibodies bound to the cells are incubated with swine anti-rabbit IgG conjugated to horseradish peroxidase (DAKO) for 30 min at 37° C. The peroxidase bound is reacted with 0.10% (v/v) $H_2O_2$ (Merck) and 0.26% (w/v) 3-amino-9-ethylcarbazole (AEC, Sigma) in 0.1M acetate buffer pH 5.2 for 7 min at room temperature. The evaluation is done on 500 cells microscopically; MRP-8 positive cells display a red coloured precipitate. Table 1 shows the percent expression in the tested cells. MRP-8 is expressed to a high percentage in human embryonic lung cells L-132. Expression is much lower in SV-40 transformed monkey kidney cells COS-7 and in human malignant melanoma cells (Bowes). Mock-treated controls and negative control sera are negative.

TABLE 1

Expression of MRP-8 transfected mammalian cells

| Cell line | species | origin of tissue | cells scored positive |
|---|---|---|---|
| COS-7 | monkey | kidney | 1% |
| Bowes | man | malignant melanoma | <1% |
| L-132 | man | embryonic lung | 65% |

31.5. Western blot of MRP-8 expressed in mammalian cells: Embryonic lung cells L-132 transfected with the MRP-8 gene as described in Example 30.1 are detached with 0.05% (w/v) trypsin and 0.02% (w/v) EDTA (Gibco), pelleted at 80×g and lysed with 0.5% (v/v) NP-40 or 0.1% (w/v) SDS in buffer containing 20 mM Tris-HCl, 120 mM NaCl, 5 mM KCl, 1.4 mM Mg(OAc)$_2$, 3.6 mM CaCl$_2$, 6.0 mM β-mercaptoethanol and 1 mM PMSF (all reagents from Biorad) on ice for 15 min. The cellular lysate is centrifuged at 48'000×g for 60 min and the supernatant processed by a SDS-PAGE (15% (w/v); U. K. Lämmli, Nature 1970, 227, 680–685). The amount of protein introduced per slot corresponds to a cellular equivalent of 5×10$^5$ cells. The separated protein is electrotransferred onto nitrocellulose (Millipore; Towbin et al., Proc. Nat. Acad. Sci. USA 1979, 76, 4350). The proteins transferred onto the nitrocellulose sheet are stained with 0.1% (w/v) amidoblack (Merck) in 45% (v/v) methanol and 10% (v/v) acetic acid. An untreated sheet of nitrocellulose is developed with rabbit anti-MRP-8 serum (Example 34.1) for 14 h at 4° C. followed by swine anti rabbit IgG conjugated to horseradish peroxidase (DAKO). The bound peroxidase is made visible by 0.1% $H_2O_2$ and 0.3% (w/v) chloronaphthol (Merck) diluted in PBS for 7 min. The rabbit anti-MRP-8 serum recognizes a protein band within the cell lysates which displays a molecular weight of 8 kg/mol and shows the same characteristics as the recombinant MRP-8 protein expressed in E. coli or yeast (Example 21).

EXAMPLE 32

Characterization of MRP-14 expressed in mammalian cells 32.1.Immunohistological detection of MRP-14 in situ in L-132 cells transfected with pCMVe/MRP-14: Transfected L-132 cells of Example 30.2 are fixed with glutaraldehyde and tested for the expression of MRP-14 using the method of Example 31.4. The cells are incubated with the monospecific rabbit anti-MRP-14 serum of Example 35.1. The evaluation is done on 500 cells microscopically; MRP-14 positive cells display a red coloured precipitate. MRP-14 is expressed in 75% of the transfected human embryonic lung cells L-132. Mock-treated controls and negative control sera are negative.

32.2. Western blot of MRP-14 expressed in L-132 cells: Embryonic lung cells L-132 transfected with pCMVe/MRP-14 as described in Example 30.2 are lysed and the lysate processed by a SDS-PAGE as described in Example 31.5. The separated proteins are electrotransferred onto nitrocellulose and developed with rabbit anti-MRP-14 serum (Example 35.1) for 14 h at 4° C. followed by swine anti-rabbit IgG conjugated to horseradish peroxidase (DAKO). The rabbit anti-MRP-14 serum recognizes a protein band within the cell lysates which displays a molecular weight of 14 kg/mol and shows the same characteristics as the recombinant MRP-14 protein expressed in E. coli or yeast (Example 22).

EXAMPLE 33

Isolation of stable human cell lines expressing MRP-8 MRP-14

In order to achieve the isolation of permanent human cell lines producing recombinant MRP-8 or MRP-14, a plasmid containing the dominant selection marker Tn 5 neomycin conferring resistance to G-418 is coprecipitated with the plasmid containing the MRP-8 gene or the plasmid containing the MRP-14 gene on human embryonic lung cells L-132 using the calcium phosphate technique (F. L. Graham and A. J. van der Eb, Virology 1973, 52, 456–467; D. Picard and W. Schaffner, Proc. Natl. Acad. Sci. USA 1983, 80, 417–421).

The plasmids pSV$_2$ neo (P. Southern and P. Berg, J. Mol. Appl. Genet. 1982, 1, 327–341) and pCMVe/MRP-8 (Example 28) or pCMVe/MRP-14 (Example 29) are mixed in a ratio of 1:5 in 10 mM Tris-HCl/1 mM EDTA, pH 7.5. An equal volume of 0.5M CaCl$_2$ containing 0.1M Hepes (Gibco), pH 7.05, is added and the mixture incubated for 5 min at 22° C. Twice the volume of 2× HBS (0.05M Hepes, 0.28M NaCl, 0.75 mM Na$_2$HPO$_4$ and 0.75 mM NaH$_2$PO$_4$) is added to give a final concentration of 4 μg/ml pSV$_2$ neo and 20 μg/ml pCMVe/MRP-8 or pCMVe/MRP-14, and the mixture left on ice for 30 min. 10 μl amounts of this mixture are added to subconfluent L-132 cells (Example 30) grown in 100 μl in 96 well microtiter plates. The cells are incubated for 16 h at 37° C./5% CO$_2$, treated with 15% (v/v) DMSO for 90 sec, refed with MEM containing 5% (v/v) FCS and 5 mM sodium butyrate, incubated for 6 h at 37° C./5% CO$_2$, refed with MEM and incubated for 24 h at 37° C./5% CO$_2$. The selection agent G-418 (Gibco) is added to a final concentration of 1 mg/ml. The cells are cultured for 5 days, trypsinized, split in MEM/5% FCS at a ratio of 1:5 into 96 well microtiter plates and incubated at 37° C./5% CO$_2$ with G-418. After 10 days single cell clones are isolated and propagated to mass cell cultures according to standard procedures. The cells are examined for the expression of MRP-8 or MRP-14 as described in Examples 31 and 32, and positive clones selected.

EXAMPLE 34

Polyclonal antibodies to MRP-8

34.1. Rabbit anti-MRP-8 serum: The rabbit anti-MRP-8 serum is generated by immunization of a rabbit with recombinant MRP-8 from *E. coli* (Example 12) purified by size exclusion chromatography (Example 20.2). 0.5 mg protein in complete Freund's adjuvans (Gibco) are injected followed by a booster injection of 0.5 mg protein in incomplete Freund's adjuvans after 20 days. The titer of the rabbit serum is monitored by an enzyme linked immunosorbent assay (ELISA) in microtiter plates coated with recombinant MRP-8 following established protocols. Examination of Western blots reveals that, after exhaustive absorption with lysates of untransfected *E. coli*, the only reactivity left in the anti-serum is directed against MRP-8.

34.2. Isolation of rabbit antibodies specific for MRP-8 by immunoaffinity chromatography: A MRP-8-Affi-Gel 10 immunoadsorbent column is prepared by coupling 4–5 mg of purified recombinant MRP-8 (Example 20) to 1 ml of Affi-Gel® 10 using the manufacturers procedure (Bio-Rad, Richmond, Calif.). Immunoglobulin G (IgG) from the monospecific rabbit anti-MRP-8 serum (Example 34.1) is precipitated by ammonium sulfate at 50% saturation. The precipitate is dissolved in PBS and dialysed against PBS. 15 ml of the dialysed solution containing approximately 100 mg of IgG is pumped through the immunoaffinity column at a flow rate of 10–12 ml/h. Unspecifically bound material is removed by washing the column with PBS/0.4M sodium chloride. Specifically bound IgG is eluted with 0.1M glycine hydrochloride, pH 2.5. Fractions containing the antibodies are pooled, neutralized by adding 1M Tris and dialysed against PBS. Approximately 4 mg of IgG specific for MRP-8 are obtained.

EXAMPLE 35

Polyclonal antibodies to MRP-14

35.1. Rabbit anti-MRP-14 serum: The rabbit anti-MRP-14 serum is generated by immunization of a rabbit with purified recombinant MRP-14 from *E. coli* (Example 22). 0.5 mg protein in complete Freund's adjuvans (Gibco) are injected followed by a booster injection of 0.5 mg protein in incomplete Freund's adjuvans after 20 days. The titer of the rabbit serum is monitored by an enzyme linked immunosorbent assay (ELISA) in microtiter plates coated with recombinant MRP-14 following established protocols. Examination of Western blots reveals that, after exhaustive absorption with lysates of untransfected *E. coli*, the only reactivity left in the anti-serum is directed against MRP-14.

35.2. Isolation of rabbit antibodies specific for MRP-14 by immunoaffinity chromatography: Analogously to the manner described in Example 34.2, a recombinant MRP-14-Affi-Gel 10 immunoadsorbent column is prepared and used for the isolation of rabbit anti-MRP-14 IgG from monospecific rabbit anti-MRP-14 serum. Approximately 3.2 mg of IgG specific for MRP-14 are obtained.

EXAMPLE 36

Hybridoma cells producing monoclonal antibodies against MRP-8

36.1. Immunization protocol: 3 female Balb/c mice are injected each intraperitoneally with 0.1 mg of recombinant MRP-8 (Example 12, purified as in Example 20.2) in complete Freund's adjuvans followed by two booster injections of 0.05 mg MRP-8 in incomplete Freund's adjuvans at 14 days interval. After 6 weeks 0.05 mg MRP-8 in physiological saline is injected and the mice sacrificed 4 days later.

36.2. Cell fusion and isolation of hybridomas: All fusion experiments are performed following established protocols (G. Köhler and C. Milstein, Nature 1976, 256, 495) using the nonsecreting myeloma line P3×63-Ag8.653 (ATCC No. CRL 1580). $10^8$ spleen cells are fused with $10^7$ myeloma cells in the presence of 35% polyethylene glycol (w/v) PEG 4000, Merck) and of 15% dimethylsulfoxide (Merck). The fusion mixture is distributed in standard HAT selection medium (20% FCS, Gibco) in 1200 wells of microtiter plates (Falcon) containing mouse peritoneal exudate cells as feeder cells. After 10–14 days the supernatants of growing hybridomas are tested for binding to MRP-8 with a sandwich-type ELISA (Example 40.2). Of 633 hybridomas supernatants tested 48 scored strongly positive in this assay. Suitable hybridoma are recloned by limiting dilution at least two times.

EXAMPLE 37

Isolation and characterization of monoclonal antibodies to MRP-8.

37.1. Isolation and purification: Balb/c mice 8–10 weeks of age are pretreated intraperitoneally (i.p.) with 0.3 ml pristane (Aldrich). 2–3 weeks later, $5-10\times10^6$ cloned hybridoma cells and 0.2 ml pristane are injected i.p. After 8–10 days ascites fluid is collected, centrifuged at 800×g and stored at −80° C.

Alternatively the hybridomas are propagated in vitro at a large scale using hybridoma medium (Gibco). The supernatant is centrifuged at 800×g, filtered with a 0.45 μm Nalgene® filter and stored at −80° C.

Crude immunoglobulin is precipitated by dropwise addition of 0.9 volume equivalents of saturated ammonium sulphate at 0° C., then dissolved in 20 mM Tris-HCl, 50 mM NaCl, pH 7.9. An IgG fraction is obtained by using the Affigel® Protein A MAPS Kit procedure of Bio-Rad. The eluted IgG fraction is precipitated again with ammonium sulphate and dissolved in PBS at a concentration of 10 mg/ml and dialysed against the same buffer.

37.2. Characterization: The antibodies produced by the selected hybridomas 8-5C2 and 8-10D7 are tested for their specificity in the sandwich type ELISA using rabbit anti-MRP-8 and anti-MRP-14 (Examples 40 and 42), in the Western blot for MRP-8 and MRP-14 (Examples 31.5 and 32.2) and in the single cell assay for MRP-8 and MRP-14 (Examples 31.4.and 32.1). The monoclonal antibodies 8-5C2 and 8-10D7 selectively recognize the MIF 8 kD of EP 162 812 and the recombinant MRP-8 as expressed in *E. coli* (Example 12), yeast (Example 19) and transfected embryonic lung cells L-132 (Example 30), but do not crossreact with either natural or recombinant MRP-14 or with other proteins. The recognized epitope is SDS-stable.

The subclass of the monoclonal antibodies is determined following standard protocols (J. Brüggen et al., Cancer Immunol. Immunother. 1983, 15, 200) and is found to be $IgG_1$ for both 8-5C2 and 8-10D7.

EXAMPLE 38

Hybridoma cells producing monoclonal antibodies against MRP-14

Balb/c mice are immunized with 0.1 mg recombinant MRP-14 from *E. coli* (Example 13, purified according to Example 22) in complete Freund's adjuvans followed by two booster injections of 0.05 mg MRP-14 in incomplete Freund's adjuvans at 14 days intervals. After 6 weeks 0.05 mg MRP-14 in physiological saline are injected. 4 days later the spleen cells of the immunized mice are collected and fused with mouse myeloma cells P3×63-Ag8.653 (ATCC No. CRL 1580), and the resulting hybridoma cells screened as described in Example 36. Of 420 hybridoma supernatants tested 27 were positive in the sandwich-type ELISA of Example 42. Suitable hybridomas are recloned by limiting dilution at least two times.

EXAMPLE 39

Isolation and characterization of monoclonal antibodies to MRP-14

Selected hybridoma cells of Example 38 are propagated in vivo or cultured in vitro as described in Example 37.1. The precipitated IgG fraction is purified using the Affigel® Protein A MAPS kit, precipitated again with ammonium sulfate, dissolved in PBS at a concentration of 10 mg/ml, dialysed against PBS and stored at −80° C.

The antibodies produced by the selected hybridomas 14-6B2 and 14-19C9 are tested for their specificity in the sandwich type ELISA, Western blot and single cell assay as described in Example 37.2. The monoclonal antibodies 14-6B2 and 14-19C9 selectively recognize natural MRP-14, MRP-14', recombinant MRP-14 and MRP-14d, but do not crossreact with MRP-8 or other proteins. The subclass of the monoclonal antibodies 14-6B2 and 14-19C9 is determined to be $IgG_1$.

EXAMPLE 40

Detection of MRP-8 with an enzyme-immunoassay (ELISA)

40.1. Biotinylation of polyclonal and monoclonal antibodies to MRP-8: 1 mg of polyclonal rabbit anti-MRP-8 antibody (Example 34) or monoclonal antibody 8-5C2 (Example 37) and 0.1 mg Biotin-X-NHS® (Calbiochem) are reacted in 1.0 ml 0.1M Hepes buffer, pH 8.0, for 4 h at 4° C. according to a modified version of the method of Lerner et al. (J. Exp. Med. 1980, 152, 1085). The biotinylated antibodies are dialysed at 4° C. against PBS and stored at −80° C.

40.2. Sandwich type ELISA using polyclonal rabbit anti-MRP-8 and biotinylated rabbit anti-MRP-8 antibodies: Microtiter plates (NUNC FI) are coated with the affinity purified rabbit anti-MRP-8 antibodies (5 µg/ml) of Example 34.2 in 0.05M carbonate buffer, pH 9.6 at 50 µl/well and incubated overnight at 4° C. The coated plates can be stored for 2 weeks. After blocking the nonspecific sites with PBS containing 0.2% gelatine and 1% BSA (Serva) for 1 h at 37° C., 50 µl/well of a dilution series of MRP-8 (Example 20.2, 0.1–50 ng/ml) and 50 µl/well of a dilution series of test samples in PBS containing 0.2% gelatine, 1% BSA and 0.05% Tween 20 (Bio-Rad) are added and incubated overnight at 4° C. After rinsing with PBS containing 0.05% Tween 20 the biotinylated rabbit anti-MRP-8 (1 µg/ml) of Example 40.1 in PBS, 0.2% gelatine and 0.05% Tween 20 is incubated for 1 h at 37° C. followed by streptavidin-peroxidase (BRL) for 30 min at 37° C. After rinsing with PBS and 0.05% Tween 20 the bound peroxidase is developed using 0.064% (v/v) $H_2O_2$ (Merck) and 2,2'-azino-bis-(3-ethylbenzthiazoline sulfonic acid) (ABTS, 0.54 mg/ml (w/v), Böhringer Mannheim) dissolved in 0.05M citrate buffer, pH 4.0. After 30 min at 37° C. the optical density is measured at 415 nm using an eight channel photometer (FLOW).

The assay detects MRP-8 down to 50 µg/ml in cellular lysates of human monocytes, in MRP-8 transfected embryonic lung cells L-132 (Example 31) and in plasma samples of human patients and normal subjects.

The biotinylated rabbit anti-MRP-8 can be replaced by the biotinylated mouse monoclonal antibody 8-5C2 (1 µg/ml).

40.3. Sandwich type ELISA using the monoclonal antibodies 8-10D7 and the biotinylated antibodies 8-5C2: The assay procedure is as in Example 40.2, except that the microtiter plates are coated first with the monoclonal antibody 8-10D7 (10 µg/ml). After blocking nonspecific sites the test samples and standard solutions of MRP-8 are added and then reacted with the biotinylated antibody 8-5C2 (1 µg/ml). The remaining procedure is as described.

The biotinylated monoclonal antibody 8-5C2 can be replaced by biotinylated rabbit anti-MRP-8.

40.4. Sandwich type ELISA using the monoclonal antibodies 8-10D7 or 8-5C2 and rabbit anti-MRP-8: The assay procedure is as described in Example 40.2. As capture antibody 8-10D7 (or 8-5C2) is coated (10 µg/ml) on the microtitre plate. After blocking the nonspecific site, the test samples and standard solutions containing MRP-8 are added and then reacted with the rabbit anti-MRP-8. The bound rabbit antibodies are detected with species specific goat anti-rabbit Ig peroxidase conjugate (DIANOVA) and further processed as in Example 40.2.

An equivalent assay uses polyclonal rabbit anti-MRP-8 for coating followed by the test samples and then the mouse monoclonal antibody 8-5C2 or 8-10D7. The mouse antibodies bound are reacted with species specific goat anti-mouse Ig peroxidase conjugate (DIANOVA).

EXAMPLE 41

Test kit for sandwich ELISA for MRP-8

A test kit for the sandwich ELISA of Example 40.2. contains

1) Microtiter plates (NUNC FI)
2) 10 ml affinity purified rabbit anti-MRP-8 polyclonal antibody (5 µg/ml, Example 34.2) in 0.05M carbonate buffer, pH 9.6.
3) 1.0 ml of recombinant MRP-8 standard solution (1 mg/ml) in PBS containing 0.05% Tween 20.
4a) 10 ml of biotinylated rabbit-anti-MRP-8 (1 µg/ml, Example 40.1) in PBS, pH 7.4, 0.2% gelatine, 1% BSA, 0.05% Tween 20 or
4b) 10 ml of biotinylated monoclonal antibody 8-5C2 (1 µg/ml) in PBS, pH 7.4, 0.2% gelatine, 1% BSA, 0.05% Tween 20.
5) 10 ml Streptavidin-peroxidase (BRL) 1:2000 in PBS, pH 7.4, 2% gelatine, 1% BSA, 0.05% Tween 20.
6) 200 ml PBS, 0.05% Tween 20.
7) 200 ml PBS, pH 7.4, 0.2% gelatine, 1% BSA, 0.05% Tween 20.
8) 40 ml of ABTS (0.54 mg/ml) and 0.064% $H_2O_2$ in 0.05M citrate buffer, pH 4.0.
9) calibration curve.
10) instruction manual.

A test kit for the sandwich type ELISA of Example 40.3. contains the same components as above except for the following replacements:

2) 10 ml monoclonal antibody 8-10D7 (10 µg/ml).
4a) 10 ml biotinylated monoclonal antibody 8-5C2 (1 µg/ml) or
4b) 10 ml biotinylated polyclonal rabbit anti-MRP-8 antibody (1 µg/ml).

A test kit for the sandwich type ELISA of Example 40.4. contains the same components as above except for the following replacements:

2a) 10 ml monoclonal antibody 8-10D7 or 8-5C2 (10 µg/ml) or 2b) 10 ml of affinity purified polyclonal rabbit anti-MRP-8 antibody (5 µg/ml).

4a) 10 ml polyclonal rabbit anti-MRP-8 antibody (1 µg/ml) and 5a) 10 ml goat anti-rabbit Ig peroxidase conjugate 1:5000 or 4b) 10 ml monoclonal antibody 8-5C2 (1 µg/ml) and 5b) 10 ml goat anti-mouse Ig peroxidase conjugate 1:5000.

EXAMPLE 42

Detection of MRP-14 with an enzyme-immunoassay (ELISA)

Polyclonal rabbit anti-MRP-14 antibody (Example 35) or monoclonal antibody 14-6B2 or 14-19C9 (Example 39) are biotinylated as described in Example 40.1.

A sandwich type ELISA is set up for detection of MRP-14 as described in Examples 40.2 or 40.4 substituting polyclonal antibody anti-MRP-14 for anti-MRP-8 and monoclonal antibody 14-6B2 or 14-19C9 for 8-10D7 or 8-5C2. Reference standard solutions are made from MRP-14 of Example 22 (0.1–100 ng/ml).

For the determination of MRP-14 in blood plasma, the plasma samples taken with heparin are made up to 1 mM phenylmethanesulfonyl fluoride (PMSF, Fluka) immediately and stored at −80° C. For analysis the samples are diluted from 1:5 to 1:10'000 and tested in the described sandwich assay.

EXAMPLE 43

Test kit for sandwich ELISA for MRP-14

A test kit for the sandwich ELISA of Example 42 using polyclonal anti-MRP-14 antibody and biotinylated anti-MRP-14 or biotinylated monoclonal antibody 14-6B2 contains 1) Microtiter plates (NUNC FI)
2) 10 ml affinity purified rabbit anti-MRP-14 polyclonal antibody (5 µg/ml, Example 35.2) in 0.05M carbonate buffer, pH 9.6.
3) 1.0 ml of recombinant MRP-14 standard solution (1 mg/ml) in PBS containing 0.05% Tween 20.
4a) 10 ml of biotinylated rabbit-anti-MRP-14 (1 µg/ml) in PBS, pH 7.4, 0.2% gelatine, 1% BSA, 0.05% Tween 20 or
4b) 10 ml of biotinylated monoclonal antibody 14-6B2 (1 µg/ml) in PBS, pH 7.4, 0.2% gelatine, 1% BSA, 0.05% Tween 20.
5) 10 ml Streptavidin-peroxidase (BRL) 1:2000 in PBS, pH 7.4, 2% gelatine, 1% BSA, 0.05% Tween 20.
6) 200 ml PBS, 0.05% Tween 20.
7) 200 ml PBS, pH 7.4, 0.2% gelatine, 1% BSA, 0.05% Tween, 20.
8) 40 ml of ABTS (0.54 mg/ml) and 0.064% $H_2O_2$ in 0.05M citrate buffer, pH 4.0
9) calibration curve.
10) instruction manual.

The biotinylated polyclonal or monoclonal antibody and the streptavidin-peroxidase conjugate (4 and 5) may be replaced by the polyclonal or monoclonal antibodies themselves and a species specific anti-Ig serum peroxidase conjugate as in Example 41.

EXAMPLE 44

Pharmaceutical preparation for parenteral application

200 µg of MRP-8 of Example 20.5 or MRP-14 of Example 22.3 are dissolved in 3 ml of 5N human serum albumin. The resulting solution is passed through a bacteriological filter and the filtered solution subdivided under aseptic conditions into 10 vials. The vials are preferably stored in the cold, for example at −20° C.

We claim:

1. A DNA comprising an isolated DNA encoding for a MRP-8 polypeptide having a sequence of formula I, wherein formula I is:

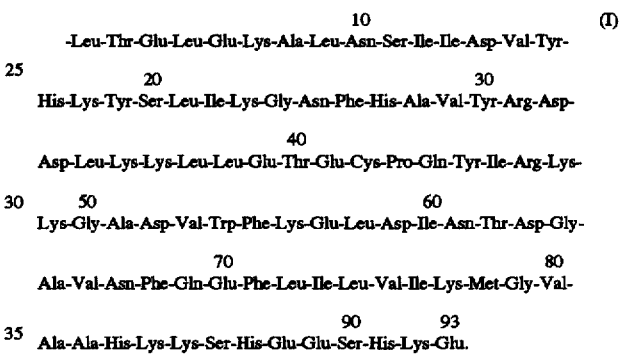

2. A DNA comprising an isolated DNA encoding for a MRP-14 polypeptide having a sequence of formula II, wherein formula II is:

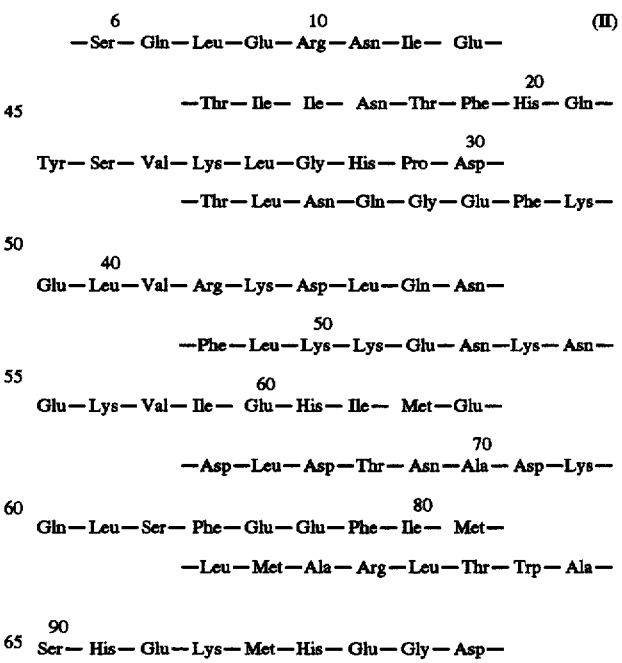

—Glu—Gly—Pro—Gly—His—His—His—Lys—
                    100

Pro—Gly—Leu—Gly—Glu—Gly—Thr—Pro.
    110                      114

3. A DNA according to claim 1 having formula VII, wherein formula VII is:

```
AACTTGCAACAGCCCTTCTACATACACTCCATCTTCTCTATCTTAGTTACAAGTTTTTTT
         10        20        30        40        50        60
AATAAGAAATGGGCAAAGTCAGCTGTCTTTCAGAAGACCTGGTGGGGCAAGTCCGTGGGC
         70        80        90       100       110       120
                                          10
         M   L   T   E   L   E   K   A   L   N   S   I   I   D   V   Y   H   K   Y
ATCATGTTGACCGAGCTGGAGAAAGCCTTGAACTCTATCATCGACGTCTACCACAAGTAC
        130       140       150       160       170       180
 20                                     30
  S   L   I   K   G   N   F   H   A   V   Y   R   D   D   L   K   K   L   L   E
TCCCTGATAAAGGGGAATTTCCATGCCGTCTACAGGGATGACCTGAAGAAATTGCTAGAG
        190       200       210       220       230       240
 40                                  50
  T   E   C   P   Q   Y   I   R   K   K   C   A   D   V   W   F   K   E   L   D
ACCGAGTCTCCTCAGTATATCAGGAAAAAGGGTGCAGACGTCTGGTTCAAAGAGTTGGAT
        250       260       270       280       290       300
 60                                    70
  I   N   T   D   G   A   V   N   F   Q   E   F   L   I   L   V   I   K   M   C
ATCAACACTGATGGTGCAGTTAACTTCCAGGAGTTCCTCATTCTGGTGATAAAGATGGCC
        310       320       330       340       350       360
 80                                     90
  V   A   A   H   K   K   S   H   E   E   S   H   K   E
GTGGCAGCCCACAAAAAAAGCCATGAAGAAAGCCACAAAGAGTAGCTGAGTTACTGGGCC
        370       380       390       400       410       420
CAGAGGCTGGGCCCCTGGACATGTACCTGCAGAATAATAAAGTCATCAATACCTCAAAAA
        430       440       450       460       470       480
AAAAA.                                                              (VII)
```

4. A DNA according to claim 1 having formula VIII, wherein formula VIII is:

(VIII)

```
                                                                                    CTTGGGTTGC   -1501
TTCCACCTTTTGGCTCTTGTAAATAATCCTGCTATGAACATGAATGTACAAACATCTGTTGAATCCCTGCAATTCAATTCTTTGCATATATACCCAGGA   -1401
GCAGAATGATCATATGGTAATCTCTGTTTATTTATTGAGAACAAACTTGCCGTTTCCATAACAGTCGACTATTTTACATTCCCACTAACAG          -1301
TGCATTAGGCTTCCAATTCTCTATGCCCTCCAACACTTGTTTCTCGGTTTAAAAGAAGTAGTCATCTTTGTAGGTGTCAGGTGGTATCTCATT        -1201
GTCGTTTGCTTCATGTTTCTCTAAAGATTAGTAATTTTCATATGCTTATTGACCATTTGTATATCTTCGGAGAAGTGTCTATTTGAGTCTTTCCCC    -1101
AATTTTGATTGGTTTGTTTGTTTCTTGAGTTGTAGGGAATTCTTTTATATTCTGGATATTAATCCCTTATCAGATATATTTGTTTTACAAATATTT    -1001
CTTTGTAACACAGAAACACACCAGTCTTCAAGGTTGGAAGCCAGTTAATCTGAGTACCATTTGTTACTCCTCCCCACACCATTCTTCCTCCTGAA     -901
ATCCTGGGAATTGGCCACCTCCTCTCCTTAGGCATCAAGCCCGTCTGCTTCTCCAAAGAACTCTTCCCCTCCACTACCTCAGAGTTAGCTTCC       -801
TCTCTTCAGCCAGTGATCCTGGGGTCCAGACACAATAATTAACCAAGAGAGGGTGAAAGGCTCCCTGCTGTGTTATGCAATGGCTCAGGCCCTTGTGA  -701
AGTGCCCAGGGACACCCAAGCACCTCCATCTCCAGGGCATGGTCCATCCCAGCTTTCACAGAACAGGAAAGCTGTGGAAGGAGTGTGGCAGCAGGGTA  -601
CCAATCCATATAGCCCTTGGCAACAACACATTTCCCACAAAGCACCCACCCAAAAGAACAACAACGATAGTGTTTAGTTTTTAGTAATGAGAACATAGT -501
TCTCATGACTAAAAGCCATCAGCCAGGAGAATCTGTTCTCAACCCTTTGCGTCTTCAACCCTTTGAAACTCTGACAGAAGCCATGAGAAGAATGTTCTCA -401
CTGAGTGCATGCACTCAAAATGATGCATTCAACTTCAATTCAGTTTCAGGATGTATGGCTGACCAATGCAGGGATTAGCAATGCAATAGTGA        -301
GAGGGCATGGGAGTGGGAATCTGCTGATCAAGCAAGTGGAGCCAGCAGCCCAGAAAAGAGCCCCCCTACCTGCTTTTCCTTCCTGGGCACTATTG     -201
CCCAGCAAATGCCTTCCTCTCTTCCGGTCTTCCACCTCCACCCCAAAATTTTCATTCTGCACAGTGATTGCCACATTCACTGGTTGAGAACAGAGACT  -101
GTAGCAACTCTGGCAGGGAGAAGCTGTCTCTGATGGCCTGAAGCTGTGGGCAGCTGGGCCAAGCCTAACCGCTATAAAAGGAGCTGCCCTCAGCCCTGC   -1
```

Exon 1 ATGTCTCTTGTCAGCTGTCTTTCAGAAGACCTG | GTAAGTGGGACTCTCTGGGTTGGCCCCGCACTTTGGGCTTCTCTGGGAGGGTCAGGGAAGTGGAG  100

CAGCCTTCCTGAGAGAGAGAGAAAGCTCAGGGAGGTCTGGAGCAAAGATACTCCTGGAGGTGGGAGTGAGGCAGGGATAAGGAAGGAGAGTATCCT    200

-continued

```
                                                                                                        300
CCAGCACCTTCCAGTGGGTAAGGGCACATTGTCTCCTAGGCTGACTTTTCTGAGCAGAGGGTGGGGTGGTAAGGAAGTCTACGGGCCCCGTGTGTG

400
TGCACATGTCTCTGTGAATGACCCTTCCCCTCCCACACGTGATCCCTATCATCCCTACTGCCCTGGCCATAGCCATCTGCTGTTTGGT

500
TATTTGAGAGTGCAGGCCAGGACAAGGCCATCGCTTGGGCATGAATCCTGCCTACTGCCCTGGCCAGATGCAAATTCCCTGCCATGGATTCCCCAG

Exon 2                       M  L  T  E  L  E  K  A  L  N  S  I  I  D  V  Y  H  K  Y  S      600
AAGGTTCTGTTTTCAG GTGGGGCAAGTTCCGTCGGGCATCATCTTCACCGAGCTGGAGAAAGCCTTGAACTCTATCATCGACGTCTACCACAAGTACTCC L  I  K  G  N  P  H  A  V  Y  R  D  D  L  K  K  L  L  E  T  E  C  P  Q  Y  I  R                    700
CTGATAAACGGCAACCCCCATGCTGTCTACAGGGATGACCTGAAGAAATTGCTAGAGACCGAGTGTCCTCAGTATATCACG GTGAGGAGGGGCTGGGGTGT 800
GGCGGGGGCTCTCTGCCCTGGTCCTGCCCTGCCAGGCGGTCCTGCCACCCTTCATAGATGCCTCGGCTCTCTGAGATCTTTAA K  K  G  A  D  V  W  F  K  E  L  D  I  N  T  D  G  A  V  N  F  Q  E                          900
ACTCTGGCTTCTCCTCAATCTTGACAG AAAAACGGTGCAGACGTCTGGTTCAAGAGTTGGATATCAACACTGATGGTGCAGTTAACTTCCAGCAG F  L  I  L  V  I  K  M  G  V  A  A  H  K  K  S  H  E  E  S  H  K  E  *   Exon 3                   1000
TTCCTCATTCTGGTGATAAAGATGGGCGTGGCAGCCCACAAGAAGAGTCATGAGGAAAGCCACAAAGAGTAGCTGAGTTACTGGGCCCAGAGGCTGGCCC 1100
CCTGGACATGTACCTGCAGAATAATAAAGTCATCAATACCTC ATCCCTCTCTCTTATGCTTTGTGGAATGAGGTTCCTCGGTGTGGAGGGAGGGTTGGA 1200
AAACCCACCATAGAGGAAGAAAAAGAAATCTGTAATGGCCTTTCCTGCTTTCCTGCTCAAGCCTTTCTGCTCCTACCCTCTGATCATTTATAGTGGTTCTGAAATGGTCGGGGATT 1300
GCCCCCTCATTCGAGCATTGGATTGAGGCTTAAGGATATAAGAACTGATACTGTTCTCAAGGTAAATCTTAGCTTCCAGTACCTGTCTTAGAGATGGAGAGAAGAAGAGCAAGACACCGAAGGGGGG 1400
TGGGAACAGGGTGGTAGTATAAGAACTGATACTGTTCTCAAGGTAAATCTTAGCTTCCAGTACCTGTCTTAGATGGTCTTGGAACCTTAGA 1500
GTGATAGCTACATAGAAGTGTGGGTGTGTCATGAGTCAGGTCCAAATGTCCACAATGTTCACACTCCTCACACAGGATAATCCTCACACCTGTCCACATACTGTACTTTCTC 1600
AGAGGCTGATTGTGTGTGTGGTGTCATGAGTCAGGTCCAAATGTCCACAATGTTCACACTCCTCACACAGGATAATCCTCACACCTGTCCACATACTGTACTTTCTC 1700
CTTGGGGATTTGAAAATTTTCCTCCCTCTCCAACTCCCAACTCAATTAAATGATAAAGGAATATCTAAAAATACTTCCAAGGCTGGTACAAGGG 1800
TTAAGTCAAAGAATAGGTTATTCATACGCTGCCTATGGGATTCTATGCTTTGTGATCAGAAAAATTATCTAAAAAACAAGAAAATCAACGGGAACCTTTTGACAAGAATGTCACCCCAAACTGATTTTC 1900
AGGCCAGAGACGAGTGGTTCTTCTCTGAGGTGCACATTAAAAACAAGAAAATCAACGGGAACCTTTTGACAAGAATGTCACCCCAAACTGATTTTC
```

| | |
|---|---|
| ATCCTGTGTGTCCCCAATTTTCTGTTGTCCCTCACTTAGGTCCTGGGGCAGTGTGTTACTGATGGGTAAAAAGGTACGAAGCTGTCACAGAATCACTAA | 2000 |
| ACCAGGGTTCTTAACTTGTCTGTCTATACATCTCTGAAATTGGGTTGAAGTTGTGTGCATCATTTTGAGTGACCGCACTGAGAACATTCCTCCACGGCTTC | 2100 |
| CATCGAGAGTCTCGAAAAGGCCCAACACCTCAAAAAGGTTAAGAACACTTGTCCTGCTTACTGGTTTTTAGTAACAAATGGCAGAGTATTCTCTCTGTC | 2200 |
| TCTCTCTCTTTTTTTTTTTTTCACACACCGTCTGTCTGTCACGTGACTAGAGTACAATGGGCATGATCATGGGCTCACTGTAGCCTCGAA | 2300 |
| CACCTGGGCTCAAGTAATCCTCCCACCTCAGCCTCTTAGTAGCTGGGACTACAGCATGAGCCACTGCCCTTGGCTAATTTTAAATTATTTTTTGTAG | 2400 |
| AGATGGAAACTTGCTATGTTGCCCACCTACTCTCAAACTCCTGGACTCAAGCGATCCTCCCAAAGTGCTGAGATTACAGTGTCATC | 2500 |
| CACACCACACCTGGCCAAAGATTGGAGTATTTTATTGCTATTGTTGTGCTGGGTGGGTGGGTGTATGCTTTGTGGCCACGTGTGTTGCCAAG | 2600 |
| GGCTAAATCAGTTCCTACCCTGCCCCAGTCCTCCCACAGCTTTCCTGCTCTGTGAAGCTAAGGATACACCCCGATGATAAGCTGTCAACATA | 2695. |

5. A DNA according to claim 2 having formula IX, wherein formula IX is:

$$\begin{array}{c}\text{(IX)}\end{array}$$

```
                                                     1
                                                     M  T  C  K  M  S
AAAACACTCTGTGTGGCTCCTCCCCTTTGACAGAGTGCAAGACGATGACTTGCAAAATGTCG
     10        20        30        40        50        60
         10                                      20
 Q  L  E  R  N  I  E  T  I  I  N  T  F  H  Q  Y  S  V  K  L
CAGCTGGAACGCAACATAGAGACCATCATCAACACCTTCCACCAATACTCTGTGAAGCTG
     70        80        90       100       110       120
         30                                      40
 G  H  P  D  T  L  N  Q  G  E  F  K  E  L  V  R  K  D  L  Q
GGGCACCCAGACACCCTGAACCAGGGGGAATTCAAAGAGCTGGTGCGAAAAGATCTGCAA
    130       140       150       160       170       180
         50                                      60
 N  F  L  K  K  E  N  K  N  E  K  V  I  E  H  I  M  E  D  L
AATTTTCTCAAGAACGAGAATAAGAATGAAAAGGTCATAGAACACATCATGGAGGACCTG
    190       200       210       220       230       240
         70                                      80
 D  T  N  A  D  K  Q  L  S  F  E  E  F  I  M  L  M  A  R  L
GACACAAATGCAGACAAGCAGCTGAGCTTCGAGGACTTCATCATGCTGATGGCCAGGCTA
    250       260       270       280       290       300
         90                                     100
 T  W  A  S  H  E  K  M  H  E  G  D  E  G  P  G  H  H  H  K
ACCTGGGCCTCCCACGAGAAGATGCACGAGGGTGACCAGGGCCCTGGCCACCACCATAAG
    310       320       330       340       350       360
        110
 P  G  L  G  E  C  T  P
CCAGGCCTCGCCCAGGGCACCCCCTAAGACCACAGTGGCCAAGATCACAGTGGCCACGGC
    370       380       390       400       410       420
CACGGCCACAGTCATGGTGGCCACGGCCACAGCCACCCAT.
    430       440       450       460
```

6. A DNA according to claim 2 having formula X, wherein formula X is:

```
ATCACTGTGGAGTAGGGGAAGGGCACTCCTGGGTGGCAAGGTGGGAGCTGGGCAGGGAGGTAGTGAAAGGGAACCTCCC                                    -901
CCCACACAACCCCCATTCCAAGAGGGCTTTGTGCGCAGGGCTAAGCCAACCTTTCTCCATAGGCAATGCCAGCAACTGCAGGTTCGTAGCAGCACAAC                  -801
GACATATCAAGCCACCAGGACCCTAAGTAAAAACAGTTGTCTCCCAAGTTCCTCCAACCCTTGCTGGGAGCAGGATTTAGAAAAATGATCCT                        -701
GAGAGATGCTAGAAACATATTCGCCCTGAGGCTCTCTCACTCAGACTCCAAGAGGAAGTATCATCAGAATTGCCCTTACATGTCAAGAACCAGAATAGCTGG              -601
CTCCCCTTCCTGCCAAGTCAGCAACCAGCTATGTGACCCTTGCTCAGGTCCATCTCCCCCTCTCAGTTCTTCATCTACAATGCAAGAGGGTTGCCACCT                 -501
CTGAGAACCCTTCTAACCCCAAATCTCACCTATGAATCTAAGAACACAACCCCTCGCCATCCTAAGTATCACAGAGCCAGGCAAGCATGGGTGAGAGCT                 -401
CACACCATCCTTGTGGACTAAAAGGAAGGGGCAGACTGCCATGGCAGAGTCAGCCTCGGGACTGCCCCCCATAGGTCCTCAGCCTCCTTCAACCTCAAA                 -301
CCCCATGCCGGCTGAGTGGTGCCAGAGAGCAGCAGGCTCGCTCCGGGGAGAGTAGGGCCTTAGGATAGAAAGGGAAATGAACTAAACAACCAGCTTCCTC                -201
CAAACCAGTTTCAGGCTCACCTGTGAACCAATCTTCCGAGACAGGGCCAAAGGGCAAGTGCCCAGTGCCCTCAGGAGCTGCTTATAAATGCCGAGCCTGGC              -101
CACCACTGCTCACCTGTGAACCAATCTTCCGAGACAGGGCCAAAGGGCAAGTGCCCAGTGCCCTCAGGAGCTGCTTATAAATGCCGAGCCTGGC                       -1
┌─Exon 1─┐
│AAACACTCTGTGTGGCCTCGGCTTTG│GTAAGTGAGCTGCCAGCTTCCCCAGGCAGAAGCCTGCCTGCCGATTCCTTCTTTCCTTCCCTGACCCAACTT               100
CCTTCCAAATCCTCCTCGTAGAAGCCCTTGTTGGCCCTGCTACTTTAAAGCTTCTTTCACATTTCTTAGTCATGTTCCCCTGGGGCCTCCTGC                        200
CCTCAAATGCTTGCTTTTGGCACTCTGTAGATATTCTAAAAATCATTTTGTACATGTGTGACAGGCCATCTCCCAGTTAAGTGCAGCCTGTGCT                      300
TTCTTTTATTTGCACTTCCCCACTATTTCTGTGAGTGCTTAGTAGGAAGTGTCAAAGAAGCTTGACAGCATTTTCTTCTAAGTGTCCAACTTCTTGG                   400
┌─Exon 2─┐          M  T  C  K  M  S  Q  L  E  R  N  I  E  T  I  I  N  T  F  H  Q  Y  S
TTTTCCATTACACAG│ACAGAGTGCAAGACGATGACTTGCAAAATGTCGCAGCTGGAACGCAACATAGAGACCATCATCAACACCTTCCACCAATACTTG│GTAGGGCTGGACTCTGGCAG  500
                                         10                      20
V  K  L  G  H  P  D  T  L  N  Q  G  E  F  K  E  L  V  R  K  D  L  Q  N  F  L  K
TGAAGCTGGGCCATCCAGACACCCTGAACCAGGGGGAATTCAAAGAGCTGGTGCGAAAAGATCTGCAAAATTTCTCAAG│GTAGGGCTGGACTCTGGCAG              600
     30                      40                      50
GTCTGACCCAGCCTCACCGGCCAGTTTGGGTTGACAAGGGGAGGATGGAGTATGGGCTACAGCAATCAAGGGGAAGATTTGAGCTCCTGAGCCAGCCCCA              700
```

```
                                                                                                                 -continued
AGACGCAGCGAGTGTCCTGTTATACAGGGCAGGTGGTCACAGTTACACAGGACGACGACAGGGTCAAGAAATTGCTCAATTGAACACCTGCTATTTGTCGGGC          800

CCTGTTCTGGGCACAGGGATGTAGTGGTAAATCCGAGCCCACTATTCCATGAGGAGACACACAGTAAAGTTGTTGCCAATAAAGAGCACAGATAAAGCC              900

AAATGCCAATAAGTGCCTGAAGAAAAATGAGATAGAGTCCGCCTGTGGGCAATGGGGCTGGGTGGGTGGGTGGAGGTGACCAGTTAGGGTACATGAGAAGGGCC        1000

TCTTTGAGGAGGTAACATTTGAGCTGAGCCCTGGGGGCTTTTCTAATCCTAAGGGTCTGCGGTGGAAAATGAATGCATAAACAGCACATGGAGAGCACCTGCACAGCACT 1100

GCGAACTTGGGGTGGAAACTTGGGGGCTTTTCTAATCCTAAGGGTCTGCGGTGGAAAATGAATGCATAAACAGCACATGGAGAGCACCTGCACAGCACT            1100

CAGGGAACTGGGAGGTTTTTCCCCGCTCCAAAAATGATTAGGCAGTTCTAAGAAAAAGGCTGAGCACTTCCAACAGCCTTTTGTTTCTTTTCAATT                 1300

TGGGGAAAGTCGGGAAACAGAGGGCCTGCATTAAGAAGGGTCGAACACATGGTCTCAGTCCAGTTCCAGTCCCGGAGCCAGACATCCTGGGGTAGGTCC              1400

CCAGCCCTCCAGTGCCCCTCCCCGCCTTGGTAAGGTGGAGAATTGCAGCCTTCAGAGTTACCCCCCGCTCTCCATAGGTCTCCATAGGTGGAGGCCTCAGG          1500

CAGGCAGGATGCTGGGTGGGGTAGGCAAGAAAGGGCCCAGCAAGCGATGCTGTGGGAAAAGGGAAGCAGAGCCAAAGCGATGCTGTCGCATTGGCTGGTACCC       1600

ACCTGACATCCCCACCAGAAGCAAAGCGATGCTGTGGGAAAAGGAAGCAGAGCCAAAGCGATGCTGTCGCATTGGCTGGTACCC                            1700

CACAGGTTCTGGGAGGGGACTTACCGAGGTGACTCAG ------------------ 360 NT ------------------ TGC                          2100

CTCGGGCCTCCCAAAGTGCTGGATTACAAGCATGAGCCACCCTGTCCGACCATCTCCCCTTTTATACTTTATCACACCCTGAGGTCAGCGGAGCACATA            2200

CTCTGCTCTCTGACCCTCCATCTCCCCTGCCACCTCCAGTGTTTTTCTAGTGTTCCCGTTGTATTGTTGAAATAAGTTCACTAATTGTTAACCTCC              2300

ACACCCAACCTCCAACCACCGCACCCCAAGCTGAAGTGCAGAGCCCTAGCACAGTGAACTGGCCTCTAAGTGCCTCTCAGATCTGAATTTGCATGCCCTCAATA       2400

GTCAAGCCTGTGAAACTAATGACCCTCTCTAGCACTGGTTCAAGTCTTCCTCCAGGAAGATACCATTCCTAGCTGTTAAAGTTGTTATAAGGACCAAA             2500

TGAGGTGACATTTCCAGGCTTACTCATGCCATGACCAGGGCAAGACCCTGGAACTCAGTTCCTCTTCTATAAATAGAGAATCAGCACCAAGTCACAGG              2600

GTCATGGAGGGAATAAACTGAGACCGTTTGTGCTCAGTGTCTGCTCCATTGTGCCACTCAGCCTATGGTCATTTTAATTTTTAATTCCACCC                  2700

CCAGGGTCGAGGCTTCCTTGTACATTTGCCAGCTGGTCATTTACTGTGCTCCCAGTCCCCACCTCTGGCCACACCCAGCTCTCACAGCTCTCTCTCCCCA           2800
```
| 51 | K | E | N | K | N | E | K | V | I | E | H | I | M | E | D | L | D | T | N | 60 | A | D | K | Q | L | S | F | E | E | P | I | 80 M |
|---|---|---|---|---|---|---|---|---|---|---|---|---|---|---|---|---|---|---|---|---|---|---|---|---|---|---|---|---|---|---|---|---|

```
CCCGCAG AAGGAGAATAAGAATCAAAAGGTCATACAACACATACTCCACCACCTCCACACAAATGCAGACAACCAGCTGAGCTTCGAGGAGTTCATCATG          2900
```

```
       L   M   A   R   L   T   W   A   S   H   E   K   M   H   E   G   D   E   G   P   G   H   H   K   P   G   L   G   E   G   T   P
                                     90                                                 100                                                110
CTGATGGCCAGGCTAACCTGGGCTTCCCACGACAAGATGCACGAGGGTGACGAGGGTCCCGGCCACCACCATAAGCCAGGCCTCGGGGAGGGCACCCCT                                          3000
       Exon 3
*  AAGACCACAGTGGCCAAGATCACAGTGGCCACGGCCACGGCCACAGTCATGTGGCCACAGGCCACTAATCAGGAGGCCAGGCCACCCTGCCTC                                             3100
                                                                                  CAAATAAAGTCTTCCTCCAA GTCAGTGCTCTGTG                         3200
TACCCAACCAGGGCTGTTATGTCAAACTGTCTTGGCTGTGGGCTAGGGGCTGGGGC
TGCTTCTTCCACCTCTTCTCCAACCCTGCCTTCCCAGGGCTCTGGCATTTAGACAGCCCTGTCCTTATCTGTGACTTCAGCCCCCTCATTCAGTATTAACA                                        3300
AAATGAGAAGCAGCAAAACATGGGTCTGTCCTGGGCCCCTTCCCTGACCATGTCCTCACTCTGACTTCAGGCCCACTGTTCAGATCCCA                                                   3400
GGCTCCCTGCCCCATCTCAGACACCCTGTCCAGCCTGTCCAGCCTGTCACTGTACACTGTAGAAAGCAAAAGGCATATCTCTACC                                                       3500
CCTTGATATGCCTGCTACTCACCAACCAGCCCAAGCCTGTCTTCACCCATCACTGTCTTCACCCATCACTGTCTTCAACAGATTCTATTCCTCT                                              3600
GAAAGTCTTCAGAAACTGGACCTAGATAGTGCCATGTCTGGGAGGAATATGGCACCAGGCAGTGGAAACAAGGACAGATCGGTGTGTATCTCACATTT                                           3700
GATCAGAGAGCATGATCTCTTAACAGACTGCCACCCTAATCAACGGAGTGCTCACACAAGTGGGAGTCTCAGAGCTTAGCCCTATGCCCACCCTGG                                            3800
TCTCAACAGAATGGCAGAGTGAAGAAATGAGCTCCAGTCCGGCCTCTGCAG                                                                                          3851.
```

7. A process for preparing a DNA coding for a compound of formula I or II, a mutant thereof having 1 to 3 codon substitutions or deletions of a fragment thereof comprising at least 15 nucleotides comprising the steps of:
  a) isolating mRNA from human mononuclear leukocytes, selecting the desired mRNA, preparing single-stranded DNA complementary to that mRNA, then double-stranded DNA therefrom (ds cDNA), or
  b) isolating genomic DNA from human cells and selecting the desired DNA using a DNA probe, and
  c) incorporating ds cDNA of step a) or ds cDNA of step b) into an appropriate expression vector,
  d) transforming an appropriate host microorganism with the obtained hybrid vector,
  e) selecting the transformed host which contains DNA coding for a compound of formula I or II, a mutant thereof having 1 to 3 codon substitutions or deletions of a fragment thereof comprising at least 15 nucleotides form hosts containing no coding DNA, and
  f) isolating the desired DNA,
wherein formula I is and, wherein Z2 is hydrogen, acyl or an optionally acylated peptide residue of 1 to 5 amino acids.

8. A hybrid vector comprising a DNA coding for a compound of formula I or II and further containing the yeast chromosomal autonomously replicating segment (ara) and the PHO5 promoter, wherein said vector is pJDB207R/PHO5-MRP-8, pJDB207R/PHO5-MRP-14 or pJDB207R/PHO5-MRP-14d, wherein formula I is $$Z_1-Leu-Thr-Glu-Leu-Glu-Lys-Ala-Leu-Asn-Ser-Ile-Ile-Asp-Val-Tyr-$$
$$His-Lys-Tyr-Ser-Leu-Ile-Lys-Gly-Asn-Phe-His-Ala-Val-Tyr-Arg-Asp-$$
$$Asp-Leu-Lys-Lys-Leu-Leu-Glu-Thr-Glu-Cys-Pro-Gln-Tyr-Ile-Arg-Lys-$$
$$Lys-Gly-Ala-Asp-Val-Trp-Phe-Lys-Glu-Leu-Asp-Ile-Asn-Thr-Asp-Gly-$$
$$Ala-Val-Asn-Phe-Gln-Glu-Phe-Leu-Ile-Leu-Val-Ile-Lys-Met-Gly-Val-$$
$$Ala-Ala-His-Lys-Lys-Ser-His-Glu-Glu-Ser-His-Lys-Glu,$$  (I)

wherein Z1 is hydrogen, acyl or the amino acid residue methionine, and
wherein formula II is:

$$Z_2-Ser-Gln-Leu-Glu-Arg-Asn-Ile-Glu-Thr-Ile-Ile-Asn-Thr-Phe-His-Gln-$$
$$Tyr-Ser-Val-Lys-Leu-Gly-His-Pro-Asp-Thr-Leu-Asn-Gln-Gly-Glu-Phe-Lys-$$
$$Glu-Leu-Val-Arg-Lys-Asp-Leu-Gln-Asn-Phe-Leu-Lys-Lys-Glu-Asn-Lys-Asn-$$
$$Glu-Lys-Val-Ile-Glu-His-Ile-Met-Glu-Asp-Leu-Asp-Thr-Asn-Ala-Asp-Lys-$$
$$Gln-Leu-Ser-Phe-Glu-Glu-Phe-Ile-Met-Leu-Met-Ala-Arg-Leu-Thr-Trp-Ala-$$
$$Ser-His-Glu-Lys-Met-His-Glu-Gly-Asp-Glu-Gly-Pro-Gly-His-His-His-Lys-$$
$$Pro-Gly-Leu-Gly-Glu-Gly-Thr-Pro,$$  (II)

$$Z_1-\text{Leu}-\text{Thr}-\text{Glu}-\text{Leu}-\text{Glu}-\text{Lys}-\text{Ala}-\text{Leu}-\text{Asn}-\text{Ser}-\underset{10}{\text{Ile}}-\text{Ile}-\text{Asp}-\text{Val}-\text{Tyr}- \quad\text{(I)}$$
$$\underset{20}{}\qquad\qquad\qquad\qquad\qquad\qquad\qquad\qquad\qquad\qquad\qquad\underset{30}{}$$

Leu—Thr—Glu—Leu—Glu—Lys—Ala—Leu—Asn—Ser—Ile—Ile—Asp—Val—Tyr—
His—Lys—Tyr—Ser—Leu—Ile—Lys—Gly—Asn—Phe—His—Ala—Val—Tyr—Arg—Asp—
Asp—Leu—Lys—Lys—Leu—Leu—Glu—Thr—Glu—Cys—Pro—Gln—Tyr—Ile—Arg—Lys—
Lys—Gly—Ala—Asp—Val—Trp—Phe—Lys—Glu—Leu—Asp—Ile—Asn—Thr—Asp—Gly—
Ala—Val—Asn—Phe—Gln—Glu—Phe—Leu—Ile—Leu—Val—Ile—Lys—Met—Gly—Val—
Ala—Ala—His—Lys—Lys—Ser—His—Glu—Glu—Ser—His—Lys—Glu, (positions 20, 40, 50, 60, 70, 80, 90, 93 as labeled)

wherein Z1 is hydrogen, acyl or the amino acid residue methionine, and
wherein formula II is:

$$Z_2-\text{Ser}-\text{Gln}-\text{Leu}-\text{Glu}-\text{Arg}-\text{Asn}-\text{Ile}-\text{Glu}-\text{Thr}-\text{Ile}-\text{Ile}-\text{Asn}-\text{Thr}-\text{Phe}-\text{His}-\text{Gln}- \quad\text{(II)}$$

(positions 6, 10, 20, 30, 40, 50, 60, 70, 80, 90, 100, 110, 114 as labeled)

Tyr—Ser—Val—Lys—Leu—Gly—His—Pro—Asp—Thr—Leu—Asn—Gln—Gly—Glu—Phe—Lys—
Glu—Leu—Val—Arg—Lys—Asp—Leu—Gln—Asn—Phe—Leu—Lys—Lys—Glu—Asn—Lys—Asn—
Glu—Lys—Val—Ile—Glu—His—Ile—Met—Glu—Asp—Leu—Asp—Thr—Asn—Ala—Asp—Lys—
Gln—Leu—Ser—Phe—Glu—Glu—Phe4—Ile—Met—Leu—Met—Ala—Arg—Leu—Thr—Trp—Ala—
Ser—His—Glu—Lys—Met—His—Glu—Gly—Asp—Glu—Gly—Pro—Gly—His—His—His—Lys—
Pro—Gly—Leu—Gly—Glu—Gly—Thr—Pro, and, wherein Z2 is hydrogen, acyl or an optionally acylated peptide residue of 1 to 5 amino acids.

9. A hybrid vector comprising a DNA coding for a compound of formula I or II and further containing the enhancer unit of the human cytomegalovirus major immediate-early gene, wherein said vector is pCMVe/MRP or pCMVe/MRP-14,
wherein formula I is $$Z_1-\text{Leu}-\text{Thr}-\text{Glu}-\text{Leu}-\text{Glu}-\text{Lys}-\text{Ala}-\text{Leu}-\text{Asn}-\text{Ser}-\text{Ile}-\text{Ile}-\text{Asp}-\text{Val}-\text{Tyr}- \quad\text{(I)}$$

His—Lys—Tyr—Ser—Leu—Ile—Lys—Gly—Asn—Phe—His—Ala—Val—Tyr—Arg—Asp—
Asp—Leu—Lys—Lys—Leu—Leu—Glu—Thr—Glu—Cys—Pro—Gln—Tyr—Ile—Arg—Lys—
Lys—Gly—Ala—Asp—Val—Trp—Phe—Lys—Glu—Leu—Asp—Ile—Asn—Thr—Asp—Gly—
Ala—Val—Asn—Phe—Gln—Glu—Phe—Leu—Ile—Leu—Val—Ile—Lys—Met—Gly—Val—
Ala—Ala—His—Lys—Lys—Ser—His—Glu—Glu—Ser—His—Lys—Glu, wherein Z1 is hydrogen, acyl or the amino acid residue methionine, and
wherein formula II is:

$$Z_2-\text{Ser}-\text{Gln}-\text{Leu}-\text{Glu}-\text{Arg}-\text{Asn}-\text{Ile}-\text{Glu}-\text{Thr}-\text{Ile}-\text{Ile}-\text{Asn}-\text{Thr}-\text{Phe}-\text{His}-\text{Gln}- \quad\text{(II)}$$

Tyr—Ser—Val—Lys—Leu—Gly—His—Pro—Asp—Thr—Leu—Asn—Gln—Gly—Glu—Phe—Lys—
Glu—Leu—Val—Arg—Lys—Asp—Leu—Gln—Asn—Phe—Leu—Lys—Lys—Glu—Asn—Lys—Asn—
Glu—Lys—Val—Ile—Glu—His—Ile—Met—Glu—Asp—Leu—Asp—Thr—Asn—Ala—Asp—Lys—
Gln—Leu—Ser—Phe—Glu—Glu—Phe4—Ile—Met—Leu—Met—Ala—Arg—Leu—Thr—Trp—Ala—
Ser—His—Glu—Lys—Met—His—Glu—Gly—Asp—Glu—Gly—Pro—Gly—His—His—His—Lys—
Pro—Gly—Leu—Gly—Glu—Gly—Thr—Pro, and, wherein Z2 is hydrogen, acyl or an optionally acylated peptide residue of 1 to 5 amino acids.

10. An embryonic lung cell L-132 stably transformed with pSV2neo and one of pCMVe/MRP-8 of pCMVe/MRP-14.

11. A DNA having the formula V, wherein formula V is:

wherein $Y_1$ is a flanking DNA residue of 12 nucleotides or more containing a promoter sequence, $Y_2$ is ATGACTTG-CAAA or absent and $Y_3$ is a flanking DNA residue of one or more nucleotides or absent, the complement of said DNA, a mutant of said DNA having 1 to 3 codon deletions or substitutions, a fragment of said DNA comprising at least 15

```
                         10
     M  L  T  E  L  E  K  A  L  N  S  I  I  D  V  Y  H  K  Y            (V)
Y1—ATGTTGACCGAGCTGGAGAAAGCCTTGAACTCTATCATCGACGTCTACCACAAGTAC
          10        20        30        40        50
  20                              30
  S  L  I  K  G  N  F  H  A  V  Y  R  D  D  L  K  K  L  L  E
TCCCTGATAAAGGGGAATTTCCATGCCGTCTACAGGGATGACCTCAAGAAATTGCTAGAG
          60        70        80        90        100       110
  40                              50
  T  E  C  P  Q  Y  I  R  K  K  G  A  D  V  W  F  K  E  L  D
ACCGAGTGTCCTCAGTATATCAGGAAAAAGGGTGCAGACGTCTGGTTCAAAGAGTTGGAT
          120       130       140       150       160       170
  60                              70
  I  N  T  D  G  A  V  N  F  Q  E  F  L  I  L  V  I  K  M  G
ATCAACACTGATGGTGCAGTTAACTTCCAGGAGTTCCTCATTCTGGTGATAAAGATGGGG
          180       190       200       210       220       230
  80                          90
  V  A  A  H  K  K  S  H  E  E  S  H  K  E  *
GTGGCAGCCCACAAAAAAAGCCATGAAGAAAGCCAVAAAGAGTAG—Y3,
          240       250       260       270       280
``` wherein $Y_1$ is a flanking DNA residue of 12 nucleotides or more containing a promoter sequence, and $Y_3$ is a flanking DNA residue of one or more nucleotides or absent, the complement of said DNA, a mutant of said DNA having 1 to 3 codon deletions or substitutions, a fragment of said DNA comprising at least 15 nucleotides or a genomic DNA wherein the DNA of formula V is interrupted by 1 or 2 introns.

12. A DNA encoding a compound of formula VI, wherein formula VI is:

nucleotides or a genomic DNA wherein the DNA of formula VI is interrupted by 1 or 2 introns.

13. A DNA encoding a compound of formula I or II, a mutant thereof having 1 to 3 codon deletions or substitutions or a fragment thereof comprising at least 15 nucleotides, wherein said DNA hybridizes with a DNA complementary to formula V or VI, wherein formula I is

```
            5              10                        20
            M  S  Q  L  E  R  N  I  E  T  I  I  N  T  F  H  Q  Y        (VI)
Y1—Y2—ATGTCGCAGCTGGAACGCAACATAGAGACCATCATCAACACCTTCCACCAATAC
              10        20        30        40        50
                     30                           40
  S  V  K  L  G  H  P  D  T  L  N  Q  G  E  F  K  E  L  V  R
TCTGTGAAGCTGGGGCACCCAGACACCCTGAACCAGGGGGAATTCAAAGAGCTGGTGCGA
          60        70        80        90        100       110
                              50                          60
  K  D  L  Q  N  F  L  K  K  E  N  K  N  E  K  V  I  E  H  I
AAAGATCTGCAAAATTTTCTCAAGAAGGAGAATAAGAATGAAAAGGTCATAGAACACATC
          120       130       140       150       160       170
                          70                      80
  M  E  D  L  D  T  N  A  D  K  Q  L  S  F  E  E  F  I  M  L
ATGGAGGACCTGGACACAAATGCAGACAAGCAGCTGAGCTTCGAGGAGTTCATCATGCTG
          180       190       200       210       220       230
                      90                          100
  M  A  R  L  T  W  A  S  H  E  K  M  H  E  G  D  E  G  P  G
ATGGCGAGGCTAACCTGGGCCTCCCACGAGAAGATGCACGAGGGTGACGAGGGCCCTGGC
          240       250       260       270       280       290
                      110
  H  H  H  K  P  G  L  G  E  G  T  P  *
CACCACCATAAGCCAGGCCTCGGGGAGGGCACCCCCTAA—Y3,
          300       310       320       330
```

$$Z_1—Leu—Thr—Glu—Leu—Glu—Lys—Ala—Leu—Asn—Ser—Ile—Ile—Asp—Val—Tyr— \quad (I)$$
$$His—Lys—Tyr—Ser—Leu—Ile—Lys—Gly—Asn—Phe—His—Ala—Val—Tyr—Arg—Asp—$$
$$Asp—Leu—Lys—Lys—Leu—Leu—Glu—Thr—Glu—Cys—Pro—Gln—Tyr—Ile—Arg—Lys—$$
$$Lys—Gly—Ala—Asp—Val—Trp—Phe—Lys—Glu—Leu—Asp—Ile—Asn—Thr—Asp—Gly—$$
$$Ala—Val—Asn—Phe—Gln—Glu—Phe—Leu—Ile—Leu—Val—Ile—Lys—Met—Gly—Val—$$
$$Ala—Ala—His—Lys—Lys—Ser—His—Glu—Glu—Ser—His—Lys—Glu,$$

wherein Z1 is hydrogen, acyl or the amino acid residue methionine,
wherein formula II is:

$$Z_2—Ser—Gln—Leu—Glu—Arg—Asn—Ile—Glu—Thr—Ile—Ile—Asn—Thr—Phe—His—Gln— \quad (II)$$
$$Tyr—Ser—Val—Lys—Leu—Gly—His—Pro—Asp—Thr—Leu—Asn—Gln—Gly—Glu—Phe—Lys—$$
$$Glu—Leu—Val—Arg—Lys—Asp—Leu—Gln—Asn—Phe—Leu—Lys—Lys—Glu—Asn—Lys—Asn—$$
$$Glu—Lys—Val—Ile—Glu—His—Ile—Met—Glu—Asp—Leu—Asp—Thr—Asn—Ala—Asp—Lys—$$
$$Gln—Leu—Ser—Phe—Glu—Glu—Phe—Ile—Met—Leu—Met—Ala—Arg—Leu—Thr—Trp—Ala—$$
$$Ser—His—Glu—Lys—Met—His—Glu—Gly—Asp—Glu—Gly—Pro—Gly—His—His—His—Lys—$$
$$Pro—Gly—Leu—Gly—Glu—Gly—Thr—Pro,$$

wherein Z2 is hydrogen, acyl or an optionally acylated peptide residue of 1 to 5 amino acids;
wherein Formula V is:

```
                        10
         M  L  T  E  L  E  K  A  L  N  S  I  I  D  V  Y  H  K  Y        (V)
Y1—ATGTTGACCGAGCTGGAGAAAGCCTTGAACTCTATCATCGACGTCTACCACAAGTAC
         10         20         30         40         50
 20                         30
  S  L  I  K  G  N  F  H  A  V  Y  R  D  D  L  K  K  L  L  E
TCCCTGATAAAGGGGAATTTCCATGCCGTCTACAGGGATGACCTCAAGAAATTGCTAGAG
         60         70         80         90        100        110
 40                         50
  T  E  C  P  Q  Y  I  R  K  K  G  A  D  V  W  F  K  E  L  D
ACCGAGTGTCCTCAGTATATCAGGAAAAAGGGTGCAGACGTCTGGTTCAAAGAGTTGGAT
        120        130        140        150        160        170
 60                         70
  I  N  T  D  G  A  V  N  F  Q  E  F  L  I  L  V  I  K  M  G
ATCAACACTGATGGTGCAGTTAACTTCCAGGAGTTCCTCATTCTGGTGATAAAGATGGGG
        180        190        200        210        220        230
 80                         90
  V  A  A  H  K  K  S  H  E  E  S  H  K  E  *
GTGGCAGCCCACAAAAAAAGCCATGAAGAAGCCAVAAAGAGTAG—Y3,
        240        250        260        270        280
``` wherein $Y_1$ is a flanking DNA residue of 12 nucleotides or more containing a promoter sequence, and $Y_3$ is a flanking DNA residue of one or more nucleotides or absent, the complement of said DNA, a mutant of said DNA having 1 to 3 codon deletions or substitutions, a fragment of said DNA comprising at least 15 nucleotides or a genomic DNA wherein the DNA of formula V is interrupted by 1 or 2 introns.
and wherein Formula VI is:

```
                  5                    10                         20
                  M  S  Q  L  E  R  N  I  E  T  I  I  N  T  F  H  Q  Y               (VI)
Y₁—Y₂—ATGTCGCAGCTGGAACGCAACATAGAGACCATCATCAACACCTTCCACCAATAC
              10         20         30         40         50

30                         40
         S  V  K  L  G  H  P  D  T  L  N  Q  G  E  F  K  E  L  V  R
         TCTGTGAAGCTGGGGCACCCAGACACCCTGAACCAGGGGGAATTCAAAGAGCTGGTGCGA
              60         70         80         90        100        110

50                              60
         K  D  L  Q  N  F  L  K  K  E  N  K  N  E  K  V  I  E  H  I
         AAAGATCTGCAAAATTTTCTCAAGAAGGAGAATAAGAATGAAAAGGTCATAGAACACATC
             120        130        140        150        160        170

70                          80
         M  E  D  L  D  T  N  A  D  K  Q  L  S  F  E  E  F  I  M  L
         ATGGAGGACCTGGACACAAATGCAGACAAGCAGCTGAGCTTCGAGGAGTTCATCATGCTG
             180        190        200        210        220        230

90                           100
         M  A  R  L  T  W  A  S  H  E  K  M  H  E  G  D  E  G  P  G
         ATGGCGAGGCTAACCTGGGCCTCCCACGAGAAGATGCACGAGGGTGACGAGGGCCCTGGC
             240        250        260        270        280        290

110
         H  H  H  K  P  G  L  G  E  G  T  P  *
         CACCACCATAAGCCAGGCCTCGGGGAGGGCACCCCCTAA—Y₃,
             300        310        320        330
``` wherein Y₁ is a flanking DNA residue of 12 nucleotides or more containing a promoter sequence, Y₂ is ATGACTTG-CAAA or absent and Y₃ is a flanking DNA residue of one or more nucleotides or absent, the complement of said DNA, a mutant of said DNA having 1 to 3 codon deletions or substitutions, a fragment of said DNA comprising at least 15 nucleotides or a genomic DNA wherein the DNA of formula VI is interrupted by 1 or 2 introns.

* * * * *